(12) United States Patent
LeBowitz et al.

(10) Patent No.: US 8,785,168 B2
(45) Date of Patent: Jul. 22, 2014

(54) FORMULATIONS FOR LYSOSOMAL ENZYMES

(75) Inventors: Jonathan LeBowitz, Novato, CA (US); Byeong Chang, Sherman Oaks, CA (US)

(73) Assignee: Biomarin Pharmaceutical Inc., Novato, CA (US)

( * ) Notice: Subject to any disclaimer, the term of this patent is extended or adjusted under 35 U.S.C. 154(b) by 182 days.

(21) Appl. No.: 13/378,745

(22) PCT Filed: Jun. 17, 2010

(86) PCT No.: PCT/US2010/039083
§ 371 (c)(1),
(2), (4) Date: Mar. 1, 2012

(87) PCT Pub. No.: WO2010/148253
PCT Pub. Date: Dec. 23, 2010

(65) Prior Publication Data
US 2012/0148556 A1 Jun. 14, 2012

Related U.S. Application Data

(60) Provisional application No. 61/187,747, filed on Jun. 17, 2009.

(51) Int. Cl.
*C12N 9/00* (2006.01)
(52) U.S. Cl.
USPC ........................................................ 435/183
(58) Field of Classification Search
USPC ........................................................ 435/183
See application file for complete search history.

(56) References Cited

U.S. PATENT DOCUMENTS

| | | |
|---|---|---|
| 4,309,776 A | 1/1982 | Berguer |
| 4,522,811 A | 6/1985 | Eppstein et al. |
| 4,749,570 A | 6/1988 | Poznansky |
| 4,801,575 A | 1/1989 | Pardridge |
| 4,902,505 A | 2/1990 | Pardridge et al. |
| 5,236,838 A | 8/1993 | Rasmussen et al. |
| 5,258,453 A | 11/1993 | Kopecek et al. |
| 5,356,804 A | 10/1994 | Desnick et al. |
| 5,399,346 A | 3/1995 | Anderson et al. |
| 5,405,942 A | 4/1995 | Bell et al. |
| 5,470,828 A | 11/1995 | Ballard et al. |
| 5,476,779 A | 12/1995 | Chen et al. |
| 5,549,892 A | 8/1996 | Friedman et al. |
| 5,561,119 A | 10/1996 | Jacquesy et al. |
| 5,580,757 A | 12/1996 | Desnick et al. |
| 5,633,234 A | 5/1997 | August et al. |
| 5,633,235 A | 5/1997 | Townsend et al. |
| 5,704,910 A | 1/1998 | Humes |
| 5,736,363 A | 4/1998 | Edwards et al. |
| 5,798,366 A | 8/1998 | Platt et al. |
| 5,817,623 A | 10/1998 | Ishii |
| 5,817,789 A | 10/1998 | Heartlein et al. |
| 5,827,703 A | 10/1998 | Debs et al. |
| 5,854,025 A | 12/1998 | Edwards et al. |
| 5,977,307 A | 11/1999 | Friden et al. |
| 5,981,194 A | 11/1999 | Jefferies et al. |
| 6,020,144 A | 2/2000 | Gueiros-Filho et al. |
| 6,027,921 A | 2/2000 | Heartlein et al. |
| 6,066,626 A | 5/2000 | Yew et al. |
| 6,083,725 A | 7/2000 | Selden et al. |
| 6,118,045 A | 9/2000 | Reuser et al. |
| 6,226,603 B1 | 5/2001 | Freire et al. |
| 6,235,874 B1 | 5/2001 | Wu et al. |
| 6,262,026 B1 | 7/2001 | Heartlein et al. |
| 6,270,989 B1 | 8/2001 | Treco et al. |
| 6,273,598 B1 | 8/2001 | Keck et al. |
| 6,281,010 B1 | 8/2001 | Gao et al. |
| 6,284,875 B1 | 9/2001 | Turpen et al. |
| 6,329,501 B1 | 12/2001 | Smith et al. |
| 6,344,436 B1 | 2/2002 | Smith et al. |
| 6,348,194 B1 | 2/2002 | Huse et al. |
| 6,441,147 B1 | 8/2002 | Turpen et al. |
| 6,451,600 B1 | 9/2002 | Rasmussen et al. |
| 6,455,494 B1 | 9/2002 | Jefferies et al. |
| 6,472,140 B1 | 10/2002 | Tanzi et al. |
| 6,534,300 B1 | 3/2003 | Canfield |
| 6,537,785 B1 | 3/2003 | Canfield |
| 6,566,099 B1 | 5/2003 | Selden et al. |
| 6,569,661 B1 | 5/2003 | Qin et al. |
| 6,596,500 B1 | 7/2003 | Kang et al. |
| 6,610,299 B1 | 8/2003 | Kolar et al. |
| 6,642,038 B1 | 11/2003 | Canfield |
| 6,670,165 B2 | 12/2003 | Canfield |

(Continued)

FOREIGN PATENT DOCUMENTS

| | | |
|---|---|---|
| EP | 0196056 A2 | 10/1986 |
| EP | 0466222 A1 | 1/1992 |

(Continued)

OTHER PUBLICATIONS

"Purification", The QIAexpressionist, pp. 63-107 (2001).
"QIAexpress Protein Purification System" QIAexpress—The Complete System for 6xHis Technology, pp. 7-12 (available before Feb. 19, 2009).
Achord et al., Human β-glucoronidase. II. Fate of infused human placental β-glucuronidase in the rat, Pediat. Res., 11:816-22 (1977).
Achord et al., Human β-glucuronidase: In vivo clearance and in vitro uptake by a glycoprotein recognition system on reticuloendothelial cells, Cell, 15:269-78 (1978).
Aeed et al., Glycosylation of recombinant prorenin in insect cells: the insect cell line Sf9 does not express the mannose 6-phosphate recognition signal, Biochemistry, 33:8793-7 (1994).
Aerts et al., Efficient routing of glucocerebrosidase to lysosomes requires complex oligosaccharide chain formation, Biochem. Biophys. Res. Commun., 141:452-8 (1986).
Allen et al., Metabolic correction of fucosidosis lymphoid cells by galaptin-alpha-L-fucosidase conjugates, Biochem. Biophys. Res. Commun., 172:335-40 (1990).
Altschul et al., Local alignment statistics, Methods Enzymol., 266:460-80 (1996).

(Continued)

*Primary Examiner* — Karen Cochrane Carlson
(74) *Attorney, Agent, or Firm* — Marshall, Gerstein & Borun LLP

(57) ABSTRACT

The present invention provides improved formulations for lysosomal enzymes useful for enzyme replacement therapy. Among other things, the present invention provides formulations that preserve or enhance the stability and/or efficacy of a lysosomal enzyme such as acid alpha-glucosidase.

21 Claims, 19 Drawing Sheets

(56) References Cited

U.S. PATENT DOCUMENTS

| | | | |
|---|---|---|---|
| 6,770,468 | B1 | 8/2004 | Canfield |
| 6,800,472 | B2 | 10/2004 | Canfield et al. |
| 6,828,135 | B2 | 12/2004 | Canfield |
| 6,861,242 | B2 | 3/2005 | Canfield |
| 6,905,856 | B2 | 6/2005 | Canfield et al. |
| 7,056,712 | B2 * | 6/2006 | Chen .............................. 435/183 |
| 7,067,127 | B2 | 6/2006 | Canfield |
| 7,135,322 | B2 | 11/2006 | Canfield et al. |
| 7,351,410 | B2 | 4/2008 | van Bree et al. |
| 7,354,576 | B2 | 4/2008 | Kakkis |
| 7,371,366 | B2 | 5/2008 | Canfield |
| 7,396,811 | B2 | 7/2008 | LeBowitz et al. |
| 7,442,372 | B2 | 10/2008 | Kakkis |
| 7,485,314 | B2 | 2/2009 | Kakkis et al. |
| 7,560,424 | B2 | 7/2009 | LeBowitz et al. |
| 7,629,309 | B2 | 12/2009 | LeBowitz et al. |
| 7,658,916 | B2 | 2/2010 | Zhu et al. |
| 7,723,296 | B2 * | 5/2010 | Zhu .............................. 514/17.7 |
| 2001/0006635 | A1 | 7/2001 | Bennett et al. |
| 2001/0025026 | A1 | 9/2001 | Heartlein et al. |
| 2002/0013953 | A1 | 1/2002 | Reuser et al. |
| 2002/0081654 | A1 | 6/2002 | Sandrin et al. |
| 2002/0110551 | A1 | 8/2002 | Chen |
| 2002/0142299 | A1 | 10/2002 | Davidson et al. |
| 2003/0004236 | A1 | 1/2003 | Meade |
| 2003/0021787 | A1 | 1/2003 | Hung et al. |
| 2003/0072761 | A1 | 4/2003 | LeBowitz |
| 2003/0077806 | A1 | 4/2003 | Selden et al. |
| 2003/0082176 | A1 | 5/2003 | LeBowitz et al. |
| 2004/0005309 | A1 | 1/2004 | LeBowitz et al. |
| 2004/0006008 | A1 | 1/2004 | LeBowitz et al. |
| 2004/0029779 | A1 | 2/2004 | Zhu et al. |
| 2004/0081645 | A1 | 4/2004 | Van Bree et al. |
| 2004/0248262 | A1 | 12/2004 | Koeberl et al. |
| 2005/0003486 | A1 | 1/2005 | Canfield et al. |
| 2005/0026823 | A1 | 2/2005 | Zankel et al. |
| 2005/0058634 | A1 | 3/2005 | Zhu |
| 2005/0142141 | A1 | 6/2005 | Pardridge |
| 2005/0170449 | A1 | 8/2005 | Canfield et al. |
| 2005/0244400 | A1 | 11/2005 | LeBowitz et al. |
| 2005/0281805 | A1 | 12/2005 | LeBowitz et al. |
| 2006/0051317 | A1 | 3/2006 | Batrakova et al. |
| 2006/0078542 | A1 | 4/2006 | Mah et al. |
| 2006/0286087 | A1 | 12/2006 | Kakkis et al. |
| 2006/0287224 | A1 | 12/2006 | DeFrees et al. |
| 2008/0003626 | A1 | 1/2008 | White et al. |
| 2008/0176285 | A1 | 7/2008 | Canfield |
| 2009/0041741 | A1 | 2/2009 | Sly et al. |
| 2010/0143297 | A1 | 6/2010 | Zhu et al. |
| 2011/0223147 | A1 * | 9/2011 | Lebowitz et al. ............ 424/94.3 |

FOREIGN PATENT DOCUMENTS

| | | |
|---|---|---|
| EP | 0599303 A2 | 6/1994 |
| EP | 1436316 | 7/2004 |
| WO | WO-91/04014 A1 | 4/1991 |
| WO | WO-91/14438 A1 | 10/1991 |
| WO | WO-92/22332 A2 | 12/1992 |
| WO | WO-93/06216 A1 | 4/1993 |
| WO | WO-93/10819 A1 | 6/1993 |
| WO | WO-94/02178 A1 | 2/1994 |
| WO | WO-95/02421 A1 | 1/1995 |
| WO | WO-00/53730 A2 | 9/2000 |
| WO | WO-01/19955 A2 | 3/2001 |
| WO | WO-01/53730 A1 | 7/2001 |
| WO | WO-02/044355 A2 | 6/2002 |
| WO | WO-02/56907 A2 | 7/2002 |
| WO | WO-02/087510 | 11/2002 |
| WO | WO-03/032727 A1 | 4/2003 |
| WO | WO-03/032913 A2 | 4/2003 |
| WO | WO-03/057179 A2 | 7/2003 |
| WO | WO-03102583 A1 | 12/2003 |
| WO | WO-2005/077093 A2 | 8/2005 |
| WO | WO-2005078077 A2 | 8/2005 |

OTHER PUBLICATIONS

Amalfitano et al., Recombinant human acid alpha-glucosidase enzyme therapy for infantile glycogen storage disease type II: results of a phase I/II clinical trial, Genet. Med., 3(2):132-8 (2001).

Anand, The Cure, Chapter 23, pp. 257-268, New York, NY: Harper Collins (2006).

Arai et al., Conformations of variably linked chimeric proteins evaluated by synchrotron X-ray small-angle scattering, Proteins, 57(4):829-38 (2004).

Armstrong et al., Uptake of circulating insulin-like growth factor-I into the cerebrospinal fluid of normal and diabetic rats and normalization of IGF-II mRNA content in diabetic rat brain, J. Neurosci. Res., 59(5):649-60 (2000).

Auletta et al., Receptor-mediated endocytosis and degradation of insulin-like growth factor I and II in neonatal rat astrocytes, J. Neurosci. Res., 31(1):14-20 (1992).

Authier et al., In vitro endosome-lysosome transfer of dephosphorylated EGF receptor and Shc in rat liver, FEBS Lett., 461(1-2):25-31 (1999).

Bach et al., Binding of mutants of human insulin-like growth factor II to insulin-like growth factor binding proteins 1-6, J. Biol. Chem., 268(13):9246-54 (1993).

Bartlett et al., CAVEAT: A program to facilitate the structure-derived design of biologically active molecules, Molecular Recognition: Chemical and Biological Problems, pp. 182-196 (1989).

Barton et al., Therapeutic response to intravenous infusions of glucocerebrosidase in a patient with Gaucher disease, Proc. Natl. Acad. Sci. USA, 87(5):1913-6 (1990).

Baxter, Insulin-like growth factor (IGF)-binding proteins: interactions with IGFs and intrinsic bioactivities, Am. J. Physiol. Endocrinol. Metab., 278(6):E967-76 (2000).

Becker et al., HLA and mate choice, J. Hum. Genet., 62:991 (1998).

Beljaars et al., Characteristics of the hepatic stellate cell-selective carrier mannose 6-phosphate modified albumin (M6P(28)-HSA), Liver, 21:320-8 (2001).

Beutler et al., Gaucher Disease, IN: Scriver et al., The Metabolic and Molecular Bases of Inherited Diseases, 8th ed., McGraw-Hill Professional, pp. 3635-3668 (2000).

Bickel et al., Delivery of peptides and proteins through the blood-brain barrier, Adv. Drug Deliv. Rev., 46(1-3):247-79 (2001).

Bijsterbosch et al., Native and modified lipoproteins as drug delivery systems, Adv. Drug Deliv. Rev., 5:231-51 (1990).

Bijvoet et al., Expression of cDNA-encoded human acid alpha-glucosidase in milk of transgenic mice, Biochim. Biophys. Acta, 1308(2):93-6 (1996).

Bijvoet et al., Human acid alpha-glucosidase from rabbit milk has therapeutic effect in mice with glycogen storage disease type II, Hum. Mol. Genet., 8(12):2145-53 (1999).

Bijvoet et al., Recombinant human acid alpha-glucosidase: high level production in mouse milk, biochemical characteristics, correction of enzyme deficiency in GSDII KO mice, Hum. Mol. Genet., 7(11):1815-24 (1998).

Birkenmeier et al., Increased life span and correction of metabolic defects in murine mucopolysaccharidosis type VII after syngeneic bone marrow transplantation, Blood, 78(11):3081-92 (1991).

Birkenmeier et al., Murine mucopolysaccharidosis type VII. Characterization of a mouse with beta-glucuronidase deficiency, J. Clin. Invest., 83(4):1258-66 (1989).

Bishop et al., Human a-galactosidase characterization and eukaryotic expression of the full-length cDNA and structural organization of the gene, IN: Lipid Storage Disorders Biological and Medical Aspects, vol. 150, pp. 809-822 (1987).

Blakey et al., Effect of chemical deglycosylation of ricin A chain on the in vivo fate and cytotoxic activity of an immunotoxin composed of ricin A chain and anti-Thy 1.1 antibody, Cancer Res., 47:947-52 (1987).

Borch et al., The cyanohydridoborate anion as a selective reducing agent. J. Am. Chem. Soc., 93:2897 (1971).

Brady et al., Enzyme replacement therapy in Fabry disease, J. Inherit. Metab. Dis., 24 Suppl 2:18-24 (2001).

Braulke et al., Insulin-like growth factors I and II stimulate endocytosis but do not affect sorting of lysosomal enzymes in human fibroblasts, J. Biol. Chem., 265(12):6650-5 (1990).

(56) References Cited

OTHER PUBLICATIONS

Braulke, Type-2 IGF receptor: a multi-ligand binding protein, Horm. Metab. Res., 31:242-6 (1999).

Brooks et al., Functional correction of established central nervous system deficits in an animal model of lysosomal storage disease with feline immunodeficiency virus-based vectors, Proc. Natl. Acad. Sci. USA, 99(9):6216-21 (2002).

Brooks, Immune response to enzyme replacement therapy in lysosomal storage disorder patients and animal models, Mol. Genet. Metab., 68:268-75 (1999).

Brown et al., Structure of a functional IGF2R fragment determined from the anomalous scattering of sulfur, EMBO J., 21:1054-62 (2002).

Bungard, Design of Prodrugs, pp. 7-9 and 21-24, Elsevier (1985).

Burgisser et al., Mutants of human insulin-like growth factor II with altered affinities for the type 1 and type 2 insulin-like growth factor receptor, J. Biol. Chem., 266:1029-33 (1991).

Cacciari et al., Somatomedin C in pediatric pathophysiology, Pediatrician, 14(3):146-53 (1987).

Calhoun et al., Fabry disease: isolation of a cDNA clone encoding human alpha-galactosidase A, Proc. Natl. Acad. Sci. USA, 82:7364-8 (1985).

Carter et al., Improved oligonucleotide site-directed mutagenesis using M13 vectors. Nucleic Acids Res., 13:4331 (1986).

Cascieri et al., Structural analogs of human insulin-like growth factor (IGF) I with altered affinity for type 2 IGF receptors, J. Biol. Chem., 264(4):2199-202 (1989).

Chodobski et al., Choroid plexus: target for polypeptides and site of their synthesis, Microsc. Res. Tech., 52:65-82 (2001).

Chothia, The nature of the accessible and buried surfaces in proteins, J. Mol. Biol., 105:1-12 (1976).

Dahms et al., Mannose 6-phosphate receptors and lysosomal enzyme targeting, J. Biol. Chem., 264(21):12115-8 (1989).

Daly et al., Neonatal gene transfer leads to widespread correction of pathology in a murine model of lysosomal storage disease, Proc. Natl. Acad. Sci. USA, 96(5):2296-300 (1999).

Desnick et al., Enzyme replacement and enhancement therapies: lessons from lysosomal disorders, Nat. Rev. Genet, 3(12):954-66 (2002).

Devedijan et al., Transgenic mice overexpressing insulin-like growth factor-II in beta cells develop type 2 diabetes, J. Clin. Invest., 105(6):731-40 (2000).

Devi et al., An insulin-like growth factor II (IGF-II) affinity-enhancing domain localized within extracytoplasmic repeat 13 of the IGF-II/mannose 6-phosphate receptor, Mol. Endocrinol., 12:1661-72 (1998).

Difalco et al., Efficacy of an insulin-like growth factor-interleukin-3 fusion protein in reversing the hematopoietic toxicity associated with azidothymidine in mice, J. Pharmacol. Exp. Ther., 284:449-54 (1998).

Difalco et al., Preparation of a recombinant chimaera of insulin-like growth factor II and interleukin 3 with high proliferative potency for haemopoietic cells, Biochem. J., 326(Pt. 2):407-13 (1997).

Diment et al., Generation of macrophage variants with 5-azacytidine: selection for mannose receptor expression, J. Leukoc. Biol., 42:485-90 (1987).

Dixon, Computer-aided drug design: getting the best results, Trends Biotechnol., 10(10):357-63 (1992).

Dobrenis et al., Neuronal lysosomal enzyme replacement using fragment C of tetanus toxin, Proc. Natl. Acad. Sci. USA, 89(6):2297-301 (1992).

Douglass et al., Chemical deglycosylation can induce methylation, succinimide formation, and isomerization, J. Protein Chem., 20(7);571-6 (2001).

Duffy et al., Human blood-brain barrier insulin-like growth factor receptor, Metabolism, 37(2):136-40 (1988).

Duguay et al., Post-translational processing of the insulin-like growth factor-2 precursor. Analysis of O-glycosylation and endoproteolysis, J. Biol. Chem., 273:18443-51 (1998).

Dziegielewska et al., The ins and outs of brain-barrier mechanisms, Trends Neurosci., 25(2):69-71 (2002).

Eisen et al., HOOK: a program for finding novel molecular architectures that satisfy the chemical and steric requirements of a macromolecule binding site, Proteins, 19(3):199-221 (1994).

European search report for EP08000935 (2008).

European supplementary partial search report for European application No. EP03736779 (mailing date Apr. 5, 2007).

Europen search report for EP02801739 (2005).

Extended European Search Report for corresponding European application No. EP09743707.3, dated Aug. 17, 2011.

Forbes et al., Contribution of residues A54 and L55 of the human insulin-like growth factor-II (IGF-II) A domain to Type 2 IGF receptor binding specificity, Growth Factors, 19(3):163-73 (2001).

Foxwell et al., The preparation of deglycosylated ricin by recombination of glycosidase-treated A- and B-chains: effects of deglycosylation on toxicity and in vivo distribution, Biochim. Biophys. Acta, 923(1);59-65 (1987).

Francis et al., Insulin-like growth factor (IGF)-II binding to IGF-binding proteins and IGF receptors is modified by deletion of the N-terminal hexapeptide or substitution of arginine for glutamate-6 in IGF-II, Biochem. J., 293(Pt. 3):713-9 (1993).

Frank et al., Binding and internalization of insulin and insulin-like growth factors by isolated brain microvessels, Diabetes, 35(6):654-61 (1986).

Friden et al, Anti-transferrin receptor antibody and antibody-drug conjugates cross the blood-brain barrier, Proc. Natl. Acad. Sci. USA, 88(11):4771-5 (1991).

Fukuda et al., Autophagy and lysosomes in Pompe disease, Autophagy, 2(4):318-20 (2006).

Fukuda et al., Autophagy and mistargeting of therapeutic enzyme in skeletal muscle in Pompe disease, Mol. Ther., 14(6):831-9 (2006).

Fukuda et al., Dysfunction of endocytic and autophagic pathways in a lysosomal storage disease, Ann. Neurol., 59(4):700-8 (2006).

Fukuta et al., Insulin fragments as a carrier for peptide delivery across the blood-brain barrier, Pharm. Res., 11:1681-8 (1994).

Godar et al., M6P/IGFII-receptor complexes urokinase receptor and plasminogen for activation of transforming growth factor-beta1, Eur. J. Immunol., 29(3):1004-13 (1999).

Golden et al., Human blood-brain barrier leptin receptor. Binding and endocytosis in isolated human brain microvessels, J. Clin. Invest., 99(1):14-8 (1997).

Gordon et al., A role for PACE4 in the proteolytic activation of anthrax toxin protective antigen, Infect. Immun., 65(8):3370-5 (1997).

Gozes et al., Neuropeptides: brain messengers of many faces, Trends Neurosci., 24(12):687-90 (2001).

Graham et al., Characteristics of a human cell line transformed by DNA from human adenovirus type 5, J. Gen. Virol., 36(1): 59-74 (1977).

Grimme et al., Endocytosis of insulin-like growth factor II by a mini-receptor based on repeat 11 of the mannose 6-phosphate/insulin-like growth factor II receptor, J. Biol. Chem., 275(43):33697-703 (2000).

Grubb et al., Chemically modified beta-glucuronidase crosses blood-brain barrier and clears neuronal storage in murine mucopolysaccharidosis VII, Proc. Natl. Acad. Sci. USA, 105(7):2616-21 (2008).

Grubb et al., Large scale purification of phosphorylated recombinant β-glucuronidase from over-expressing mouse L cells, FASEB J., 7:1255a (1993).

Hashimoto et al., Binding sites and binding properties of binary and ternary complexes of insulin-like growth factor-II (IGF-II), IGF-binding protein-3, and acid-labile subunit, J. Biol. Chem., 272:27936-42 (1997).

Hashimoto et al., N-terminal deletion mutants of insulin-like growth factor-II (IGF-II) show Thr7 and Leu8 important for binding to insulin and IGF-I receptors and Leu8 critical for all IGF-II functions, J. Biol. Chem., 270(30):18013-8 (1995).

Haskell et al., Intracellular trafficking of the JNCL protein CLN3, Mol. Genet. Metab., 66:253-60 (1999).

Henikoff et al., Amino acid substitution matrices from protein blocks, Proc. Natl. Acad. Sci. USA, 89:10915-9 (1992).

(56) References Cited

OTHER PUBLICATIONS

Hickman et al., A recognition marker required for uptake of a lysosomal enzyme by cultured fibroblasts, Biochem. Biophys. Res. Commun., 57:55-61 (1974).
Hirschhorn et al., Glycogen storage disease type II: Acid alpha-glucosidase (acid maltase) deficiency, In: Schriver et al. (eds.), The Metabolic and Molecular Basis of Inherited Disease, 8th Ed., New York: McGraw-Hill, pp. 3389-3420 (2001).
Hoefsloot et al., Expression and routeing of human lysosomal alpha-glucosidase in transiently transfected mammalian cells, Biochem. J., 272:485-92 (1990).
Houba et al., Improved characteristics of a human beta-glucuronidase-antibody conjugate after deglycosylation for use in antibody-directed enzyme prodrug therapy, Bioconjug. Chem., 7:606-11 (1996).
International Preliminary Report on Patentability for corresponding International application No. PCT/US2009/043207, dated Nov. 9, 2010.
International Preliminary Report on Patentability for corresponding international application No. PCT/US2010/039083, dated Dec. 20, 2011.
International Search Report and Written Opinion from corresponding international application No. PCT/US2010/039083, mailing date Mar. 29, 2011.
International Search Report for corresponding International application No. PCT/US2009/043207, mailing date Feb. 16, 2010.
International Search Report for PCT/US02/13835 (2002).
International Search Report for PCT/US02/32968 (2002).
International Search Report for PCT/US02/32996 (2002).
International Search Report for PCT/US03/17211 (2003).
International Search Report for PCT/US07/23881 (2009).
Ishibashi et al., Asialoglycoprotein receptor deficiency in mice lacking the minor receptor subunit, J. Biol. Chem., 269:27803-6 (1994).
Islam et al., C-terminal processing of human beta-glucuronidase. The propeptide is required for full expression of catalytic activity, intracellular retention, and proper phosphorylation, J. Biol. Chem., 268(30):22627-33 (1993).
Jacob et al., Sucrase is an intramolecular chaperone located at the C-terminal end of the sucrase-isomaltase enzyme complex, J. Biol. Chem., 277(35):32141-8 (2002).
Jones, Analysis of polypeptides and proteins, Adv. Drug Deliv. Rev., 10:29-90 (1993).
Journet et al., Proteomic analysis of human lysosomes: application to monocytic and breast cancer cells, Proteomics, 2(8):1026-40 (2002).
Juuti-Uusitalo et al., Selective targeting of avidin/mannose 6-phosphate receptor chimeras to early or late endosomes, Eur. J. Cell Biol., 79(7):458-68 (2000).
Kang et al., Mannose 6-phosphate/insulin-like growth factor II receptor mediates the growth-inhibitory effects of retinoids, Cell Growth Differ., 10(8):591-600 (1999).
Kang et al., Mannose-6-phosphate/insulin-like growth factor-II receptor is a receptor for retinoic acid, Proc. Natl. Acad. Sci. USA, 94(25):13671-6 (1997).
Kang et al., Retinoic acid alters the intracellular trafficking of the mannose-6-phosphate/insulin-like growth factor II receptor and lysosomal enzymes, Proc. Natl. Acad. Sci. USA, 95:13687-91 (1998).
Kerr et al., Comparison of recombinant and synthetically formed monoclonal antibody-beta-lactamase conjugates for anticancer prodrug activation, Bioconjug. Chem., 10(6)1084-9 (1999).
Kiess et al., Biochemical evidence that the type II insulin-like growth factor receptor is identical to the cation-independent mannose 6-phosphate receptor, J. Biol. Chem., 263:9339-44 (1988).
Kiess et al., Insulin-like growth factor II (IGF-II) and the IGF-II/mannose-6-phosphate receptor: the myth continues, Horm. Res., 41 Suppl 2:66-73 (1994).
Kiess et al., Insulin-like growth factor-II (IGF-II) inhibits both the cellular uptake of beta-galactosidase and the binding of beta-galactosidase to purified IGF-II/mannose 6-phosphate receptor, J. Biol. Chem., 264(8):4710-4 (1989).
Kikuchi et al., Clinical and metabolic correction of pompe disease by enzyme therapy in acid maltase-deficient quail, J. Clin. Invest., 101(4):827-33 (1998).
Kim et al., High-level expression and simple purification of recombinant human insulin-like growth factor I, J. Biotechnol., 48(1-2):97-105 (1996).
Kishnani et al., A retrospective, multinational, multicenter study on the natural history of infantile-onset Pompe disease, J. Pediatr., 148:671-6 (2006).
Kishnani et al., Chinese hamster ovary cell-derived recombinant human acid alpha-glucosidase in infantile-onset Pompe disease, J. Pediatr., 149:89-97 (2006).
Kishnani et al., Recombinant human acid [alpha]-glucosidase: major clinical benefits in infantile-onset Pompe disease, Neurology, 68:99-109 (2007).
Korner et al., Mannose 6-phosphate/insulin-like growth factor II receptor fails to interact with G-proteins. Analysis of mutant cytoplasmic receptor domains, J. Biol. Chem., 270:287-95 (1995).
Kundra et al., Asparagine-linked oligosaccharides protect Lamp-1 and Lamp-2 from intracellular proteolysis, J. Biol. Chem., 274:31039-46 (1999).
Langford et al., Leishmania: codon utilization of nuclear genes, Exp. Parasitol., 74:360-1 (1992).
Lau et al., Loss of the imprinted IGF2/cation-independent mannose 6-phosphate receptor results in fetal overgrowth and perinatal lethality, Genes Dev., 8:2953-64 (1994).
Lebowitz et al., A breach in the blood-brain barrier, Proc. Natl. Acad. Sci. USA, 102:14485-6 (2005).
Lebowitz et al., Glycosylation-independent targeting enhances enzyme delivery to lysosomes and decreases storage in mucopolysaccharidosis type VII mice, Proc. Natl. Acad. Sci. USA, 101:3083-8 (2004).
Lee et al., Mannose receptor-mediated regulation of serum glycoprotein homeostasis, Science, 295:1898-901 (2002).
Lemansky et al., Synthesis and processing of alpha-galactosidase A in human fibroblasts. Evidence for different mutations in Fabry disease, J. Biol. Chem., 262:2062-5 (1987).
Linnell et al., Real time kinetics of insulin-like growth factor II (IGF-II) interaction with the IGF-II/mannose 6-phosphate receptor: the effects of domain 13 and pH, J. Biol. Chem., 276:23986-91 (2001).
Liu et al., Intranasal administration of insulin-like growth factor-I bypasses the blood-brain barrier and protects against focal cerebral ischemic damage, J. Neurol. Sci., 187:91-7 (2001).
Ludwig et al., Mouse mutants lacking the type 2 IGF receptor (IGF2R) are rescued from perinatal lethality in Igf2 and Igf1r null backgrounds, Dev. Biol., 177:517-35 (1996).
Ludwig et al., Roles for mannose-6-phosphate receptors in lysosomal enzyme sorting, IGF-II binding and clathrin-coat assembly, Trends Cell Biol., 5:202-6 (1995).
Luthi et al., Mutants of human insulin-like growth factor II (IGF II). Expression and characterization of truncated IGF II and of two naturally occurring variants, Eur. J. Biochem., 205(2):483-90 (1992).
Lynch et al., High-resolution light microscopy (HRLM) and digital analysis of Pompe disease pathology, J. Histochem. Cytochem., 53:63-73 (2005).
Magee et al., Insulin-like growth factor I and its binding proteins: a study of the binding interface using B-domain analogues, Biochemistry, 38(48):15863-70 (1999).
Mah et al., Physiological correction of pompe disease by systemic delivery of adeno-associated virus serotype I vectors, Molecular Therapy, 15:501-7 (2007).
Mahuran et al., Proteolytic processing of pro-alpha and pro-beta precursors from human beta-hexosaminidase. Generation of the mature alpha and beta a beta b subunits, J. Biol. Chem., 263:4612-8 (1988).
Martin, Computer-assisted rational drug design, Methods Enzymol., 203:487-613 (1991).
Martiniuk et al., Correction of glycogen storage disease type II by enzyme replacement with a recombinant human acid maltase produced by over-expression in a CHO-DHFR(neg) cell line, Biochem. Biophys. Res. Commun., 276:917-23 (2000).

(56) References Cited

OTHER PUBLICATIONS

Martiniuk et al., Recombinant human acid alpha-glucosidase generated in bacteria: antigenic, but enzymatically inactive, DNA Cell Biol., 11:701-6 (1992).
Mather et al., Culture of testicular cells in hormone-supplemented serum-free medium, Ann. NY Acad. Sci., 383:44-68 (1982).
Mather, Establishment and characterization of two distinct mouse testicular epithelial cell lines, Biol. Reprod., 23(1):243-52 (1980).
Mazzolla et al., Enhanced resistance to *Cryptococcus neoformans* infection induced by chloroquine in a murine model of meningoencephalitis, Antimicrob. Agents Chemother., 41:802-7 (1997).
Meynial-Salles et al., In vitro glycosylation of proteins: an enzymatic approach, J. Biotechnol., 46:1-14 (1996).
Moehring et al., Strains of CHO-K1 cells resistant to Pseudomonas exotoxin A and cross-resistant to diphtheria toxin and viruses, Infect. Immun., 41(3):998-1009 (1983).
Molloy et al., Human furin is calcium-dependent serine endoprotease that recognizes the sequence ARG-X-X-ARG and efficiently cleaves anthrax toxin protective antigen, J. Biol. Chem., 267:16396-402 (1992).
Moreland et al., Lysosomal acid alpha-glucosidase consists of four different peptides processed from a single chain precursor, J. Biol. Chem., 280:6780-91 (2005).
Morgan et al., Insulin-like growth factor II receptor as a multifunctional binding protein, Nature, 329:301-7 (1987).
Myszka et al., Kinetic, equilibrium, and thermodynamic analysis of macromolecular interactions with BIACORE, Methods Enzymol., 323:325-40 (2000).
Newrzella et al., Functional analysis of the glycosylation of murine acid sphingomyelinase, J. Biol. Chem., 271:32089-95 (1996).
Nilsson et al., Induction of immune tolerance in patients with hemophilia and antibodies to factor VIII by combined treatment with intravenous IgG, cyclophosphamide, and factor VIII, N. Engl. J. Med., 318:947-50 (1988).
Nissley et al., Reciprocal modulation of binding of lysosomal enzymes and insulin-like growth factor-II (IGF-II) to the mannose 6-phosphate/IGF-II receptor, Adv. Exp. Med. Biol., 293:311-24 (1991).
Niwa et al., Efficient selection for high-expression transfectants with a novel eukaryotic vector, Gene, 108:193-9 (1991).
Nolan et al., Binding of insulin-like growth factor II (IGF-II) by human cation-independent mannose 6-phosphate receptor/IGF-II receptor expressed in receptor-deficient mouse L cells, Cell Regul., 1(2):197-213 (1990).
Novazyme Website printouts (2001).
Nykjaer et al., Mannose 6-phosphate/insulin-like growth factor-II receptor targets the urokinase receptor to lysosomes via a novel binding interaction, J. Cell Biol., 141:815-28 (1998).
O'Connor et al., Enzyme replacement therapy for murine mucopolysaccharidosis type VII leads to improvements in behavior and auditory function, J. Clin. Invest., 101:1394-400 (1998).
O'Dell et al., Insulin-like growth factor II (IGF-II), Int. J. Biochem. Cell Biol., 30:767-71 (1998).
Oksche et al., Late endosomal/lysosomal targeting and lack of recycling of the ligand-occupied endothelin B receptor, Mol. Pharmacol., 57(6):1104-13 (2000).
Paasche et al., Mechanisms of endothelin receptor subtype-specific targeting to distinct intracellular trafficking pathways, J. Biol. Chem., 276:34041-50 (2001).
Pardridge et al., Drug delivery to the brain, J. Cereb. Blood Flow Metab., 17:713-31 (1997).
Pardridge, Targeting neurotherapeutic agents through the blood-brain barrier, Arch. Neurol., 59:35-40 (2002).
Pauly et al., Complete correction of acid alpha-glucosidase deficiency in Pompe disease fibroblasts in vitro, and lysosomally targeted expression in neonatal rat cardiac and skeletal muscle, Gene Ther., 5(4):473-80 (1998).

PCT International Preliminary report on Patentability for International Application No. PCT/US05/004286) (Date of issuance Aug. 14, 2006).
PCT International Search Report for International Application No. PCT/US05/004286 (Date of mailing Aug. 31, 2005).
Pine, Organic Chemistry, 5th ed., McGraw Hill, p. 770 (1987).
Polychronakos et al., Effects of mannose-6-phosphate on receptor-mediated endocytosis of insulin-like growth factor-II, Endocrinology, 127(4):1861-6 (1990).
Poznansky et al., Enzyme replacement therapy in fibroblasts from a patient with cholesteryl ester storage disease, FASEB J., 3:152-6 (1989).
Prince et al., Lipoprotein receptor binding, cellular uptake, and lysosomal delivery of fusions between the receptor-associated protein (RAP) and alpha-L-iduronidase or acid alpha-glucosidase, J. Biol. Chem., 279(33):35037-46 (2004).
Pulford et al., Uptake of circulating insulin-like growth factors (IGFs) into cerebrospinal fluid appears to be independent of the IGF receptors as well as IGF-binding proteins, Endocrinology, 142(1):213-20 (2001).
Raben et al., Acid alpha-glucosidase deficiency (glycogenosis type II, Pompe disease), Curr. Mol. Med., 2(2):145-66 (2002).
Raben et al., Targeted disruption of the acid alpha-glucosidase gene in mice causes an illness with critical features of both infantile and adult human glycogen storage disease type II, J. Biol. Chem., 273(30):19086-92 (1998).
Ramalingam et al., Binding to the transferrin receptor is required for endocytosis of HFE and regulation of iron homeostasis, Nat. Cell Biol., 2(12):953-7 (2000).
Reinhardt et al., Insulin-like growth factors cross the blood-brain barrier, Endocrinology, 135(5):1753-61 (1994).
Reuser et al., Biochemical, immunological, and cell genetic studies in glycogenosis type II, Am. J. Hum. Genet., 30(2):132-43 (1978).
Rhee et al., High-level expression of human insulin-like growth factor II in *Escherichia coli*, J. Biotechnol., 13(4):293-304 (1990).
Robyt, Essentials of Carbohydrate Chemistry, pp. 34-35 and p. 350, Springer (1998).
Rocca et al., Involvement of the ubiquitin/proteasome system in sorting of the interleukin 2 receptor beta chain to late endocytic compartments, Mol. Biol. Cell, 12(5):1293-301 (2001).
Rosenberg et al., Immunosurveillance of alglucerase enzyme therapy for Gaucher patients: induction of humoral tolerance in seroconverted patients after repeat administration, Blood, 93(6):2081-8 (1999).
Roth et al., Mutants of human insulin-like growth factor II: expression and characterization of analogs with a substitution of TYR27 and/or a deletion of residues 62-67, Biochem. Biophys. Res. Commun., 181(2):907-14 (1991).
Russell et al., Recombinant proteins for genetic disease, Clin. Genet., 55:389-94 (1999).
Sakano et al., The design, expression, and characterization of human insulin-like growth factor II (IGF-II) mutants specific for either the IGF-II/cation-independent mannose 6-phosphate receptor or IGF-I receptor, J. Biol. Chem., 266(31):20626-35 (1991).
Samoylova et al., Elucidation of muscle-binding peptides by phage display screening, Muscle Nerve, 22(4):460-6 (1999).
Sandoval et al., Enhanced proliferative effects of a baculovirus-produced fusion protein of insulin-like growth factor and alpha(1)-proteinase inhibitor and improved anti-elastase activity of the inhibitor with glutamate at position 351, Protein Eng., 15(5):413-8 (2002).
Sandoval et al., The fusion of IGF I with stromal cell-derived factor I or alpha1 proteinase inhibitor alters their mitogenic or chemotactic activities while keeping their ability to inhibit HIV-1-gp120 binding, Biochem. Pharmacol., 65(12):2055-63 (2003).
Sands et al., Biodistribution, kinetics, and efficacy of highly phosphorylated and non-phosphorylated beta-glucuronidase in the murine model of mucopolysaccharidosis VII, J. Biol. Chem., 276:43160-5 (2001).
Sands et al., Enzyme replacement therapy for murine mucopolysaccharidosis type VII, J. Clin. Invest., 93:2324-31 (1994).

(56) References Cited

OTHER PUBLICATIONS

Sands et al., Murine mucopolysaccharidosis type VII: long term therapeutic effects of enzyme replacement and enzyme replacement followed by bone marrow transplantation, J. Clin. Invest., 99:1596-605 (1997).
Shin et al., Functional properties of antibody insulin-like growth factor fusion proteins, J. Biol. Chem., 269(7):4979-85 (1994).
Shipley et al., The role of glycosylation and phosphorylation in the expression of active human beta-glucuronidase, J. Biol. Chem., 268(16):12193-8 (1993).
Silverman, The Organic Chemistry of Drug Design and Drug Action, pp. 352-401, San Diego, CA: Academic Press (1992).
Sly et al., Active site mutant transgene confers tolerance to human beta-glucuronidase without affecting the phenotype of MPS VII mice, Proc. Natl. Acad. Sci. USA, 98(5):2205-10 (2001).
Smith et al., Identification of common molecular subsequences, J. Mol. Biol., 147:195-7 (1981).
Smith et al., Structure and activity dependence of recombinant human insulin-like growth factor II on disulfide bond pairing, J. Biol. Chem., 264:9314-21 (1989).
Sohar et al., Mouse mutants lacking the cation-independent mannose 6-phosphate/insulin-like growth factor II receptor are impaired in lysosomal enzyme transport: comparison of cation-independent and cation-dependent mannose 6-phosphate receptor-deficient mice, Biochem. J., 330(Pt. 2):903-8 (1998).
Sojar et al., Characterization of rat ovarian lutropin receptor. Role of thiol groups in receptor association, J. Biol. Chem., 264:2552-9 (1989).
Sojar et al., Chemical deglycosylation of glycoproteins, Methods Enzymol., 138:341-50 (1987).
Soper et al., Enzyme replacement therapy improves reproductive performance in mucopolysaccharidosis type VII mice but does not prevent postnatal losses, Pediatr. Res., 45(2):180-6 (1999).
Souriau et al., Direct selection of EGF mutants displayed on filamentous phage using cells overexpressing EGF receptor, Biol. Chem., 380:451-8 (1999).
Sperr et al., Rituximab for the treatment of acquired antibodies to factor VIII, Haematologica, 92:66-71 (2007).
Spiro et al., Characterization of carbohydrate units of glycoproteins, Methods Enzymol., 8:44-9 (1966).
Spodsberg et al., Molecular basis of aberrant apical protein transport in an intestinal enzyme disorder, J. Biol. Chem., 276:23506-10 (2001).
Stahl et al., Evidence for specific recognition sites mediating clearance of lysosomal enzymes in vivo, Proc. Natl. Acad. Sci. USA, 73(11):4045-9 (1976).
Standley et al., The role of glycosylation in ionotropic glutamate receptor ligand binding, function, and trafficking, Cell Mol. Life Sci., 57(11):1508-16 (2000).
Stanley et al., Chinese hamster ovary cells selected for resistance to the cytotoxicity of phytohemagglutinin are deficient in a UDP-N-acetylglucosamine—glycoprotein N-acetylglucosaminyltransferase activity, Proc. Natl. Acad. Sci. USA, 72(9):3323-7 (1975).
Stanley et al., Selection and characterization of eight phenotypically distinct lines of lectin-resistant Chinese hamster ovary cell, Cell, 6(2):121-8 (1975).
Summary of the Boston IPA Board Meeting, Apr. 16-17, 2002, Association for Glycogen Storage Disease (UK) Bulletin, Issue 9, p. 14 (May 2002).
Supplementary European Search Report for EP 02725886 (2004).
Terasawa et al., Solution structure of human insulin-like growth factor II; recognition sites for receptors and binding proteins, EMBO J., 13(23):5590-7 (1994).
The Cytokine Facts Book, 2nd ed., pp. 301-305, Academic Press (2001).
Thim, A new family of growth factor-like peptides. 'Trefoil' disulphide loop structures as a common feature in breast cancer associated peptide (pS2), pancreatic spasmolytic polypeptide (PSP), and frog skin peptides (spasmolysins), FEBS Lett., 250(1):58-90 (1989).
Thorpe et al., Modification of the carbohydrate in ricin with metaperiodate-cyanoborohydride mixtures. Effects on toxicity and in vivo distribution, Eur. J. Biochem., 147(1):197-206 (1985).
Thotakura et al., Enzymatic deglycosylation of glycoproteins, Methods Enzymol., 138:350-9 (1987).
Thurberg et al., Characterization of pre- and post-treatment pathology after enzyme replacement therapy for Pompe disease, Lab Invest., 86(12):1208-20 (2006).
Timmermans et al., Characterization of pre- and post-treatment pathology after enzyme replacement therapy for Pompe disease, Pharmacol. Rev., 45(2):205-51 (1993).
Tong et al., The cation-independent mannose 6-phosphate receptor binds insulin-like growth factor II, J. Biol. Chem., 263(6):2585-8 (1988).
Torres et al., Solution structure of human insulin-like growth factor II. Relationship to receptor and binding protein interactions, J. Mol. Biol., 248:385-401 (1995).
Tschinke et al., The NEWLEAD program: a new method for the design of candidate structures from pharmacophoric hypotheses, J. Med. Chem., 36(24):3863-70 (1993).
Tsuji et al., Intracellular transport of acid alpha-glucosidase in human fibroblasts: evidence for involvement of phosphomannosyl receptor-independent system, J. Biochem., 104(2):276-8 (1988).
Tsuji et al., Lysosomal enzyme replacement using alpha 2-macroglobulin as a transport vehicle, J. Biochem., 115:937-44 (1994).
Tsuji et al., The precursor of acid α-glycosidase is synthesized as a membrane-bound enzyme, Biochem., Int., 15(5):945-52 (1987).
Ulmasov et al., Purification and kinetic analysis of recombinant CA XII, a membrane carbonic anhydrase overexpressed in certain cancers, Proc. Natl. Acad. Sci. USA, 97(26):14212-7 (2000).
Urayama et al., Developmentally regulated mannose 6-phosphate receptor-mediated transport of a lysosomal enzyme across the blood-brain barrier, Proc. Natl. Acad. Sci. USA, 101(34):12658-63 (2004).
Urlaub et al., Isolation of Chinese hamster cell mutants deficient in dihydrofolate reductase activity, Proc. Natl. Acad. Sci. USA, 77(7):4216-20 (1980).
Vaccaro, Karen, email dated Feb. 20, 2002.
Valenzano et al., Biophysical and biological properties of naturally occurring high molecular weight insulin-like growth factor II variants, J. Biol. Chem., 272(8):4804-13 (1997).
Valenzano et al., Soluble insulin-like growth factor II/mannose 6-phosphate receptor carries multiple high molecular weight forms of insulin-like growth factor II in fetal bovine serum, J. Biol. Chem., 270(27):16441-8 (1995).
Van den Hout et al., Enzyme therapy for pompe disease with recombinant human alpha-glucosidase from rabbit milk, J. Inherit Metab. Dis., 24:266-74 (2001).
Van den Hout et al., Recombinant human alpha-glucosidase from rabbit milk in Pompe patients, Lancet, 356(9227):397-8 (2000).
Van der Ploeg et al., Intravenous administration of phosphorylated acid alpha-glucosidase leads to uptake of enzyme in heart and skeletal muscle of mice, J. Clin. Invest., 87(2):513-8 (1991).
Van Doorn et al., Antibodies directed against the E region of pro-insulin-like growth factor-II used to evaluate non-islet cell tumor-induced hypoglycemia, Clin. Chem., 48(10):1739-50 (2002).
Van Hove et al., High-level production of recombinant human lysosomal acid alpha-glucosidase in Chinese hamster ovary cells which targets to heart muscle and corrects glycogen accumulation in fibroblasts from patients with Pompe disease, Proc. Natl. Acad. Sci. USA, 93(1):65-70 (1996).
Vogler et al., A murine model of mucopolysaccharidosis VII. Gross and microscopic findings in beta-glucuronidase-deficient mice, Am. J. Pathol., 136(1):207-17 (1990).
Vogler et al., Enzyme replacement with recombinant beta-glucuronidase in the newborn mucopolysaccharidosis type VII mouse, Pediatr. Res., 34(6):837-40 (1993).
Vogler et al., Overcoming the blood-brain barrier with high-dose enzyme replacement therapy in murine mucopolysaccharidosis VII, Proc. Natl. Acad. Sci. USA, 102(41):14777-82 (2005).
Vyas et al., Ligand-receptor-mediated drug delivery: an emerging paradigm in cellular drug targeting, Crit. Rev. Ther. Drug Carrier Syst., 18(1):1-76 (2001).

(56) References Cited

OTHER PUBLICATIONS

Wadensten et al., Purification and characterization of recombinant human insulin-like growth factor II (IGF-II) expressed as a secreted fusion protein in *Escherichia coli*, Biotechnol. Appl. Biochem., 13(3):412-21 (1991).

Waheed et al., Human lysosomal acid phosphatase is transported as a transmembrane protein to lysosomes in transfected baby hamster kidney cells, EMBO J., 7(8):2351-8 (1988).

Waheed et al., Regulation of transferrin-mediated iron uptake by HFE, the protein defective in hereditary hemochromatosis, Proc. Natl. Acad. Sci. USA, 99(5):3117-22 (2002).

Wang et al., A study of protein-protein interactions in living cells using luminescence resonance energy transfer (LRET) from *Renilla luciferase* to Aequorea GFP, Mol. Gen. Genet., 264(5):578-87 (2001).

Wang et al., Regulation of embryonic growth and lysosomal targeting by the imprinted Igf2/Mpr gene, Nature, 372(6505):464-7 (1994).

Wang et al., The insulin A and B chains contain sufficient structural information to form the native molecule, Trends Biochem. Sci., 16(8):279-81 (1991).

Waszkowycz et al., PRO_LIGAND: an approach to de novo molecular design. 2. Design of novel molecules from molecular field analysis (MFA) models and pharmacophores, J. Med. Chem., 37(23):3994-4002 (1994).

Wells et al., Importance of hydrogen-bond formation in stabilizing the transition state of subtilisin. *Philos. Trans. R. Soc. London*, A:317:415-23 (1986).

Wilczak et al., Insulin-like growth factor system in serum and cerebrospinal fluid in patients with multiple sclerosis, Neurosci. Lett., 257(3):168-70 (1998).

Williams et al., Enzyme replacement in Pompe disease with an alpha-glucosidase-low density lipoprotein complex, Birth Defects Orig. Artic. Ser., 16(1):415-23 (1980).

Willingham et al., The receptosome: an intermediate organelle of receptor mediated endocytosis in cultured fibroblasts, Cell, 21(1):67-77 (1980).

Wisselaar et al., Structural and functional changes of lysosomal acid alpha-glucosidase during intracellular transport and maturation, J. Biol. Chem., 268(3):2223-31 (1993).

Wolfe et al., Murine Mucopolysaccharidosis type VII: a model system for somatic gene therapy of the central nervous system, chapter 20 (pp. 263-274) In: Lowenstein et al. (eds.), Protocols for Gene Transfer in Neuroscience: Towards Gene Therapy of Neurological Disorders, John Wiley & Sons Ltd. (1996).

Written Opinion for PCT/US2005/004286 (2005).

Written Opinion for PCT/US2007/023881 (2009).

Yamashiro et al., Acidification of endocytic compartments and the intracellular pathways of ligands and receptors, J. Cell. Biochem., 26:231-46 (1984).

Yang et al., Probing the folding pathways of long R(3) insulin-like growth factor-I (LR(3)IGF-I) and IGF-I via capture and identification of disulfide intermediates by cyanylation methodology and mass spectrometry, J. Biol. Chem., 274(53):37598-604 (1999).

York et al., The rate of internalization of the mannose 6-phosphate/insulin-like growth factor II receptor is enhanced by multivalent ligand binding, J. Biol. Chem., 274(2):1164-71 (1999).

Yu et al., Insulin-like growth factors (IGF-I, free IGF-I and IGF-II) and insulin-like growth factor binding proteins (IGFBP-2, IGFBP-3, IGFBP-6, and ALS) in blood circulation, J. Clin. Lab Anal., 13(4):166-72 (1999).

Zarn et al., A mutant of human insulin-like growth factor II (IGF II) with the processing sites of proinsulin. Expression and binding studies of processed IGF II, Eur. J. Biochem., 210(3):665-9 (1992).

Zhu et al., Carbohydrate-remodelled acid alpha-glucosidase with higher affinity for the cation-independent mannose 6-phosphate receptor demonstrates improved delivery to muscles of Pompe mice, Biochem. J., 389 (Pt. 3):619-28 (2005).

Zhu et al., Conjugation of mannose 6-phosphate-containing oligosaccharides to acid alpha-glucosidase improves the clearance of glycogen in pompe mice, J. Biol. Chem., 279(48):50336-41 (2004).

Zoller et al., Oligonucleotide-directed mutagenesis using M13-derived vectors: an efficient and general procedure for the production of point mutations in any fragment of DNA, Nucleic Acids Res., 10(20):6487-500 (1982).

Zubieta et al., Response: Measuring our natural painkiller, Trends Neurosci., 25(2):69 (2002).

\* cited by examiner

Lane 1: Mark 12 Standard
Lane 2: Ref Std NR
Lane 3: C6GT NR 4°C
Lane 4: C6MT NR 4°C
Lane 5: PC6MT NR 4°C
Lane 6: C6GT NR 25°C
Lane 7: C6MT NR 25°C
Lane 8: PC6MT NR 25°C
Lane 9: Ref Std R
Lane 10: C6GT R 4°C
Lane 11: C6MT R 4°C
Lane 12: PC6MT R 4°C
Lane 13: C6GT R 25°C
Lane 14: C6MT R 25°C
Lane 15: PC6MT R 25°C

SEQUENCE LISTING

```
<160> NUMBER OF SEQ ID NOS: 6

<210> SEQ ID NO 1
<211> LENGTH: 67
<212> TYPE: PRT
<213> ORGANISM: Homo sapiens

<400> SEQUENCE: 1
```

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 2
<211> LENGTH: 947
<212> TYPE: PRT
<213> ORGANISM: Artificial Sequence
<220> FEATURE:
<223> OTHER INFORMATION: ZC-701 sequence

<400> SEQUENCE: 2

Ala Leu Cys Gly Gly Glu Leu Val Asp Thr Leu Gln Phe Val Cys Gly
1               5                   10                  15

Asp Arg Gly Phe Tyr Phe Ser Arg Pro Ala Ser Arg Val Ser Arg Arg
            20                  25                  30

Ser Arg Gly Ile Val Glu Glu Cys Cys Phe Arg Ser Cys Asp Leu Ala
        35                  40                  45

Leu Leu Glu Thr Tyr Cys Ala Thr Pro Ala Lys Ser Glu Gly Ala Pro
    50                  55                  60

Ala His Pro Gly Arg Pro Arg Ala Val Pro Thr Gln Cys Asp Val Pro
65                  70                  75                  80

Pro Asn Ser Arg Phe Asp Cys Ala Pro Asp Lys Ala Ile Thr Gln Glu
                85                  90                  95

Gln Cys Glu Ala Arg Gly Cys Cys Tyr Ile Pro Ala Lys Gln Gly Leu
            100                 105                 110

Gln Gly Ala Gln Met Gly Gln Pro Trp Cys Phe Phe Pro Pro Ser Tyr
        115                 120                 125

Pro Ser Tyr Lys Leu Glu Asn Leu Ser Ser Ser Glu Met Gly Tyr Thr
    130                 135                 140

Ala Thr Leu Thr Arg Thr Thr Pro Thr Phe Phe Pro Lys Asp Ile Leu
145                 150                 155                 160

Thr Leu Arg Leu Asp Val Met Met Glu Thr Glu Asn Arg Leu His Phe
                165                 170                 175

Thr Ile Lys Asp Pro Ala Asn Arg Arg Tyr Glu Val Pro Leu Glu Thr
            180                 185                 190

Pro Arg Val His Ser Arg Ala Pro Ser Pro Leu Tyr Ser Val Glu Phe
        195                 200                 205

Ser Glu Glu Pro Phe Gly Val Ile Val His Arg Gln Leu Asp Gly Arg
    210                 215                 220

Val Leu Leu Asn Thr Thr Val Ala Pro Leu Phe Phe Ala Asp Gln Phe
225                 230                 235                 240

Leu Gln Leu Ser Thr Ser Leu Pro Ser Gln Tyr Ile Thr Gly Leu Ala
                245                 250                 255

Glu His Leu Ser Pro Leu Met Leu Ser Thr Ser Trp Thr Arg Ile Thr
            260                 265                 270

Leu Trp Asn Arg Asp Leu Ala Pro Thr Pro Gly Ala Asn Leu Tyr Gly
        275                 280                 285

-continued

```
Ser His Pro Phe Tyr Leu Ala Leu Glu Asp Gly Gly Ser Ala His Gly
    290                 295                 300

Val Phe Leu Leu Asn Ser Asn Ala Met Asp Val Val Leu Gln Pro Ser
305                 310                 315                 320

Pro Ala Leu Ser Trp Arg Ser Thr Gly Gly Ile Leu Asp Val Tyr Ile
                325                 330                 335

Phe Leu Gly Pro Glu Pro Lys Ser Val Val Gln Gln Tyr Leu Asp Val
            340                 345                 350

Val Gly Tyr Pro Phe Met Pro Pro Tyr Trp Gly Leu Gly Phe His Leu
        355                 360                 365

Cys Arg Trp Gly Tyr Ser Ser Thr Ala Ile Thr Arg Gln Val Val Glu
370                 375                 380

Asn Met Thr Arg Ala His Phe Pro Leu Asp Val Gln Trp Asn Asp Leu
385                 390                 395                 400

Asp Tyr Met Asp Ser Arg Arg Asp Phe Thr Phe Asn Lys Asp Gly Phe
                405                 410                 415

Arg Asp Phe Pro Ala Met Val Gln Glu Leu His Gln Gly Gly Arg Arg
            420                 425                 430

Tyr Met Met Ile Val Asp Pro Ala Ile Ser Ser Ser Gly Pro Ala Gly
        435                 440                 445

Ser Tyr Arg Pro Tyr Asp Glu Gly Leu Arg Arg Gly Val Phe Ile Thr
    450                 455                 460

Asn Glu Thr Gly Gln Pro Leu Ile Gly Lys Val Trp Pro Gly Ser Thr
465                 470                 475                 480

Ala Phe Pro Asp Phe Thr Asn Pro Thr Ala Leu Ala Trp Trp Glu Asp
                485                 490                 495

Met Val Ala Glu Phe His Asp Gln Val Pro Phe Asp Gly Met Trp Ile
            500                 505                 510

Asp Met Asn Glu Pro Ser Asn Phe Ile Arg Gly Ser Glu Asp Gly Cys
        515                 520                 525

Pro Asn Asn Glu Leu Glu Asn Pro Pro Tyr Val Pro Gly Val Val Gly
    530                 535                 540

Gly Thr Leu Gln Ala Ala Thr Ile Cys Ala Ser Ser His Gln Phe Leu
545                 550                 555                 560

Ser Thr His Tyr Asn Leu His Asn Leu Tyr Gly Leu Thr Glu Ala Ile
                565                 570                 575

Ala Ser His Arg Ala Leu Val Lys Ala Arg Gly Thr Arg Pro Phe Val
            580                 585                 590

Ile Ser Arg Ser Thr Phe Ala Gly His Gly Arg Tyr Ala Gly His Trp
        595                 600                 605

Thr Gly Asp Val Trp Ser Ser Trp Glu Gln Leu Ala Ser Ser Val Pro
    610                 615                 620

Glu Ile Leu Gln Phe Asn Leu Leu Gly Val Pro Leu Val Gly Ala Asp
625                 630                 635                 640

Val Cys Gly Phe Leu Gly Asn Thr Ser Glu Glu Leu Cys Val Arg Trp
                645                 650                 655

Thr Gln Leu Gly Ala Phe Tyr Pro Phe Met Arg Asn His Asn Ser Leu
            660                 665                 670

Leu Ser Leu Pro Gln Glu Pro Tyr Ser Phe Ser Glu Pro Ala Gln Gln
        675                 680                 685

Ala Met Arg Lys Ala Leu Thr Leu Arg Tyr Ala Leu Leu Pro His Leu
    690                 695                 700

Tyr Thr Leu Phe His Gln Ala His Val Ala Gly Glu Thr Val Ala Arg
```

705                 710                 715                 720

Pro Leu Phe Leu Glu Phe Pro Lys Asp Ser Ser Thr Trp Thr Val Asp
                        725                 730                 735

His Gln Leu Leu Trp Gly Glu Ala Leu Leu Ile Thr Pro Val Leu Gln
                        740                 745                 750

Ala Gly Lys Ala Glu Val Thr Gly Tyr Phe Pro Leu Gly Thr Trp Tyr
                        755                 760                 765

Asp Leu Gln Thr Val Pro Ile Glu Ala Leu Gly Ser Leu Pro Pro Pro
                        770                 775                 780

Pro Ala Ala Pro Arg Glu Pro Ala Ile His Ser Glu Gly Gln Trp Val
        785                 790                 795                 800

Thr Leu Pro Ala Pro Leu Asp Thr Ile Asn Val His Leu Arg Ala Gly
                        805                 810                 815

Tyr Ile Ile Pro Leu Gln Gly Pro Gly Leu Thr Thr Thr Glu Ser Arg
                        820                 825                 830

Gln Gln Pro Met Ala Leu Ala Val Ala Leu Thr Lys Gly Gly Glu Ala
                        835                 840                 845

Arg Gly Glu Leu Phe Trp Asp Asp Gly Glu Ser Leu Glu Val Leu Glu
                        850                 855                 860

Arg Gly Ala Tyr Thr Gln Val Ile Phe Leu Ala Arg Asn Asn Thr Ile
        865                 870                 875                 880

Val Asn Glu Leu Val Arg Val Thr Ser Glu Gly Ala Gly Leu Gln Leu
                        885                 890                 895

Gln Lys Val Thr Val Leu Gly Val Ala Thr Ala Pro Gln Gln Val Leu
                        900                 905                 910

Ser Asn Gly Val Pro Val Ser Asn Phe Thr Tyr Ser Pro Asp Thr Lys
                        915                 920                 925

Val Leu Asp Ile Cys Val Ser Leu Leu Met Gly Glu Gln Phe Leu Val
                        930                 935                 940

Ser Trp Cys
        945

<210> SEQ ID NO 3
<211> LENGTH: 3
<212> TYPE: PRT
<213> ORGANISM: Artificial Sequence
<220> FEATURE:
<223> OTHER INFORMATION: Spacer sequence

<400> SEQUENCE: 3

Gly Ala Pro
1

<210> SEQ ID NO 4
<211> LENGTH: 6
<212> TYPE: PRT
<213> ORGANISM: Artificial Sequence
<220> FEATURE:
<223> OTHER INFORMATION: Spacer sequence

<400> SEQUENCE: 4

Gly Gly Gly Gly Gly Pro
1               5

<210> SEQ ID NO 5
<211> LENGTH: 4
<212> TYPE: PRT
<213> ORGANISM: Artificial Sequence
<220> FEATURE:

```
<223> OTHER INFORMATION: Furin cleavage site
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

Arg Xaa Xaa Arg
1

<210> SEQ ID NO 6
<211> LENGTH: 6
<212> TYPE: PRT
<213> ORGANISM: Artificial Sequence
<220> FEATURE:
<223> OTHER INFORMATION: Furin cleavage site
<220> FEATURE:
<221> NAME/KEY: MISC_FEATURE
<222> LOCATION: (1)..(1)
<223> OTHER INFORMATION: X = Lys or Arg
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: X = Lys or Arg

<400> SEQUENCE: 6

Xaa Xaa Xaa Xaa Xaa Arg
1               5
```

US 8,785,168 B2

FORMULATIONS FOR LYSOSOMAL ENZYMES

CROSS REFERENCE TO RELATED APPLICATIONS

This application claims priority to U.S. Provisional Patent Application Ser. No. 61/187,747, filed on Jun. 17, 2009; the entirety of which is hereby incorporated by reference.

BACKGROUND

More than forty lysosomal storage diseases (LSDs) are caused, directly or indirectly, by the absence of one or more lysosomal enzymes in the lysosome. Enzyme replacement therapy for LSDs is being actively pursued. Therapy generally requires that LSD proteins be taken up and delivered to the lysosomes of a variety of cell types. The inventors of the present application have previously developed a peptide-based targeting technology that allows more efficient delivery of therapeutic enzymes to the lysosomes. This proprietary technology is termed Glycosylation Independent Lysosomal Targeting (GILT). Details of the GILT technology are described in U.S. Pat. Nos. 7,396,811, 7,560,424, and 7,629,309; U.S. Application Publication Nos. 2003-0082176, 2004-0006008, 2003-0072761, 2005-0281805, 2005-0244400, and international publications WO 03/032913, WO 03/032727, WO 02/087510, WO 03/102583, WO 2005/078077, the disclosures of all of which are hereby incorporated by reference.

Because proteins utilized in enzyme replacement therapy are larger and more complex than traditional organic and inorganic drugs (i.e., possessing multiple functional groups in addition to complex three-dimensional structures), the formulation, packaging and preservation of such proteins poses special problems.

SUMMARY OF THE INVENTION

The present invention provides improved formulations for lysosomal enzymes useful for enzyme replacement therapy. Among other things, the present invention provides formulations that preserve or enhance the stability and/or efficacy of a lysosomal enzyme such as acid alpha-glucosidase.

In one aspect, the present invention provides a pharmaceutical composition for treating Pompe disease comprising an acid alpha-glucosidase and a poloxamer. In some embodiments, the poloxamer suitable for the invention is Pluronic® F-68. In some embodiments, the poloxamer is at a concentration ranging between approximately 0.001% and approximately 0.2%. In certain embodiments, the poloxamer is at a concentration of approximately 0.1%. In certain embodiments, the poloxamer is at a concentration of approximately 0.05%.

In some embodiments, a pharmaceutical composition according to the invention further includes a buffering agent. In some embodiments, the buffering agent is selected from the group consisting of histidine, sodium acetate, citrate, phosphate, succinate, Tris and combinations thereof. In certain embodiments, the buffering agent is at a concentration ranging between approximately 25 mM and approximately 50 mM.

In some embodiments, a pharmaceutical composition according to the invention further includes a stabilizing agent. In some embodiments, the stabilizing agent is selected from the group consisting of sucrose, arginine, sorbitol, mannitol, glycine, trehalose and combinations thereof.

In some embodiments, a pharmaceutical composition according to the invention further includes a tonicity modifier. In some embodiments, the tonicity modifier is selected from the group consisting of glycine, sorbitol, sucrose, mannitol, sodium chloride, dextrose, arginine and combinations thereof.

In some embodiments, a pharmaceutical composition according to the invention includes a bulking agent. In some embodiments, the bulking agent is selected from the group consisting of sucrose, mannitol, glycine, sodium chloride, dextran, trehalose and combinations thereof.

In some embodiments, a pharmaceutical composition according to the invention has a pH ranging from approximately 4.0 to approximately 7.0. In certain embodiments, a suitable pH is approximately 6.0.

In some embodiments, a pharmaceutical composition according to the invention is in a form suitable for parenteral administration. In some embodiments, a pharmaceutical composition according to the invention is in a form suitable for intravenous infusion.

In some embodiments, a pharmaceutical composition according to the invention is a lyophilized mixture.

In some embodiments, the acid alpha-glucosidase in a formulation is a recombinant human acid alpha-glucosidase (GAA). In certain embodiments, the recombinant human GAA is produced from CHO cells. In some embodiments, the recombinant human GAA has modified glycosylation levels (e.g., increased or reduced) as compared to naturally-occurring human GAA. In some embodiments, the recombinant human GAA contains increased numbers of mannose-6-phosphate residues as compared to naturally-occurring human GAA. In some embodiments, the recombinant human GAA contains reduced numbers of mannose-6-phosphate residues as compared to naturally-occurring human GAA. In some embodiments, the recombinant human GAA used in a formulation is underglycosylated or deglycosylated.

In some embodiments, the acid alpha-glucosidase is a fusion protein comprising human GAA or a functional variant thereof. In some embodiments, the fusion protein further comprises a lysosomal targeting peptide. In some embodiments, the lysosomal targeting peptide has an amino acid sequence at least 70% (e.g., at least 75%, 80%, 85%, 90%, 95%, 98%, or 99%) identical to mature human IGF-II (SEQ ID NO:1).

In some embodiments, the lysosomal targeting peptide is an IGF-II mutein and comprises a mutation within a region corresponding to amino acids 34-40 of SEQ ID NO:1 such that the mutation abolishes at least one furin protease cleavage site. In some embodiments, the lysosomal targeting peptide is an IGF-II mutein that has diminished binding affinity for the IGF-I receptor relative to the affinity of naturally-occurring human IGF-II for the IGF-I receptor. In some embodiments, the lysosomal targeting peptide is an IGF-II mutein that has diminished binding affinity for the insulin receptor relative to the affinity of naturally-occurring human IGF-II for the insulin receptor.

In some embodiments, the fusion protein comprises an amino acid sequence of SEQ ID NO:2. In some embodiments, the fusion protein comprises an amino acid sequence at least 70% (e.g., at least 75%, 80%, 85%, 90%, 95%, 98%, or 99%) identical to SEQ ID NO:2.

In some embodiments, the present invention provides a pharmaceutical composition comprising an acid alpha-glucosidase described herein in a formulation containing approximately 50 mM sodium citrate, 4% mannitol, 1% trehalose, and 0.1% Pluronic F-68. In some embodiments, the present invention provides a pharmaceutical composition comprising an acid alpha-glucosidase described herein in a formulation containing approximately 25 mM sodium citrate, 2% mannitol, 0.5% trehalose, and 0.05% Pluronic F-68. In various embodiments, a formulation according to the invention is in a liquid form. In various embodiments, a formulation according to the invention has a pH ranging approximately between 5-7 (e.g., a pH of approximately 5.0, 5.5, 6.0, 6.5, 6.6, 6.7, 6.8, 6.9, or 7.0). In some embodiments, the present invention provides a pharmaceutical composition comprising a lyophilized mixture of an acid alpha-glucosidase described herein, sodium citrate, mannitol, trehalose, and Pluronic F-68.

The present invention further provides methods of treating Pompe disease and other lysosomal storage diseases by administering to a subject in need of treatment a pharmaceutical composition described herein.

As used in this application, the terms "about" and "approximately" are used as equivalents. Any numerals used in this application with or without about/approximately are meant to cover any normal fluctuations appreciated by one of ordinary skill in the relevant art. For example, normal fluctuations of a value of interest may include a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes not for limitation.

DEFINITIONS

Figure 1:
FIG. 1 depicts exemplary results from surfactant screening studies. Vials are shown after agitation with and without surfactants.

In order for the present invention to be more readily understood, certain terms are first defined below. Additional definitions for the following terms and other terms are set forth throughout the specification.

Bulking agent: As used herein, the term "bulking agent" refers to a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine, sodium chloride, hydroxyethyl starch, lactose, sucrose, trehalose, polyethylene glycol and dextran.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by infusing into the bloodstream. As the blood perfuses patient tissues, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in tissues where the storage defect is manifest. In some embodiments, lysosomal enzyme replacement therapeutics are delivered using carbohydrates naturally attached to the protein to engage specific receptors on the surface of the target cells. One receptor, the cation-independent M6P receptor (CI-MPR), is particularly useful for targeting replacement lysosomal enzymes because the CI-MPR is present on the surface of most cell types. Such enzyme replacement therapies, and replacement enzymes are described in U.S. Pat. Nos. 7,371,366, 7,354,576, 7,067,127, 6,905,856, 6,861,242, 6,828,135, 6,800,472, 6,770,468, 6,670,165, 6,642,038, 6,569,661, 6,537,785, 6,534,300 and U.S. Patent Application Publication numbers 20080176285, 20080003626, 20060286087, 20050170449, 20050003486. In some embodiments, lysosomal enzyme replacement therapeutics are delivered in a glycosylation independent manner, in particular, in a mannose-6-phosphate-independent manner. Such delivery method is also known as glycosylation-independent lysosomal targeting (GILT). In some embodiments, replacement enzymes contain a GILT tag (e.g., a peptide) that binds to the CI-MPR in a mannose-6-phosphate-independent manner. Details of the GILT technology are described in U.S. Pat. No. 7,396,811, U.S. Application Publication Nos. 2003-0082176, 2004-0006008, 2003-0072761, 2005-0281805, 2005-0244400, and international publications WO 03/032913, WO 03/032727, WO 02/087510, WO 03/102583, WO 2005/078077, the disclosures of all of which are hereby incorporated by reference.

Glycosylation Independent Lysosomal Targeting: As used herein, the term "glycosylation independent lysosomal targeting" (also referred to as "GILT") refer to lysosomal targeting that is mannose-6-phosphate-independent.

Human acid alpha-glucosidase: As used herein, the term "human acid alpha-glucosidase" (also referred to as "GAA") refers to precursor wild-type form of human GAA or a functional variant that is capable of reducing glycogen levels in mammalian lysosomes or that can rescue or ameliorate one or more Pompe disease symptoms.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease (e.g., Pompe disease) as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a lysosomal storage disease, for example, Pompe disease (i.e., either infantile-, juvenile-, or adult-onset Pompe disease) or having the potential to develop a lysosomal storage disease (e.g., Pompe disease).

Lyoprotectant: As used herein, the term "lyoprotectant" refers to a molecule that prevents or reduces chemical and/or physical instability of a protein or other substance upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate: a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. In some embodiments, a lyoprotectant is a non-reducing sugar, such as trehalose or sucrose.

Lysosomal storage diseases: As used herein, "lysosomal storage diseases" refer to a group of genetic disorders that result from deficiency in at least one of the enzymes (e.g., acid hydrolases) that are required to break macromolecules down to peptides, amino acids, monosaccharides, nucleic acids and fatty acids in lysosomes. As a result, individuals suffering from lysosomal storage diseases have accumulated materials in lysosomes. Exemplary lysosomal storage diseases are listed in Table 1.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 1.

Preservative: As used herein, the term "preservative" refers to a compound which can be added to the diluent to reduce bacterial action in the reconstituted formulation, thus facilitating the production of a multi-use reconstituted formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechoi, resorcinol, cyclohexanol. 3-pentanol, and m-cresol. The most preferred preservative herein is benzyl alcohol.

Spacer: As used herein, the term "spacer" (also referred to as "linker") refers to a peptide sequence between two protein moieties in a fusion protein. A spacer is generally designed to be flexible or to interpose a structure, such as an alpha-helix, between the two protein moieties. A spacer can be relatively short, such as the sequence Gly-Ala-Pro (SEQ ID NO:3) or Gly-Gly-Gly-Gly-Gly-Pro (SEQ ID NO:4), or can be longer, such as, for example, 10-25 amino acids in length.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Therapeutically effective amount: As used herein, the term "therapeutically effective amount" refers to an amount of a therapeutic protein (e.g., a lysosomal enzyme) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein (e.g., a lysosomal enzyme) or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

Treatment: As used herein, the term "treatment" (also "treat" or "treating") refers to any administration of a therapeutic protein (e.g., a lysosomal enzyme) that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. For example, treatment can refer to improvement of cardiac status (e.g., increase of end-diastolic and/or end-systolic volumes, or reduction, amelioration or prevention of the progressive cardiomyopathy that is typically found in Pompe disease) or of pulmonary function (e.g., increase in crying vital capacity over baseline capacity, and/or normalization of oxygen desaturation during crying); improvement in neurodevelopment and/or motor skills (e.g., increase in AIMS score); reduction of glycogen levels in tissue of the individual affected by the disease; or any combination of these effects. In some embodiments, treatment includes improvement of glycogen clearance, particularly in reduction or prevention of Pompe disease-associated cardiomyopathy.

DETAILED DESCRIPTION OF THE INVENTION

The present invention provides, among other things, formulations for lysosomal enzymes suitable for enzyme replacement therapy that preserve or enhance protein stability and/or efficacy. In particular, formulations provided by the present invention reduce or eliminate formation of high molecule weight aggregates, protein degradation during freeze-drying, storage, shipping and infusion.

Prior to the present invention, filter clogging resulted from enzyme precipitation during infusion is a long-standing problem for existing formulations for certain lysosomal enzymes (in particular, recombinant human α-glucosidase (GAA)). It was reported that sometimes filters was blocked up multiple times during one infusion. This problem not only causes great inconvenience to patients and physicians, but also effects therapeutic efficacy and patient safety. The present invention is, in part, based on the surprising discovery that the use of a particular type of surfactant, poloxamer, in a formulation significantly reduced or eliminated enzyme precipitation during infusion. As described in the Examples section, formulations containing a poloxamer also stabilize lysosomal enzymes during lyophilization, reconstitution, storage and patient infusion. Thus, the present invention represents a significant improvement in the field of enzyme therapeutic therapy.

Various aspects of the invention are described in detail in the following sections. The use of sections is not meant to limit the invention. Each section can apply to any aspect of the invention. In this application, the use of "or" means "and/or" unless stated otherwise.

Lysosomal Enzymes

The present invention can be utilized to formulate any lysosomal enzymes. Suitable lysosomal enzymes include any enzyme that is capable of reducing accumulated materials in mammalian lysosomes or that can rescue or ameliorate one or more lysosomal storage disease symptoms. Suitable lysosomal enzymes include both wild-type or modified lysosomal enzymes and can be produced using recombinant or synthetic methods or purified from nature sources. Exemplary lysosomal enzymes are listed in Table 1.

TABLE 1

Lysosomal Storage Diseases and associated enzyme defects

| Disease Name | Enzyme Defect | Substance Stored |
|---|---|---|
| A. Glycogenosis Disorders | | |
| Pompe Disease | Acid-α1,4-Glucosidase | Glycogen α1-4 linked Oligosaccharides |
| B. Glycolipidosis Disorders | | |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| C. Mucopolysaccharide Disorders | | |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio A (MPS IVA) | Galactosamine-6-Sulfatase | Keratan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| D. Oligosaccharide/Glycoprotein Disorders | | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| E. Lysosomal Enzyme Transport Disorders | | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| F. Lysosomal Membrane Transport Disorders | | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| G. Other | | |
| Batten Disease (Juvenile Neuronal Ceroid Lipofuscinosis) | Unknown | Lipofuscins |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

The amino acid sequences of the enzymes shown in Table 1 are well known in the art and are readily accessible by searching in public databases such as GenBank using enzyme names and such sequences are incorporated herein by reference. In some embodiments, the present invention can also be used to formulate enzymes modified from naturally-occurring enzymes including, but not limited to, any enzymes having a sequence at least 50%, 55%, 60%, 65%, 70%, 75%, 80%, 85%, 90%, 95%, 98%, or 99% identical to the sequence of corresponding naturally-occurring enzyme shown in Table 1. In some embodiments, a suitable enzyme can be a fragment of a naturally-occurring enzyme. In some embodiments, a suitable enzyme can be a fusion protein containing a naturally-occurring enzyme or a fragment thereof. In various embodiments, a modified enzyme retains the enzymatic activity of the corresponding naturally-occurring enzyme. For example, a suitable GAA enzyme can be a fragment of naturally-occurring human GAA or a sequence variant thereof which retains the ability to cleave α1-4 linkages in linear oligosaccharides.

"Percent (%) amino acid sequence identity" with respect to the lysosomal enzyme sequences is defined as the percentage of amino acid residues in a candidate sequence that are identical with the amino acid residues in the naturally-occurring human enzyme sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

GILT-Tagged Lysosomal Enzymes

In some embodiments, a suitable enzyme is modified to facilitate lysosomal targeting. For example, a suitable enzyme may be fused to a Glycosylation Independent Lysosomal Targeting (GILT) tag, which targets the enzyme to lysosomes in a mannose-6-phosphate-independent manner. Typically, a GILT tag is a protein, peptide, or other moiety that binds the CI-MPR, which is also referred to as IGF-II receptor, in a mannose-6-phosphate-independent manner.

In some embodiments, a GILT tag is derived from human insulin-like growth factor II (IGF-II). In some embodiments, a GILT tag is a wild-type or naturally-occurring mature human IGF-II (SEQ ID NO:1).

```
Mature human IGF-II (SEQ ID NO: 1) (furin cleavage
sites are bolded and underlined)
AYRPSETLCGGELVDTLQFVCGDRGFYFSRPASRVSRRSRGIVEECCFR

SCDLALLETYCATPAKSE
```

In some embodiments, a GILT tag is a modified mature human IGF-II containing amino acid substitutions, insertions or deletions. In some embodiments, a GILT tag has a sequence at least 50%, 55%, 60%, 65%, 70%, 75%, 80%, 85%, 90%, 95%, 98%, or 99% identical to the sequence of mature human IGF-II (SEQ ID NO:1). In some embodiments, a GILT tag is a fragment of mature human IGF-II. In particular embodiments, a GILT tag contains amino acids 8-67 of mature human IGF-II (SEQ ID NO:1). In some embodiments, a GILT tag contains a N-terminal, C-terminal or internal deletion. In particular embodiments, a GILT tag contains a deletion of amino acids 2-7 (Δ2-7) of mature human IGF-II (SEQ ID NO:1). In some embodiments, a GILT tag is a modified human IGF-II peptide that has diminished binding affinity for the IGF-I receptor as compared to the naturally-occurring human IGF-II.

In some embodiments, a GILT tag is a furin-resistant peptide tag. Furin protease typically recognizes and cleaves a cleavage site having a consensus sequence Arg-X-X-Arg (SEQ ID NO:5), X is any amino acid. The cleavage site is positioned after the carboxy-terminal arginine (Arg) residue in the sequence. In some embodiments, a furin cleavage site has a consensus sequence Lys/Arg-X-X-X-Lys/Arg-Arg (SEQ ID NO:6), X is any amino acid. The cleavage site is positioned after the carboxy-terminal arginine (Arg) residue in the sequence. As used herein, the term "furin" refers to any protease that can recognize and cleave the furin protease cleavage site as defined herein, including furin or furin-like protease. Furin is also known as paired basic amino acid cleaving enzyme (PACE). Furin belongs to the subtilisin-like proprotein convertase family that includes PC3, a protease responsible for maturation of proinsulin in pancreatic islet cells. The gene encoding furin was known as FUR (FES Upstream Region).

As shown in SEQ ID NO:1, the mature human IGF-II contains two potential overlapping furin cleavage sites between residues 34-40 (bolded and underlined).

In some embodiments, a suitable GILT tag is a modified IGF-II peptide that is resistant to cleavage by furin and still retain ability to bind to the CI-MPR in a mannose-6-phosphate-independent manner. In some embodiments, furin-resistant GILT tags can be designed by mutating the amino acid sequence at one or more furin cleavage sites such that the mutation abolishes at least one furin cleavage site. Thus, in some embodiments, a furin-resistant GILT tag is a furin-resistant IGF-II mutein containing a mutation that abolishes at least one furin protease cleavage site or changes a sequence adjacent to the furin protease cleavage site such that the furin cleavage is prevented, inhibited, reduced or slowed down as compared to a wild-type IGF-II peptide (e.g., wild-type human mature IGF-II). Typically, a suitable mutation does not impact the ability of the furin-resistant GILT tag to bind to the human cation-independent mannose-6-phosphate receptor. In particular, a furin-resistant IGF-II mutein suitable for the invention binds to the human cation-independent mannose-6-phosphate receptor in a mannose-6-phosphate-independent manner with a dissociation constant of $10^{-7}$ M or less (e.g., $10^{-8}$, $10^{-9}$, $10^{-10}$, $10^{-11}$, or less) at pH 7.4. In some embodiments, a furin-resistant IGF-II mutein contains a mutation within a region corresponding to amino acids 30-40 (e.g., 31-40, 32-40, 33-40, 34-40, 30-39, 31-39, 32-39, 34-37, 32-39, 33-39, 34-39, 35-39, 36-39, 37-40, 34-40) of SEQ ID NO:1. In some embodiments, a suitable mutation abolishes at least one furin protease cleavage site. A mutation can be amino acid substitutions, deletions, insertions. For example, any one amino acid within the region corresponding to residues 30-40 (e.g., 31-40, 32-40, 33-40, 34-40, 30-39, 31-39, 32-39, 34-37, 32-39, 33-39, 34-39, 35-39, 36-39, 37-40, 34-40) of SEQ ID NO:1 can be substituted with any other amino acid or deleted. For example, substitutions at position 34 may affect furin recognition of the first cleavage site. Insertion of one or more additional amino acids within each recognition site may abolish one or both furin cleavage sites. Deletion of one or more of the residues in the degenerate positions may also abolish both furin cleavage sites.

In some embodiments, a furin-resistant IGF-II mutein contains amino acid substitutions at positions corresponding to Arg37 or Arg40 of SEQ ID NO:1. In some embodiments, a furin-resistant IGF-II mutein contains a Lys or Ala substitution at positions Arg37 or Arg40. Other substitutions are possible, including combinations of Lys and/or Ala mutations at both positions 37 and 40, or substitutions of amino acids other than Lys or Ala.

A GILT tag can be fused to the N-terminus or C-terminus of a polypeptide encoding a lysosomal enzyme, or inserted internally. The GILT tag can be fused directly to the lysosomal enzyme polypeptide or can be separated from the lysosomal enzyme polypeptide by a linker or a spacer. An amino acid linker or spacer is generally designed to be flexible or to interpose a structure, such as an alpha-helix, between the two protein moieties. A linker or spacer can be relatively short, such as the sequence Gly-Ala-Pro (SEQ ID NO:3) or Gly-Gly-Gly-Gly-Pro (SEQ ID NO:4), or can be longer, such as, for example, 10-25 amino acids in length. The site of a fusion junction should be selected with care to promote proper folding and activity of both fusion partners and to prevent premature separation of a peptide tag from a GAA polypeptide. In a preferred embodiment, the linker sequence is Gly-Ala-Pro (SEQ ID NO:3).

Detailed description of the GILT technology, exemplary GILT tags and constructs of GILT-tagged lysosomal enzymes can be found in U.S. Pat. Nos. 7,396,811, 7,560,424, and 7,629,309; U.S. Application Publication Nos. 2003-0082176, 2004-0006008, 2003-0072761, 20040005309, 2005-0281805, 2005-0244400, and international publications WO 03/032913, WO 03/032727, WO 02/087510, WO 03/102583, WO 2005/078077, WO/2009/137721, the entire disclosures of which are incorporated herein by reference.

Enzymes with Modified Glycosylation

In some embodiments, the present invention can be used to formulate lysosomal enzymes with modified glycosylation patterns. In some embodiments, enzymes with modified glycosylation patterns are highly phosphorylated. As used herein, the term "highly phosphorylated lysosomal enzymes" refers lysosomal enzymes containing a higher level of phosphorylation as compared to that of a naturally-occurring enzyme. In some embodiments, highly phosphorylated lysosomal enzymes contain a level of phosphorylation which could not be obtained by only isolating the enzyme are treated with GlcNAc-phosphotransferase and phosphodiester-α-GlcNAcase. In some embodiments, "highly phosphorylated lysosomal enzymes" means a lysosomal enzyme that contains from about 6% to about 100% bis-phosphorylated oligosaccharides. In some embodiments, a highly phosphorylated lysosomal enzyme is a highly phosphorylated human GAA. In some embodiments, a highly phosphorylated human GAA contains increased numbers of mannose-6-phosphate (M6P) residues per molecule as compared to a naturally-occurring human GAA. In some embodiments, a highly phosphorylated human GAA may contain, on average, at least 2, 3, 4, 5, or 6 M6P residues per molecule. Example of highly phosphorylated human GAA and other lysosomal enzymes are described in U.S. Pat. Nos. 7,371,366, 7,135,322, 7,067,127, 6,905,856, 6,861,242, 6,828,135, 6,800,472, 6,770,468, 6,670,165, 6,642,038, 6,537,785, and 6,534,300, the disclosures of all of which are hereby incorporated by reference. In some embodiments, highly phosphorylated lysosomal enzymes are produced by endosomal acidification-deficient cell lines (e.g., CHO-K1 derived END3 complementation group). Additional examples are described in WO/2005/077093, the teachings of which are incorporated herein by reference in its entirety.

In some embodiments, the present invention can be used to formulate underglycosylated lysosomal enzymes. As used herein, "underglycosylated lysosomal enzymes" refers to an enzyme in which one or more carbohydrate structures (e.g., M6P residues) that would normally be present on a naturally-occurring enzyme has been omitted, removed, modified, or masked. Typically, underglycosylated lysosomal enzymes have extended half-life in vivo. Underglycosylated lysosomal enzymes may be produced in a host (e.g. bacteria or yeast) that does not glycosylate proteins as conventional mammalian cells (e.g. Chinese hamster ovary (CHO) cells) do. For example, proteins produced by the host cell may lack terminal mannose, fucose, and/or N-acetylglucosamine residues, which are recognized by the mannose receptor, or may be completely unglycosylated. In some embodiments, underglycosylated lysosomal enzymes may be produced in mammalian cells or in other hosts, but treated chemically or enzymatically to remove one or more carbohydrate residues (e.g. one or more M6P residues) or to modify or mask one or more carbohydrate residues. Such chemically or enzymatically treated enzymes are also referred to as deglycosylated lysosomal enzymes. In some embodiments, one or more potential glycosylation sites are removed by mutation of the nucleic acid encoding a lysosomal enzyme, thereby reducing glycosylation of the enzyme when synthesized in a mammalian cell or other cell that glycosylates proteins. In some embodiments, lysosomal enzymes can be produced using a secretory signal peptide (e.g., an IGF-II signal peptide) such that the glycosylation levels of the enzymes are reduced and/or modified. Examples of underglycosylated or deglycosylated lysosomal enzymes are described in U.S. Pat. No. 7,629,309 and U.S. Publication Nos. 20090041741 and 20040248262, the disclosures of all of which are hereby incorporated by reference.

Enzyme Production

Enzymes suitable for the present invention can be produced in any mammalian cells or cell types susceptible to cell culture, and to expression of polypeptides, such as, for example, human embryonic kidney (HEK) 293, Chinese hamster ovary (CHO), monkey kidney (COS), HT1080, C10, HeLa, baby hamster kidney (BHK), 3T3, C127, CV-1, HaK, NS/O, and L-929 cells. Specific non-limiting examples include, but are not limited to, BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells+/−DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 (1982)); MRC 5 cells; FS4 cells; and a human hepatoma line (Hep G2). In some embodiments, enzymes are produced in CHO cells. In some embodiments, enzymes are produced in CHO-derived cells such as endosomal acidification-deficient cell lines (e.g., CHO-K1 derived END3 complementation group).

Enzymes can also be expressed in a variety of non-mammalian host cells such as, for example, insect (e.g., Sf-9, Sf-21, Hi5), plant (e.g., *Leguminosa*, cereal, or tobacco), yeast (e.g., *S. cerivisae, P. pastoris*), prokaryote (e.g., *E. Coli, B. subtilis* and other *Bacillus* spp., *Pseudomonas* spp., *Streptomyces* spp), or fungus.

In some embodiments, a lysosomal protein with or without a furin-resistant GILT tag can be produced in furin-deficient cells. As used herein, the term "furin-deficient cells" refers to any cells whose furin protease activity is inhibited, reduced or eliminated. Furin-deficient cells include both mammalian and non-mammalian cells that do not produce furin or produce reduced amount or defective furin protease. Exemplary furin deficient cells that are known and available to the skilled artisan, including but not limited to FD11 cells (Gordon et al (1997) Infection and Immunity 65(8):3370 3375), and those mutant cells described in Moehring and Moehring (1983) Infection and Immunity 41(3):998 1009. Alternatively, a furin deficient cell may be obtained by exposing the above-described mammalian and non-mammalian cells to mutagenesis treatment, e.g., irradiation, ethidium bromide, bromidated uridine (BrdU) and others, preferably chemical mutagenesis, and more preferred ethyl methane sulfonate mutagenesis, recovering the cells which survive the treatment and selecting for those cells which are found to be resistant to the toxicity of *Pseudomonas* exotoxin A (see Moehring and Moehring (1983) Infection and Immunity 41(3):998 1009).

In other embodiments, transgenic nonhuman mammals have been shown to produce lysosomal enzymes in their milk. Such transgenic nonhuman mammals may include mice, rabbits, goats, sheep, porcines or bovines. See U.S. Pat. Nos.

6,118,045 and 7,351,410, each of which are hereby incorporated by reference in their entirety.

Formulations for Lysosomal Enzymes

The present invention provides formulations for lysosomal enzymes that preserve or enhance protein stability and/or efficacy. In some embodiments, the present invention provides lyophilization formulations for lysosomal enzymes. Lyophilization, or freeze-drying, is a commonly employed technique for preserving proteins which serves to remove water from the protein preparation of interest. Lyophilization, is a process by which the material to be dried is first frozen and then the ice or frozen solvent is removed by sublimation in a vacuum environment. The present invention serves to protect enzymes from freezing and dehydration stresses and preserve or enhance protein stability during freeze-drying and/or preserve or improve stability of lyophilized product during storage.

Because of the variations in temperature and pressure through the lyophilization process, an appropriate choice of excipients or other components such as stabilizers, buffering agents, bulking agents, and surfactants are needed to prevent the enzyme from degradation (e.g., protein aggregation, deamidation, and/or oxidation) during freeze-drying and storage.

In some embodiments, the present invention provides formulations in a liquid form. Liquid formulations of the present invention include, but are not limited to, pre-lyophilization formulations, reconstituted formulations (e.g., formulations reconstituted from lyophilized powders), and liquid formulations suitable for long-term storage in a liquid or frozen state.

Formulations according to the present invention may contain one or more components described below.

Enzyme Concentration

Formulations according to the invention may contain a lysosomal enzyme at various concentrations. In some embodiments, formulations according to the invention may contain a lysosomal enzyme (e.g., recombinant human GAA) at a concentration in the range from about 0.1 mg/ml to 100 mg/ml (e.g., about 0.1 mg/ml to 80 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 60 mg/ml, about 0.1 mg/ml to 50 mg/ml, about 0.1 mg/ml to 40 mg/ml, about 0.1 mg/ml to 30 mg/ml, about 0.1 mg/ml to 25 mg/ml, about 0.1 mg/ml to 20 mg/ml, about 0.1 mg/ml to 15 mg/ml, about 0.1 mg/ml to 10 mg/ml, about 0.1 mg/ml to 5 mg/ml, about 1 mg/ml to 10 mg/ml, about 1 mg/ml to 20 mg/ml, about 1 mg/ml to 40 mg/ml, about 5 mg/ml to 100 mg/ml, about 5 mg/ml to 50 mg/ml, or about 5 mg/ml to 25 mg/ml). In some embodiments, formulations according to the invention may contain a lysosomal enzyme (e.g., recombinant human GAA) at a concentration of approximately 1 mg/ml, 5 mg/ml, 10 mg/ml, 15 mg/ml, mg/ml, 25 mg/ml, 30 mg/ml, 40 mg/ml, 50 mg/ml, 60 mg/ml, 70 mg/ml, 80 mg/ml, 90 mg/ml, or 100 mg/ml.

Surfactants

In some embodiments, formulations according to the present invention contain a surfactant. In particular, formulations provided by the present invention contain a poloxamer as a surfactant. Typically, poloxamers are non-ionic, triblock copolymers. Poloxamers typically have an amphiphilic structure comprised of a central hydrophobic block, between two hydrophilic blocks. Generally, the central hydrophobic block is polyoxypropylene (poly(propylene oxide)) ("PPO") and the two hydrophilic blocks are polyoxyethylene (poly(ethylene oxide)) ("PEO"). A general structure for an exemplary poloxamer is shown as follows:

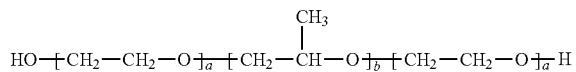

Poloxamers are also known by the trade name Pluronics® (manufactured by BASF). Poloxamers/Pluronics® are available in various grades differing in molecular weights, ratios of hydrophilic to hydrophobic blocks and physical forms, (i.e., liquid, flakes/solids or paste). Exemplary poloxamers/Pluronics® products suitable for the present invention are shown in Table 2 below.

TABLE 2

Poloxamer/Pluronic ® grades and their chemical composition

| Pluronic ® | Poloxamer | a | b | Content of Oxyethylene (Percent) | Molecular Weight |
|---|---|---|---|---|---|
| L 44 NF | 124 | 12 | 20 | 44.8-48.6 | 2090-2360 |
| F 68 NF | 188 | 79 | 28 | 79.9-83.7 | 7680-9510 |
| F 87 NF | 237 | 64 | 37 | 70.5-74.3 | 6840-8830 |
| F 108 NF | 338 | 141 | 44 | 81.4-84.9 | 12700-17400 |
| F 127 NF | 407 | 101 | 56 | 71.5-74.9 | 9840-14600 |

In some embodiments, a poloxamer suitable for the present invention is Pluronic® F-68.

A poloxamer can be included in a formulation of the invention at various concentrations. In some embodiments, a poloxamer is present at a concentration ranging approximately between 0.001% and 1% (e.g., between 0.001% and 0.8%, between 0.001% and 0.6%, between 0.001% and 0.5%, between 0.001% and 0.4%, between 0.001% and 0.3%, between 0.001% and 0.2%, between 0.001% and 0.1%, between 0.01% and 1%, between 0.01% and 0.5%, between 0.01% and 0.4%, between 0.01% and 0.3%, between 0.01% and 0.2%, or between 0.01% and 0.1%) by weight. In some embodiments, a poloxamer is present at a concentration of approximately 0.001%, 0.01%, 0.02%, 0.04%, 0.06%, 0.08%, 0.1%, 0.12%, 0.14%, 0.16%, 0.18%, 0.2%, 0.25%, 0.3%, 0.35%, 0.4%, 0.45%, 0.5%, 0.6%, 0.7%, 0.8%, 0.9%, or 1.0% by weight.

Buffering Agents

In some embodiments, a formulation of the present invention includes a buffering agent. Typically, formulations according to the invention is a pH-buffered solution at a pH ranging from about 4-8 (e.g., about 4.0, 4.5, 5.0, 5.5, 6.0, 6.2, 6.4, 6.5, 6.6, 6.8, 7.0, 7.5, or 8.0) and, in some embodiments, from about 5-7. Exemplary buffering agents suitable for the invention include, but are not limited to, histidine, phosphate, tris(hydroxymethyl)aminomethane ("Tris"), citrate, acetate, sodium acetate, phosphate, succinate and other organic acids. A buffering agent can be present at various concentrations, depending, for example, on the buffer and the desired isotonicity of the formulation (e.g., of the reconstituted formulation). In some embodiments, a buffering agent is present at a concentration ranging between about 1 mM to about 100 mM, or between about 10 mM to about 50 mM, or between about 15 mM to about 50 mM, or between about 20 mM to about 50 mM, or between about 25 mM to about 50 mM. In some embodiments, a suitable buffering agent is present at a concentration of approximately 1 mM, 5 mM, 10 mM, 15 mM, 20 mM, 25 mM, 30 mM, 35 mM, 40 mM, 45 mM or 50 mM.

Stabilizing Agents

In some embodiments, formulations according to the invention may contain a stabilizing agent to protect the enzyme. A stabilizing agent is also referred to as a lyoprotectant. Typically, a suitable stabilizing agent may be sucrose, raffinose, sorbitol, mannitol, trehalose, glycine, arginine, methionine, or combinations thereof. The amount of stabilizing agent or lyoprotectant in a pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the enzyme occurs upon lyophilization. Where the lyoprotectant is a sugar (such as sucrose or trehalose), exemplary lyoprotectant concentrations in the pre-lyophilized formulation may range from about 10 mM to about 400 mM (e.g., from about 30 mM to about 300 mM, and from about 50 mM to about 100 mM), or alternatively, from 0.5% to 15% (e.g., from 1% to 10%, from 5% to 15%, from 5% to 10%) by weight. In some embodiments, the ratio of the mass amount of the stabilizing agent and the enzyme is about 1:1. In other embodiments, the ratio of the mass amount of the stabilizing agent and the enzyme can be about 0.1:1, 0.2:1, 0.5:1, 2:1, 5:1, 10:1, or 20:1.

Bulking Agents

In some embodiments, formulations according to the present invention may further include one or more bulking agents. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, dextran, trehalose, hydroxyethyl starch, or combinations thereof. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%) by weight.

Tonicity

In some embodiments, formulations according to the present invention contain an tonicity agent to keep the pre-lyophilization formulations or the reconstituted formulations isotonic. Typically, by "isotonic" is meant that the formulation of interest has essentially the same osmotic pressure as human blood. Isotonic formulations will generally have an osmotic pressure from about 240 mOsm/kg to about 350 mOsm/kg. Isotonicity can be measured using, for example, a vapor pressure or freezing point type osmometer. Exemplary isotonicity agents include, but are not limited to, glycine, sorbitol, mannitol, sodium chloride, sucrose, dextrose, arginine and combination thereof. In some embodiments, suitable tonicity agents may be present in pre-lyophilized formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight.

Other pharmaceutically acceptable carriers, excipients or stabilizers such as those described in Remington's Pharmaceutical Sciences 16th edition, Osol, A. Ed. (1980) may be included in a formulation according to the present invention provided that they do not adversely affect the desired characteristics of the formulation. Acceptable carriers, excipients or stabilizers are nontoxic to recipients at the dosages and concentrations employed and include, but are not limited to, additional buffering agents; preservatives; co-solvents; antioxidants including ascorbic acid and methionine; chelating agents such as EDTA; metal complexes (e.g., Zn-protein complexes); biodegradable polymers such as polyesters; and/or salt-forming counterions such as sodium.

Formulations described herein may contain more than one protein as appropriate for a particular indication being treated, preferably those with complementary activities that do not adversely affect the other protein.

Formulations to be used for in vivo administration must be sterile. This is readily accomplished by filtration through sterile filtration membranes, prior to, or following, lyophilization and reconstitution.

In some embodiments, the present invention provides "stable" formulations for lysosomal enzymes described herein. As used herein, a "stable" formulation is one in which the enzyme therein essentially retains its physical and chemical stability and integrity during lyophilization, storage, shipping and infusion. As a result, formulations provided by the present invention reduce or eliminate formation of high molecule weight aggregates, protein degradation during freeze-drying, storage, shipping and infusion. In particular embodiments, a stable formulation provided by the present invention reduces or eliminates enzyme precipitation during freeze-drying, storage, shipping and infusion. Enzyme precipitation may be determined by visual examination. In addition, various analytical techniques for measuring protein stability can be used to measure enzyme stability. See, *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured after storage at a selected temperature (e.g., 0° C., 5° C., 25° C. (room temperature), 30° C., 40° C.) for a selected time period (e.g., 2 weeks, 1 month, 1.5 months, 2 months, 3, months, 4 months, 5 months, 6 months, 12 months, 18 months, 24 months, etc.). For rapid screening, the formulation may be kept at 40° C. for 2 weeks to 1 month, at which time stability is measured. Where the formulation is to be stored at 2-8° C., generally the formulation should be stable at 25° C. (i.e., room temperature) or 40° C. for at least 1 month and/or stable at 2-8° C. for at least 3 months, 6 months, 1 year or 2 years. Where the formulation is to be stored at 30° C., generally the formulation should be stable for at least 3 months, 6 months, 1 year or 2 years at 30° C. and/or stable at 40° C. for at least 2 weeks, 1 month, 3 months or 6 months. In some embodiments, the extent of aggregation following lyophilization and storage can be used as an indicator of protein stability. As used herein, the term "high molecular weight ("HMW") aggregates" refers to an association of at least two protein monomers. For the purposes of this invention, a monomer refers to the single unit of any biologically active form of the protein of interest. The association may be covalent, non-covalent, disulfide, non-reducible crosslinking, or by other mechanism.

For example, a "stable" formulation may be one wherein less than about 10% (e.g., less than 9%, 8%, 7%, 6%, 5%, 4%, 3%, 2%, 1%, 0.5%) and preferably less than about 5% (e.g., less than 4%, 3%, 2%, 1%, 0.5%) of the protein is present as an aggregate in the formulation (also referred to as high molecular weight species ("HMW")). In some embodiments, stability can be measured by an increase in aggregate formation following lyophilization and storage of the lyophilized formulation. For example, a "stable" lyophilized formulation may be one wherein the increase in aggregate in the lyophilized formulation is less than about 5% (e.g., less than 4%, 3%, 2%, 1%, 0.5%) and preferably less than about 3% (e.g., 2%, 1%, 0.5%, 0.2%, 0.1%) when the lyophilized formulation is stored at 25° C. (i.e., room temperature) or 40° C. for at least 2 weeks, 1 month, 3 months or 6 months, or at 2-8° C. for at least 3 months, 6 months, 1 year or 2 years. Aggregate or HMW species can be analyzed using methods known in the art including, but not limited to, size exclusion HPLC (SE- HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof.

Kits

The present invention also provides kits containing reagents or formulations according to the present invention. In some embodiments, a kit according to the invention may include a container containing lyophilized mixture of a lysosomal enzyme (e.g., human GAA) and provide instructions for its reconstitution and/or use. Suitable containers include, for example, bottles, vials (e.g. dual chamber vials), bags (e.g., iv bags), syringes (such as dual chamber syringes) and test tubes. The container may be formed from a variety of materials such as glass or plastic. The container holds the lyophilized formulation and the label on, or associated with, the container may indicate directions for reconstitution and/or use. For example, the label may indicate that the lyophilized formulation is reconstituted to protein concentrations as described above. The label may further indicate that the formulation is useful or intended for, e.g., intravenous administration as a bolus or by continuous infusion over a period of time, by intramuscular, subcutaneous, intra-articular, intrasynovial, or intrathecal routes. A suitable kit may further include a second container containing a suitable diluent (e.g. BWFI). Upon mixing of the diluent and the lyophilized formulation, the final protein concentration in the reconstituted formulation will generally be at least about 1 mg/ml (e.g., about 5 mg/ml, 10 mg/ml, 15 mg/ml, 20 mg/ml, 25 mg/ml, 30 mg/ml, 35 mg/ml, 40 mg/ml, 50 mg/ml, 60 mg/ml, 70 mg/ml, 80 mg/ml, 90 mg/ml, or 100 mg/ml).

EXAMPLES

Example 1

Surfactant Screening

The experiments in this example were designed as part of the pre-formulation study to examine the stability of ZC-701 in various formulation conditions including pH, tonicity modifier, and surfactant.

ZC-701 is a fusion protein containing a GILT tag derived from human IGF-II (IGF-II Δ2-7) fused to the N-terminus of a fragment of human GAA (amino acids 70-952 of human GAA). There is a three amino acid spacer (GAP) between the GILT tag and the GAA fragment. The amino acid sequence of ZC-701 is shown in SEQ ID NO:2.

```
                                         (SEQ ID NO: 2)
ALCGGELVDTLQFVCGDRGFYFSRPASRVSRRSRGIVEECCFRSCDLALL

ETYCATPAKSEGAPAHPGRPRAVPTQCDVPPNSRFDCAPDKAITQEQCEA

RGCCYIPAKQGLQGAQMGQPWCFFPPSYPSYKLENLSSSEMGYTATLTRT

TPTFFPKDILTLRLDVMMETENRLHFTIKDPANRRYEVPLETPRVHSRAP

SPLYSVEFSEEPFGVIVHRQLDGRVLLNTTVAPLFFADQFLQLSTSLPSQ

YITGLAEHLSPLMLSTSWTRITLWNRDLAPTPGANLYGSHPFYLALEDGG

SAHGVFLLNSNAMDVVLQPSPALSWRSTGGILDVYIFLGPEPKSVVQQYL

DVVGYPFMPPYWGLGFHLCRWGYSSTAITRQVVENMTRAHFPLDVQWNDL

DYMDSRRDFTFNKDGFRDFPAMVQELHQGGRRYMMIVDPAISSSGPAGSY

RPYDEGLRRGVFITNETGQPLIGKVWPGSTAFPDFTNPTALAWWEDMVAE

FHDQVPFDGMWIDMNEPSNFIRGSEDGCPNNELENPPYVPGVVGGTLQAA

TICASSHQFLSTHYNLHNLYGLTEAIASHRALVKARGTRPFVISRSTFAG

HGRYAGHWTGDVWSSWEQLASSVPEILQFNLLGVPLVGADVCGFLGNTSE

ELCVRWTQLGAFYPFMRNHNSLLSLPQEPYSFSEPAQQAMRKALTLRYAL

LPHLYTLFHQAHVAGETVARPLFLEFPKDSSTWTVDHQLLWGEALLITPV

LQAGKAEVTGYFPLGTWYDLQTVPIEALGSLPPPPAAPREPAIHSEGQWV

TLPAPLDTINVHLRAGYIIPLQGPGLTTTESRQQPMALAVALTKGGEARG

ELFWDDGESLEVLERGAYTQVIFLARNNTIVNELVRVTSEGAGLQLQKVT

VLGVATAPQQVLSNGVPVSNFTYSPDTKVLDICVSLLMGEQFLVSWC
```

In this example, the following formulation parameters were examined: (1) pH: 4.0, 5.0, 6.0, and 6.2; (2) Buffers: sodium acetate buffer (pH 3.0-5.0) and sodium phosphate buffer (pH 7.0-8.0), all at 10 mM concentration; (3) Tonicity Modifiers: 100 mM sodium chloride (NaCl), 150 mM sodium chloride (NaCl), 3.5% sorbitol, and 5.0% sorbitol; (4) Stabilizer: 100 mM Arginine, 0.1 mM EDTA; (5) Surfactants: polysorbate 20, polysorbate 80, and Pluronic F-68; and (6) Product Concentration: 5 and 15 mg/mL Fill volume was fixed at approximately 0.5 mL. All formulation candidates were formulated by dialysis against each candidate formulation in this study.

The formulations were tested under stress conditions listed in Table 3.

TABLE 3

Exemplary stress conditions

| Stress | Conditions | Time Points |
|---|---|---|
| Temperature | −20° C. | 1, 2, 4, 8 weeks |
|  | 4° C. | 0, 1, 2, 4, 8 weeks |
|  | 25° C. | 1, 2, 4, 8 weeks |
|  | 40° C. | 1, 2, 4, 8 weeks |
| Agitation | Agitation by mini-vortexer | 4 hours |
| Freeze-thaw | −70° C. to RT | 5 consecutive cycles |
| UV-light | Exposure to UV-light (broad spectrum) | 24 hours |

In order to analyze major degradation products generated under stresses, SE-HPLC, RP-HPLC and SDS-PAGE stability-indicating assays were used.

Figure 2:
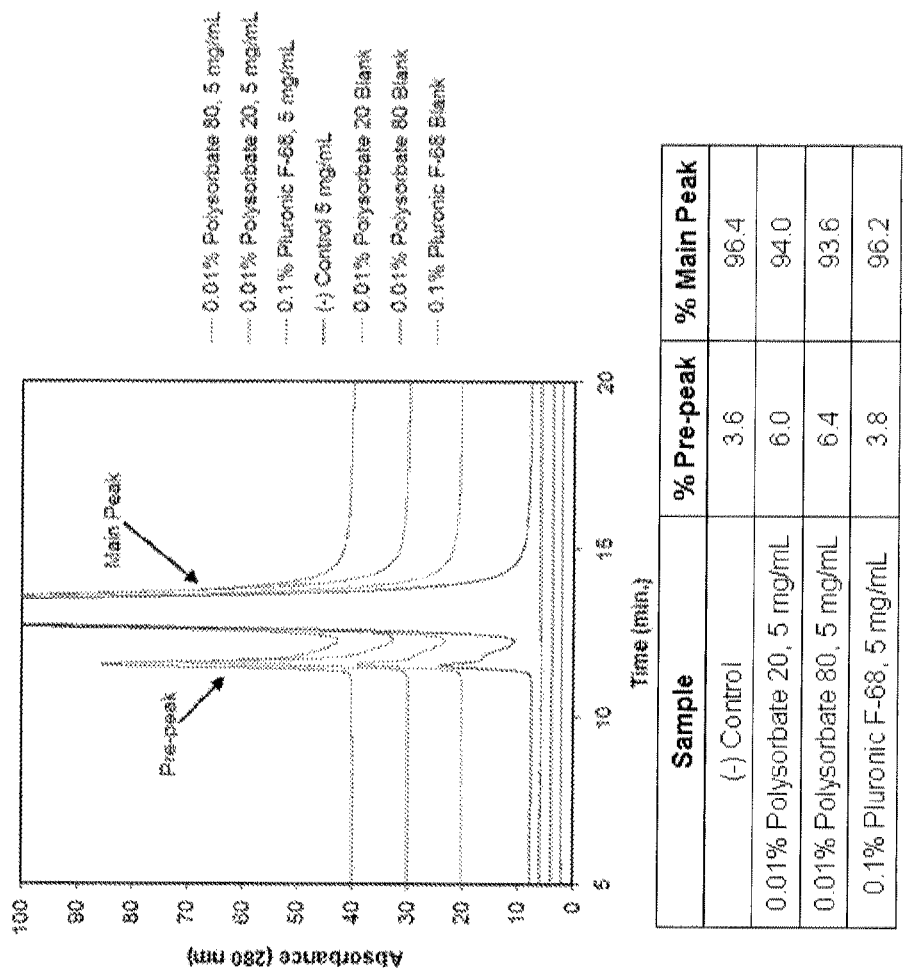
FIG. 2 illustrates exemplary SE-HPLC chromatograms of samples after agitation for 4 hours at room temperature. Sample agitated without surfactant was not analyzed due to precipitation.

Typically, the product precipitates when agitation stress is introduced. As described below, it was observed that addition of Pluronic® F-68 as a surfactant in the formulation stabilized the product against agitation stress. Briefly, the product was subjected to constant agitation for up to 4 hours to understand the stability of product under agitation and/or shear stress. The product in the current bulk formulation of 10 mM sodium phosphate, 145.15 mM NaCl, 2.33 mM KCl, 2 mM potassium phosphate, pH 7.2, 10.06 mg/mL, lot ZC-701-B20-10 was used for this study. FIG. 1 provides a picture of vials from the surfactant screening study. The agitated sample without surfactant (+ control) precipitated, suggesting that the product precipitates under the agitation stress. Addition of each of the tested surfactants, i.e., 0.01% polysorbate 20, 0.01% polysorbate 80, or 0.1% of Pluronic® F-68 (poloxamer 188), protected the product against agitation-induced precipitation. Based on SE-HPLC analysis (FIG. 2), Pluronic® F-68 also prevented any soluble aggregate from forming.

Based on the agitation stress study with various surfactants, Pluronic F-68 was selected as a surfactant for further formulation study. Actual formulations tested in this study are listed in Table 4.

TABLE 4

Exemplary formulations tested under stress conditions.

| Form Code | Buffer | pH | Tonicity Modifier | Surfactant (%) | Stabilizer | Concentration (mg/mL) |
|---|---|---|---|---|---|---|
| 5A4N | 10 mM Sodium Acetate | 4.0 | 150 mM NaCl | 0.1% F-68 | | 5 |
| 5A4S | 10 mM Sodium Acetate | 4.0 | 5% Sorbitol | 0.1% F-68 | | 5 |
| 5A4NR | 10 mM Sodium Acetate | 4.0 | 100 mM NaCl | 0.1% F-68 | 100 mM Arginine | 5 |
| 5A4SR | 10 mM Sodium Acetate | 4.0 | 3.5% Sorbitol | 0.1% F-68 | 100 mM Arginine | 5 |
| 5A5N | 10 mM Sodium Acetate | 5.0 | 150 mM NaCl | 0.1% F-68 | | 5 |
| 5A5S | 10 mM Sodium Acetate | 5.0 | 5% Sorbitol | 0.1% F-68 | | 5 |
| 5P6N | 10 mM Sodium Phosphate | 6.0 | 150 mM NaCl | 0.1% F-68 | | 5 |
| 5P6S | 10 mM Sodium Phosphate | 6.0 | 5% Sorbitol | 0.1% F-68 | | 5 |
| 5P62N | 10 mM Sodium Phosphate | 6.2 | 150 mM NaCl | None | | 5 |
| 5P6NR | 10 mM Sodium Phosphate | 6.0 | 100 mM NaCl | 0.1% F-68 | 100 mM Arginine | 5 |
| 5P6NE | 10 mM Sodium Phosphate | 6.0 | 150 mM NaCl | 0.1% F-68 | 0.1 mM EDTA | 5 |
| 15P6N | 10 mM Sodium Phosphate | 6.0 | 150 mM NaCl | 0.1% F-68 | | 15 |
| 15P6S | 10 mM Sodium Phosphate | 6.0 | 5% Sorbitol | 0.1% F-68 | | 15 |

Formulations were exposed to various stress conditions (Table 3). It was observed that for example, under ionic conditions, in the absence of arginine, the product was sensitive to freeze/thaw stress. As another example, at pH 6, the product was sensitive to UV light stress. When incubated at 40° C. in the accelerated stability study, all formulations except 10 mM sodium acetate, 5% sorbitol, 0.1% Pluronic® F-68, pH 4.0 precipitated. At lower temperatures, 4° C. and −20° C., the 10 mM sodium acetate, 5% sorbitol, 0.1% Pluronic F-68, pH 4.0 formulation was the only formulation that did not produce aggregates, as characterized by SE-HPLC. Results obtained from this study suggest that stable formulations include 0.1% Pluronic® F-68 at pH 4 with a non-ionic tonicity modifier.

Example 2

Lyophilized Formulation for ZC-701

The experiments in this example were designed to optimize lyophilization formulations for ZC-701. In particular, these studies provide information on the effect of formulation on stability of the product. For example, through a forced degradation study with selected formulation candidates, the following objectives were addressed: (1) To understand stresses to which the product is susceptible; (2) To identify degradation products; (3) To confirm stability-indicating assays; and (4) To understand stable formulation conditions.

ZC-701 was formulated into various citrate and phosphate based lyo-formulations. The following formulation parameters were examined: (1) Buffers: Citrate (pH 6.0), or Phosphate/Citrate (pH 6.0); (2) Bulking Agents: 2% Glycine, or 4% Mannitol. The following parameters were used in all the formulations tested: (3) Fill volume: 0.5 mL; (4) pH: 6.0; (5) Surfactant: Poloxamer 188; and (6) Stabilizer: 1% Trehalose.

All formulation candidates were formulated by dialysis against each candidate formulation in this study and exemplary formulations are shown in Table 5.

TABLE 5

Exemplary Formulations of ZC-701

| Code | Buffer | pH | Bulking Agent | Stabilizer | Surfactant | Conc. (mg/ml) |
|---|---|---|---|---|---|---|
| C6GT | 50 mM Citrate | 6.0 | 2% Glycine | 1% Trehalose | 0.10% Poloxamer 188 | 10 |
| C6MT | 50 mM Citrate | 6.0 | 4% Mannitol | 1% Trehalose | 0.10% Poloxamer 188 | 10 |
| PC6MT* | 50 mM Phosphate/Citrate | 6.0 | 4% Mannitol | 1% Trehalose | 0.10% Poloxamer 188 | 10 |

Typically, a lyophilization cycle can be chosen based on cake integrity, high glass transition temperature, optimum moisture content (<1%), easy and complete reconstitution, and minimum injection associated pain (for a 1 mg dose), using the following assays: visual appearance, pH, moisture content (Integrity Biosolution's protocol), FTIR for structural analysis (Integrity Biosolution's protocol), osmolality (Integrity Biosolution's protocol), differential Scanning calorimetry (Integrity Biosolution's protocol), SE-HPLC, SDS-PAGE.

Figure 3:
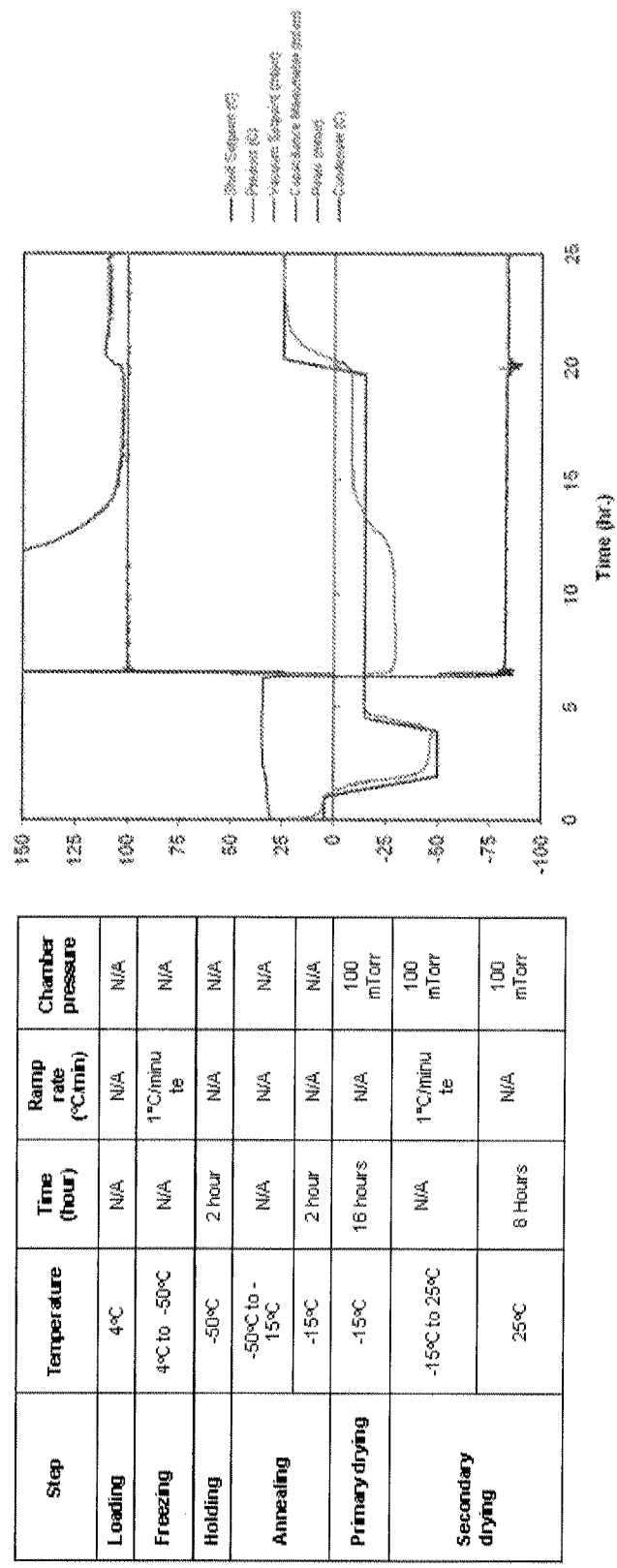
FIG. 3 illustrates an exemplary lyophilization cycle used to lyophilize various formulations.
Figure 4:
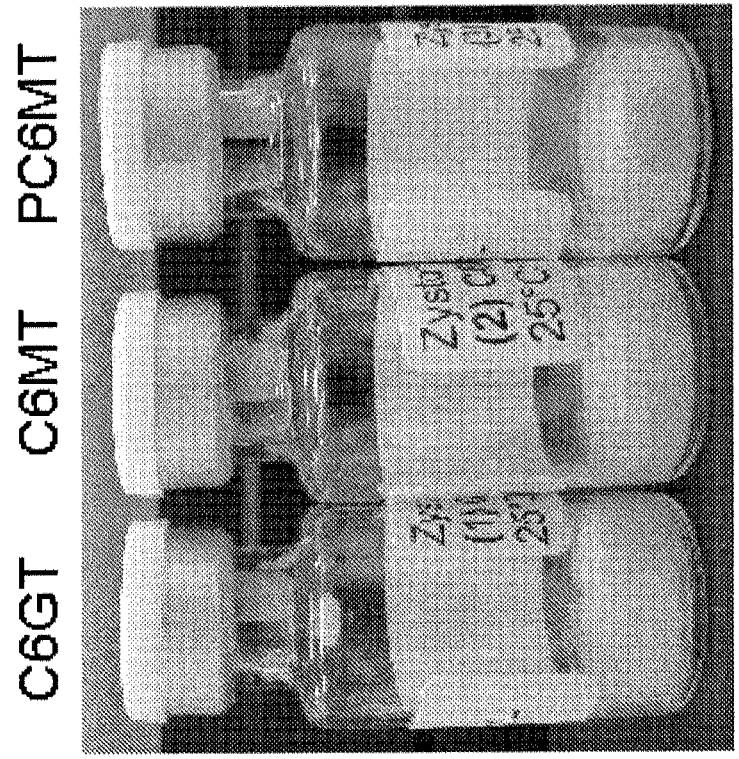
FIG. 4 depicts exemplary vials containing formulation post-drying.

Exemplary formulations (Table 5) were lyophilized in Type I borosilicate glass vials with Fluorotec® coated rubber stoppers with a 0.5 mL fill volume. The lyophilization cycle as shown in FIG. 3 was used to dry the formulations. Firm, good looking cakes were formed after drying (FIG. 4). However, the moisture content was greater than 1% in the three formulations (Table 6). This may be due to the high concentration of citrate in the formulations. Lyo cycle optimization should reduce moisture content.

TABLE 6

Moisture Analysis and Osmolality Results

| ID | Moisture Content Time Zero | Moisture Content 16 Weeks @ 25° C. | Osmolality |
|---|---|---|---|
| C6GT | 1.58 | 2.94 | 478 |
| C6MT | 3.81 | 2.87 | 485 |
| PC6MT | 2.54 | 2.86 | 458 |

Figure 5:
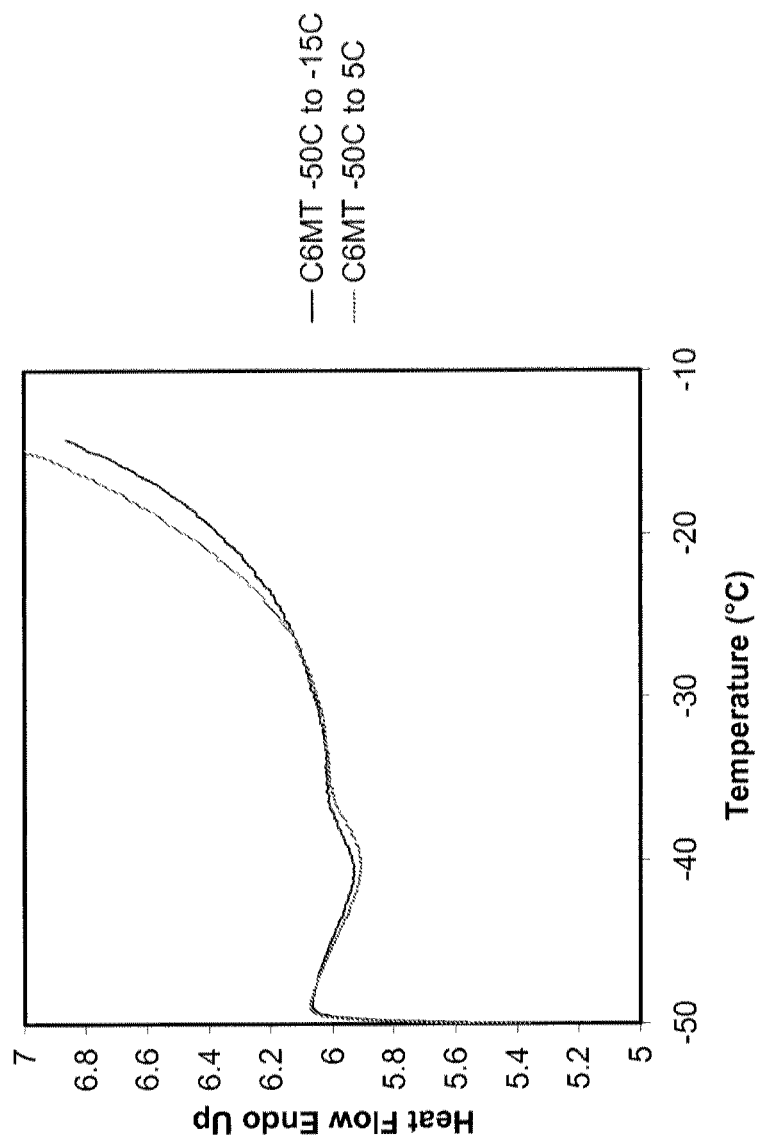
FIG. 5 illustrates exemplary differential scanning calorimetry of C6MT.

Differential scanning calorimetry of C6MT was performed. The presence of citrate in the formulations appeared to mask any eutectic melting signals that might have occurred at around −15° C. in the assay. Devitrification attempts by warming the samples to −15° C. from −50° C., cooling back to −50° C. and warming to 4° C. showed no difference in heat flow (FIG. 5). The glass transition temperature at −38° C. did not appear to cause any cake collapse after lyophilization.

Stress Studies

TABLE 7

The formulations were tested under the following stress conditions:

| Stress | Condition | Time Points |
|---|---|---|
| Temperature | 4° C. | Pre-lyo, 0, 2* days; 1, 2, 4, 8, 12, 16 weeks; ** |
| | 25° C.*** | 2 days; 1, 2, 4, 8, 12, 16 weeks; ** |
| | 40° C. | 2 days; 1, 2, 4 weeks |

*One additional set of samples was reconstituted at time zero and stored in the liquid state for two (2) days at 4° C., prior to analysis.
**3 additional vials/formulation were included at 4 & 25° C. for moisture analyses.
***1 extra vial/formulation for bioassays at 0, 4, 8, 16 weeks for 25° C. samples.
Only selected formulations were analyzed from 8 weeks.

Figure 6:
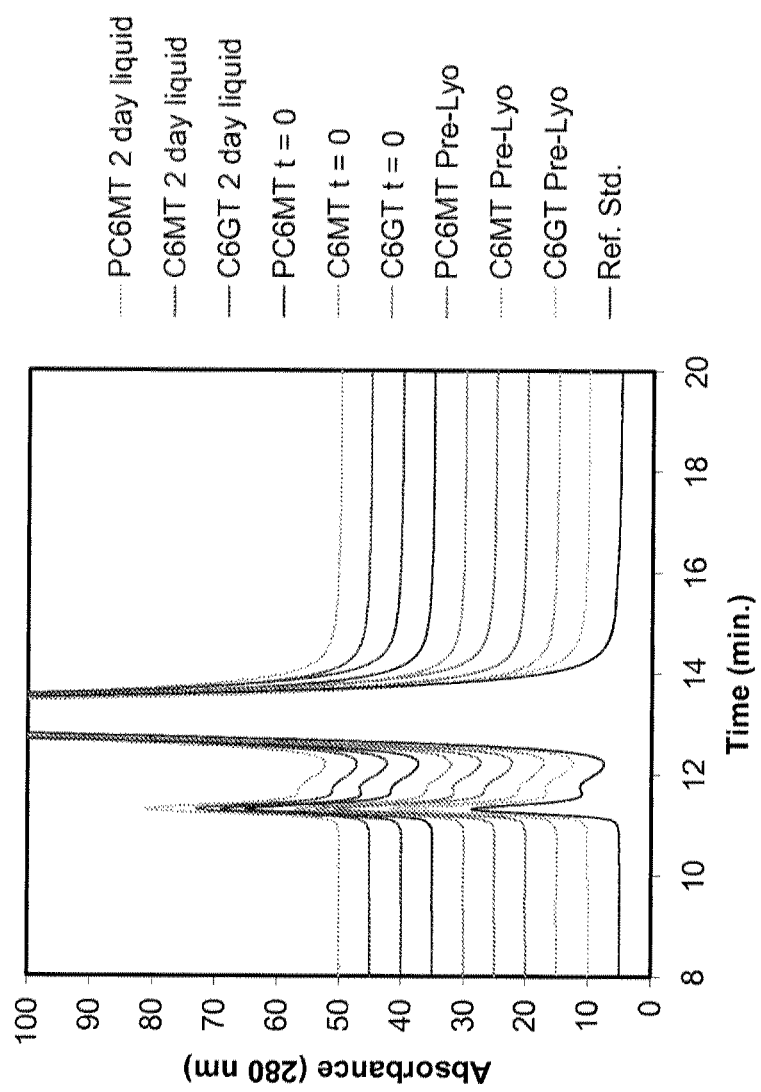
FIG. 6 illustrates exemplary SE-HPLC chromatograms of all formulations at Pre-Lyo, Time Zero, and Two Day Reconstitution. No detectable degradation took place as a result of the lyophilization process or two day storage after reconstitution.
Figure 7:
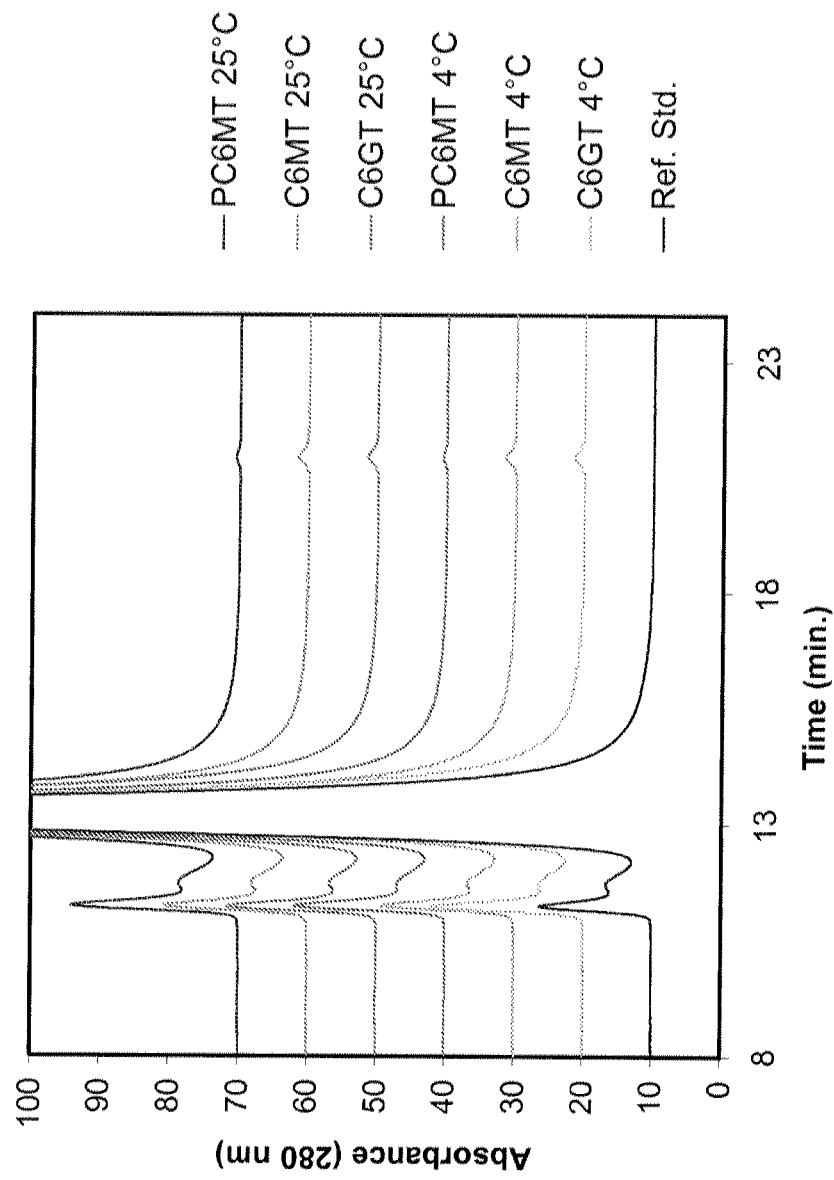
FIG. 7 illustrates exemplary SE-HPLC chromatograms of all tested formulations after 16 week storage at 4° C. and 25° C.
Figure 8:
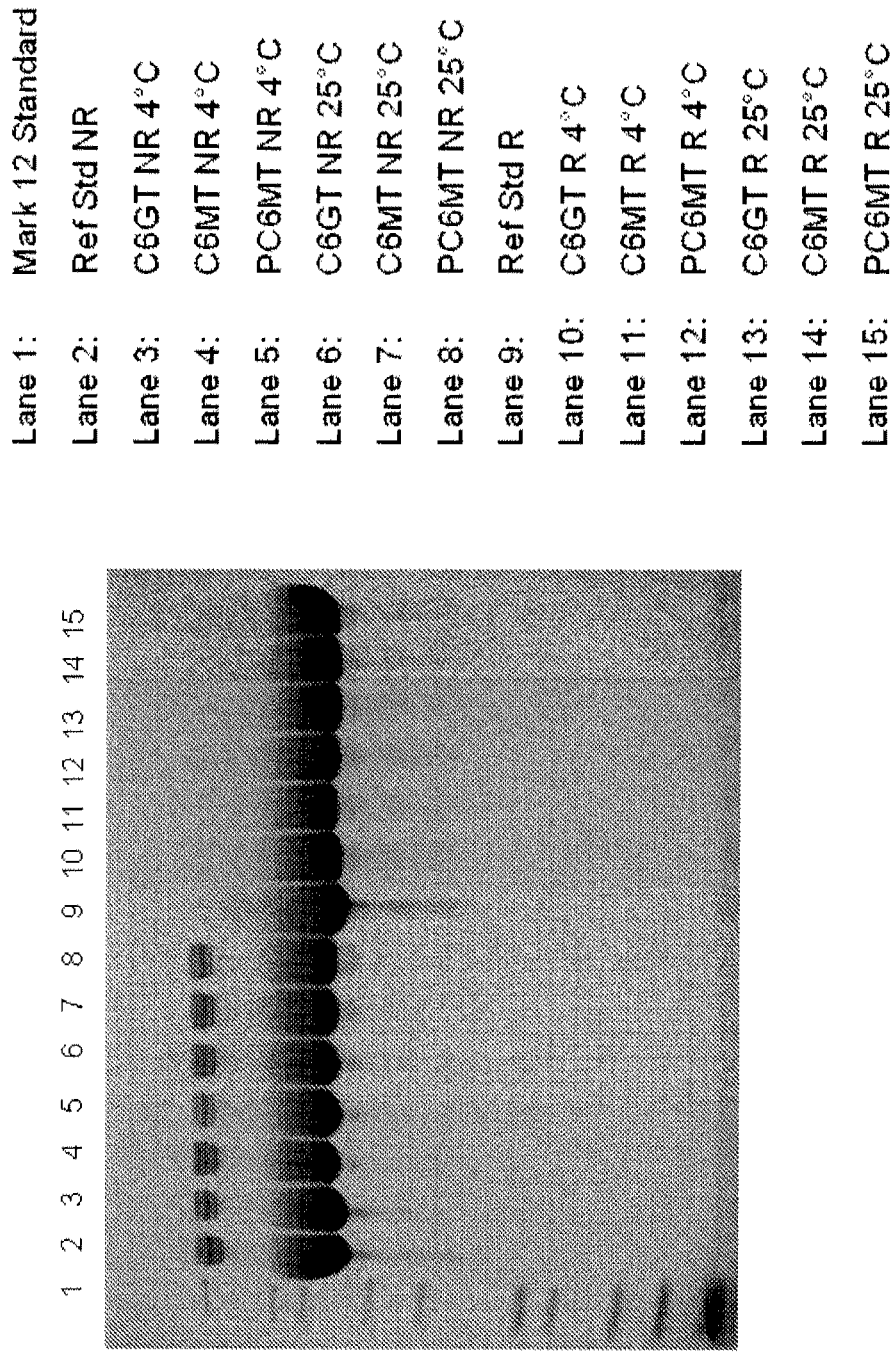
FIG. 8 illustrates exemplary SDS-PAGE of all tested formulations after 16 weeks storage at 4° C. and 25° C.
Figure 9:
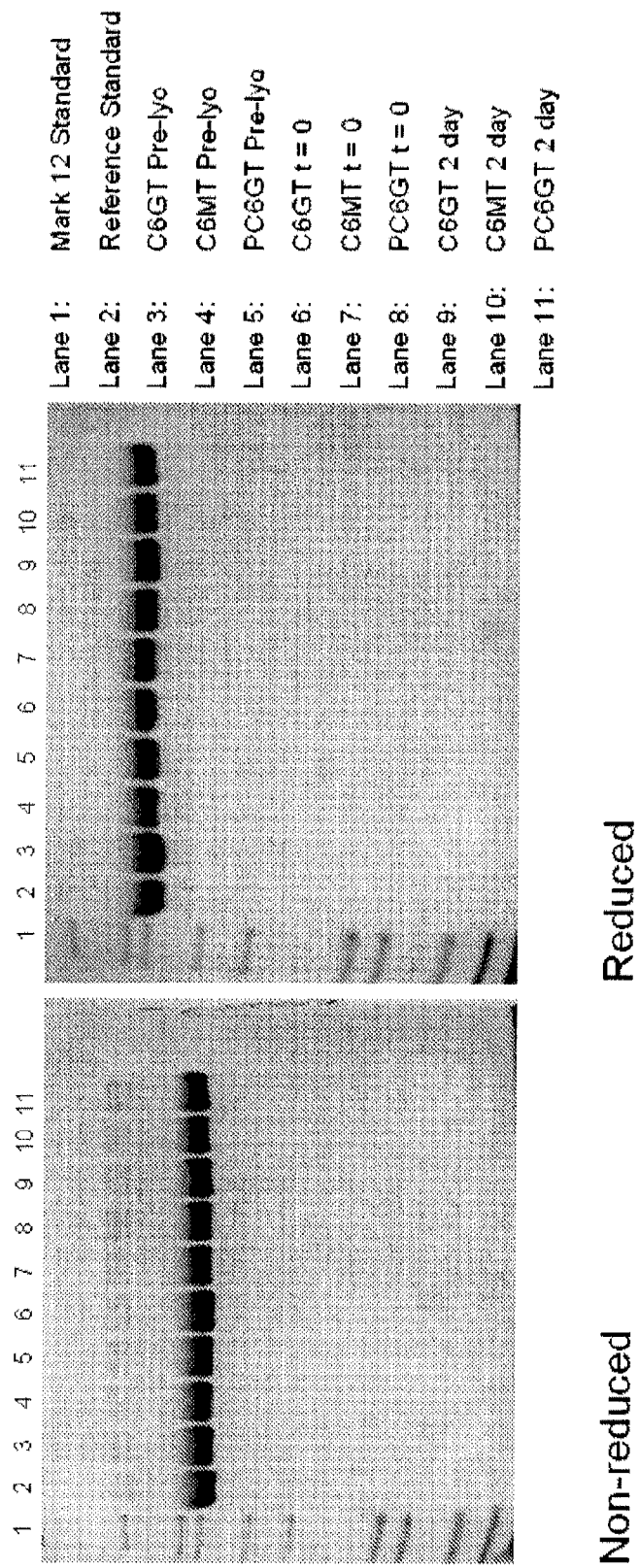
FIG. 9 illustrates exemplary SDS-PAGE analysis of pre-lyo, time zero, and 2 day reconstitution of tested formulations.
Figure 10:
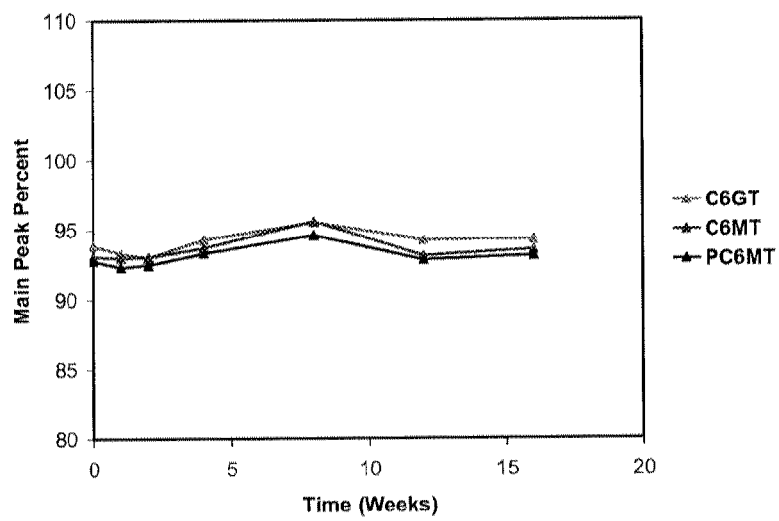
FIG. 10 illustrates exemplary stability of three tested formulations stored at (A) 4° C., (B) 25° C., and (C) 37° C. by SEC-HPLC.
Figure 10:
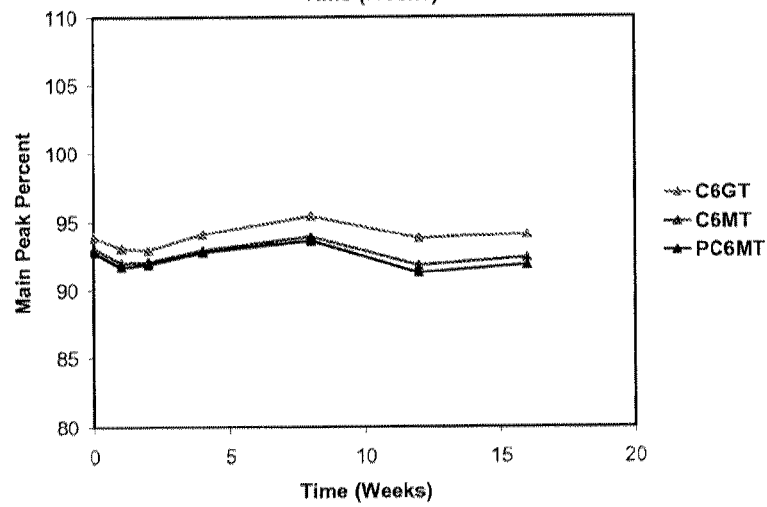
Figure 10:
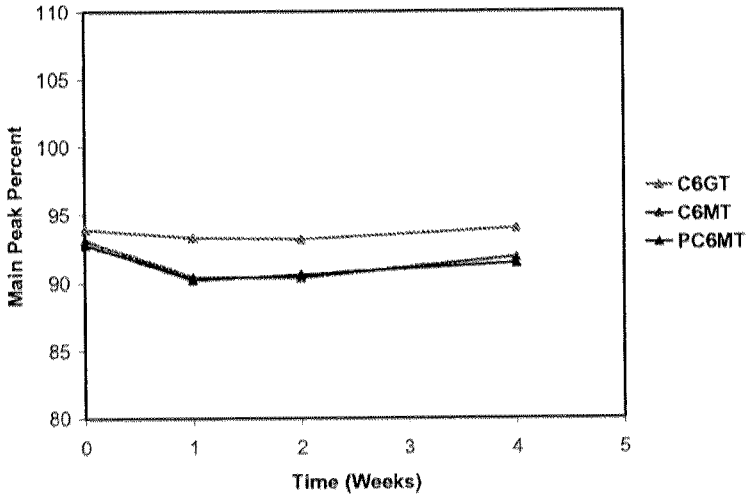

In order to analyze major degradation products generated under the stresses, Size Exclusion (SE-HPLC) and Sodium Dodecyl Sulfate-Polyacrylamide Gel Electrophoresis (SDS-PAGE) stability-indicating assays were used in this study. For Size Exclusion (SE-HPLC), Mobile Phase: Phosphate Buffered Saline (PBS) 0.1M, pH 7.2 NaCl 0.15 M; Column: TSK-GEL G2000SWXL 300×7.8 mm ID by TOSOH Bioscience; Flow Rate: 0.5 mL/min; Sample load: 50 μg/injection. For Sodium Dodecyl Sulfate-Polyacrylamide Gel Electrophoresis (SDS-PAGE), Gel Type: NuPAGE Novex 4-12% BisTris Gel; Running Buffer: 1×MOPS SDS Running Buffer; Staining Reagent: SimplyBlue SafeStain, Invitrogen; Load Volume: 12 μL of Mark 12™ MW Standard, Invitrogen; Sample Load: 10 μg ZC-701 exhibited very little overall degradation throughout the 16 week time period as determined by SE-HPLC (FIGS. 6 & 7). After 16 weeks of storage at 4° C. and 25° C., and compared to a frozen reference standard, the formulations showed no change when analyzed by SDS-PAGE (FIG. 8). No significant change was observed when reconstituted formulations were stored for two days at 4° C. (FIG. 9). As described above, both initial and final moisture content were high due to the use of citrate in the formulation buffer (Table 6). The choice of citrate also resulted in a high osmolality (Table 6). Stability profiles for each formulation tested are illustrated in FIG. 10.

As shown below in Table 8, stability studies indicated that, in lyophilized formulations, the formulation containing 50 mM Citrate at pH 6.0, 2% Glycine, 1% Trehalose, and 0.1% Poloxamer 188 was slightly more stable than the other two conditions following storage at 4° C. and 25° C. SDS-PAGE did not suggest any appreciable differences among the formulations. No appreciable degradation was observed in this formulation after 16 weeks of storage at 4° C. and 25° C. The differences among the three formulations are small.

TABLE 8

Summary of stability results from exemplary formulation candidates

| ID | Buffer (10 mM) | Tonicity Modifier | Surfactant | Temp (° C.) | pH | HPLC Purity (%) SE | RP | IE | Conc. (mg/mL) |
|---|---|---|---|---|---|---|---|---|---|
| (1) Pre-Lyo, Time 0, and 2 Day Reconstitution ||||||||||
| C6GT | Citrate | 2% Glycine/1% Trehalose | 0.10% Poloxamer | PreLyo | 6.37 | 93.9 | N/A | N/A | 11.68 |
| C6MT | Citrate | 4% Mann/1% Trehalose | 0.10% Poloxamer | PreLyo | 6.25 | 93.1 | N/A | N/A | 8.90 |
| PC6MT | Phosphate/Citrate | 4% Mann/1% Trehalose | 0.10% Poloxamer | PreLyo | 6.26 | 92.8 | N/A | N/A | 9.62 |
| C6GT | Citrate | 2% Glycine/1% Trehalose | 0.10% Poloxamer | T Zero | 6.27 | 93.9 | N/A | N/A | 11.03 |
| C6MT | Citrate | 4% Mann/1% Trehalose | 0.10% Poloxamer | T Zero | 6.18 | 93.1 | N/A | N/A | 9.18 |
| PC6MT | Phosphate/Citrate | 4% Mann/1% Trehalose | 0.10% Poloxamer | T Zero | 6.05 | 92.8 | N/A | N/A | 9.65 |
| C6GT | Citrate | 2% Glycine/1% Trehalose | 0.10% Poloxamer | 2 Day Recon | 6.50 | 93.9 | N/A | N/A | 11.39 |
| C6MT | Citrate | 4% Mann/1% Trehalose | 0.10% Poloxamer | 2 Day Recon | 6.33 | 93.0 | N/A | N/A | 9.61 |
| PC6MT | Phosphate/Citrate | 4% Mann/1% Trehalose | 0.10% Poloxamer | 2 Day Recon | 6.35 | 92.7 | N/A | N/A | 9.26 |
| (2) 1 week ||||||||||
| C6GT | Citrate | 2% Glycine/1% Trehalose | 0.10% Poloxamer | 5 | 6.31 | 93.3 | N/A | N/A | 11.28 |
| C6MT | Citrate | 4% Mann/1% Trehalose | 0.10% Poloxamer | 5 | 6.21 | 93.0 | N/A | N/A | 9.55 |
| PC6MT | Phosphate/Citrate | 4% Mann/1% Trehalose | 0.10% Poloxamer | 5 | 6.08 | 92.3 | N/A | N/A | 10.07 |
| C6GT | Citrate | 2% Glycine/1% Trehalose | 0.10% Poloxamer | 25 | 6.28 | 93.1 | N/A | N/A | 11.46 |
| C6MT | Citrate | 4% Mann/1% Trehalose | 0.10% Poloxamer | 25 | 6.15 | 92.0 | N/A | N/A | 9.43 |
| PC6MT | Phosphate/Citrate | 4% Mann/1% Trehalose | 0.10% Poloxamer | 25 | 6.09 | 91.7 | N/A | N/A | 9.96 |

TABLE 8-continued

Summary of stability results from exemplary formulation candidates

| ID | Buffer (10 mM) | Tonicity Modifier | Surfactant | Temp (° C.) | pH | HPLC Purity (%) SE | RP | IE | Conc. (mg/mL) |
|---|---|---|---|---|---|---|---|---|---|
| C6GT | Citrate | 2% Glycine/ 1% Trehalose | 0.10% Poloxamer | 37 | 6.17 | 93.3 | N/A | N/A | 8.94 |
| C6MT | Citrate | 4% Mann/1% Trehalose | 0.10% Poloxamer | 37 | 6.09 | 90.4 | N/A | N/A | 9.53 |
| PC6MT | Phosphate/ Citrate | 4% Mann/1% Trehalose | 0.10% Poloxamer | 37 | 6.10 | 90.2 | N/A | N/A | 10.33 |

(3) 2 weeks

| ID | Buffer (10 mM) | Tonicity Modifier | Surfactant | Temp (° C.) | pH | SE | RP | IE | Conc. (mg/mL) |
|---|---|---|---|---|---|---|---|---|---|
| C6GT | Citrate | 2% Glycine/ 1% Trehalose | 0.10% Poloxamer | 5 | 6.31 | 93.0 | N/A | N/A | 11.29 |
| C6MT | Citrate | 4% Mann/1% Trehalose | 0.10% Poloxamer | 5 | 6.21 | 93.1 | N/A | N/A | 9.09 |
| PC6MT | Phosphate/ Citrate | 4% Mann/1% Trehalose | 0.10% Poloxamer | 5 | 6.08 | 92.5 | N/A | N/A | 9.74 |
| C6GT | Citrate | 2% Glycine/ 1% Trehalose | 0.10% Poloxamer | 25 | 6.28 | 92.9 | N/A | N/A | 11.11 |
| C6MT | Citrate | 4% Mann/1% Trehalose | 0.10% Poloxamer | 25 | 6.15 | 92.1 | N/A | N/A | 8.95 |
| PC6MT | Phosphate/ Citrate | 4% Mann/1% Trehalose | 0.10% Poloxamer | 25 | 6.09 | 91.9 | N/A | N/A | 9.48 |
| C6GT | Citrate | 2% Glycine/ 1% Trehalose | 0.10% Poloxamer | 37 | 6.17 | 93.2 | N/A | N/A | 8.47 |
| C6MT | Citrate | 4% Mann/1% Trehalose | 0.10% Poloxamer | 37 | 6.09 | 90.3 | N/A | N/A | 9.23 |
| PC6MT | Phosphate/ Citrate | 4% Mann/1% Trehalose | 0.10% Poloxamer | 37 | 6.10 | 90.6 | N/A | N/A | 9.64 |

(4) 4 weeks

| ID | Buffer (10 mM) | Tonicity Modifier | Surfactant | Temp (° C.) | pH | SE | RP | IE | Conc. (mg/mL) |
|---|---|---|---|---|---|---|---|---|---|
| C6GT | Citrate | 2% Glycine/ 1% Trehalose | 0.10% Poloxamer | 5 | 6.20 | 94.3 | N/A | N/A | 11.14 |
| C6MT | Citrate | 4% Mann/1% Trehalose | 0.10% Poloxamer | 5 | 6.06 | 93.7 | N/A | N/A | 9.59 |
| PC6MT | Phosphate/ Citrate | 4% Mann/1% Trehalose | 0.10% Poloxamer | 5 | 6.01 | 93.3 | N/A | N/A | 10.23 |
| C6GT | Citrate | 2% Glycine/ 1% Trehalose | 0.10% Poloxamer | 25 | 6.04 | 94.1 | N/A | N/A | 11.77 |
| C6MT | Citrate | 4% Mann/1% Trehalose | 0.10% Poloxamer | 25 | 6.05 | 92.9 | N/A | N/A | 9.39 |
| PC6MT | Phosphate/ Citrate | 4% Mann/1% Trehalose | 0.10% Poloxamer | 25 | 6.07 | 92.8 | N/A | N/A | 10.20 |
| C6GT | Citrate | 2% Glycine/ 1% Trehalose | 0.10% Poloxamer | 37 | 6.13 | 94.0 | N/A | N/A | 8.54 |
| C6MT | Citrate | 4% Mann/1% Trehalose | 0.10% Poloxamer | 37 | 6.02 | 91.8 | N/A | N/A | 9.24 |
| PC6MT | Phosphate/ Citrate | 4% Mann/1% Trehalose | 0.10% Poloxamer | 37 | 6.20 | 91.4 | N/A | N/A | 10.32 |

(5) 8 weeks* Please note that a new SE-HPLC column was used from this time point forward; the previous column had lost resolution. Thus, the numbers have gone up slightly.

| ID | Buffer (10 mM) | Tonicity Modifier | Surfactant | Temp (° C.) | pH | SE | RP | IE | Conc. (mg/mL) |
|---|---|---|---|---|---|---|---|---|---|
| C6GT | Citrate | 2% Glycine/ 1% Trehalose | 0.10% Poloxamer | 5 | 6.15 | 95.5 | N/A | N/A | 11.15 |
| C6MT | Citrate | 4% Mann/1% Trehalose | 0.10% Poloxamer | 5 | 6.23 | 95.6 | N/A | N/A | 11.27 |
| PC6MT | Phosphate/ Citrate | 4% Mann/1% Trehalose | 0.10% Poloxamer | 5 | 6.13 | 94.6 | N/A | N/A | 10.15 |
| C6GT | Citrate | 2% Glycine/ 1% Trehalose | 0.10% Poloxamer | 25 | 6.17 | 95.4 | N/A | N/A | 11.77 |
| C6MT | Citrate | 4% Mann/1% Trehalose | 0.10% Poloxamer | 25 | 6.18 | 93.9 | N/A | N/A | 9.00 |
| PC6MT | Phosphate/ Citrate | 4% Mann/1% Trehalose | 0.10% Poloxamer | 25 | 6.12 | 93.6 | N/A | N/A | 9.38 |

(6) 12 Weeks

| ID | Buffer (10 mM) | Tonicity Modifier | Surfactant | Temp (° C.) | pH | SE | RP | IE | Conc. (mg/mL) |
|---|---|---|---|---|---|---|---|---|---|
| C6GT | Citrate | 2% Glycine/ 1% Trehalose | 0.10% Poloxamer | 5 | 6.16 | 94.3 | N/A | N/A | 11.60 |
| C6MT | Citrate | 4% Mann/1% Trehalose | 0.10% Poloxamer | 5 | 6.17 | 93.1 | N/A | N/A | 9.39 |
| PC6MT | Phosphate/ Citrate | 4% Mann/1% Trehalose | 0.10% Poloxamer | 5 | 6.18 | 92.8 | N/A | N/A | 9.95 |
| C6GT | Citrate | 2% Glycine/ 1% Trehalose | 0.10% Poloxamer | 25 | 6.17 | 93.8 | N/A | N/A | 11.27 |

TABLE 8-continued

Summary of stability results from exemplary formulation candidates

| ID | Buffer (10 mM) | Tonicity Modifier | Surfactant | Temp (° C.) | pH | HPLC Purity (%) SE | RP | IE | Conc. (mg/mL) |
|---|---|---|---|---|---|---|---|---|---|
| C6MT | Citrate | 4% Mann/1% Trehalose | 0.10% Poloxamer | 25 | 6.21 | 91.8 | N/A | N/A | 9.37 |
| PC6MT | Phosphate/ Citrate | 4% Mann/1% Trehalose | 0.10% Poloxamer | 25 | 6.18 | 91.3 | N/A | N/A | 9.93 |
| (7) 16 Weeks | | | | | | | | | |
| C6GT | Citrate | 2% Glycine/ 1% Trehalose | 0.10% Poloxamer | 5 | 6.07 | 94.3 | N/A | N/A | 11.22 |
| C6MT | Citrate | 4% Mann/1% Trehalose | 0.10% Poloxamer | 5 | 6.04 | 93.6 | N/A | N/A | 9.52 |
| PC6MT | Phosphate/ Citrate | 4% Mann/1% Trehalose | 0.10% Poloxamer | 5 | 6.05 | 93.2 | N/A | N/A | 9.85 |
| C6GT | Citrate | 2% Glycine/ 1% Trehalose | 0.10% Poloxamer | 25 | 6.07 | 94.1 | N/A | N/A | 11.33 |
| C6MT | Citrate | 4% Mann/1% Trehalose | 0.10% Poloxamer | 25 | 6.03 | 92.4 | N/A | N/A | 9.29 |
| PC6MT | Phosphate/ Citrate | 4% Mann/1% Trehalose | 0.10% Poloxamer | 25 | 6.07 | 91.8 | N/A | N/A | 9.74 |

Example 3

ZC-701 Stability

ZC-701 stability was examined over the course of a three-month study. Lyophilized Test Article ZC-701-GMP1 in the current formulation buffer (50 mM Citrate, 4% Mannitol, 1% Trehalose and 0.1% Pluronic F-68, pH 6.0) was compared to Control Sample ZC-701-B18-10 in Phosphate Buffered Saline (PBS) pH 6.2. Samples were incubated at 4° C., room temperature, and −80° C. for up to 92 days. ZC-701 stability was evaluated in terms of protein concentration, GAA enzymatic activity, monomer purity, and CI-MPR receptor binding.

ZC-701-GMP1 in formulation buffer was stable at 4° C. and −80° C. during the entire three-month study. ZC-701-B18-10 in PBS pH 6.2 was also stable except for an increase in compound multimerization that occurred at 4° C. The amount of ZC-701-B18-10 multimer increased from <1% to over 25% in three months at 4° C. In contrast, the amount of multimer ZC-701-GMP1 was maintained at <1% for the entire study. This demonstrates that the current formulation buffer provides improved compound stability compared to PBS pH 6.2.

Briefly, ZC-701-GMP1 material from GMP bulk drug lot 106A12-017782 was lyophilized in an engineering run of the fill/finish lyophilization cycle at Althea (4ER-067 engineering run). Vials of ZC-701-GMP1 containing 35 mg ZC-701 in formulation buffer were reconstituted with 6.8 ml water, aliquoted, and stored at 4° C., room temperature (RT), or −80° C. The Control Sample ZC-701-B18-10, formulated in PBS pH 6.2, was thawed from −80° C. storage.

RT samples were analyzed on Day 0 and Day 1. Other samples were analyzed on Days 0, 1, 7, 28 and 92. Analysis included protein concentration determination by $A_{280}$ spectrophotometry, GAA PNP enzyme activity analysis, reducing and non-reducing SDS-PAGE analysis, size exclusion chromatography analysis, PNGase F/SDS-PAGE analysis, and receptor binding by an IGF-II receptor competitive binding assay. Enzyme activity was also monitored in a freeze/thaw experiment.

Protein Concentration Determination

Figure 11:
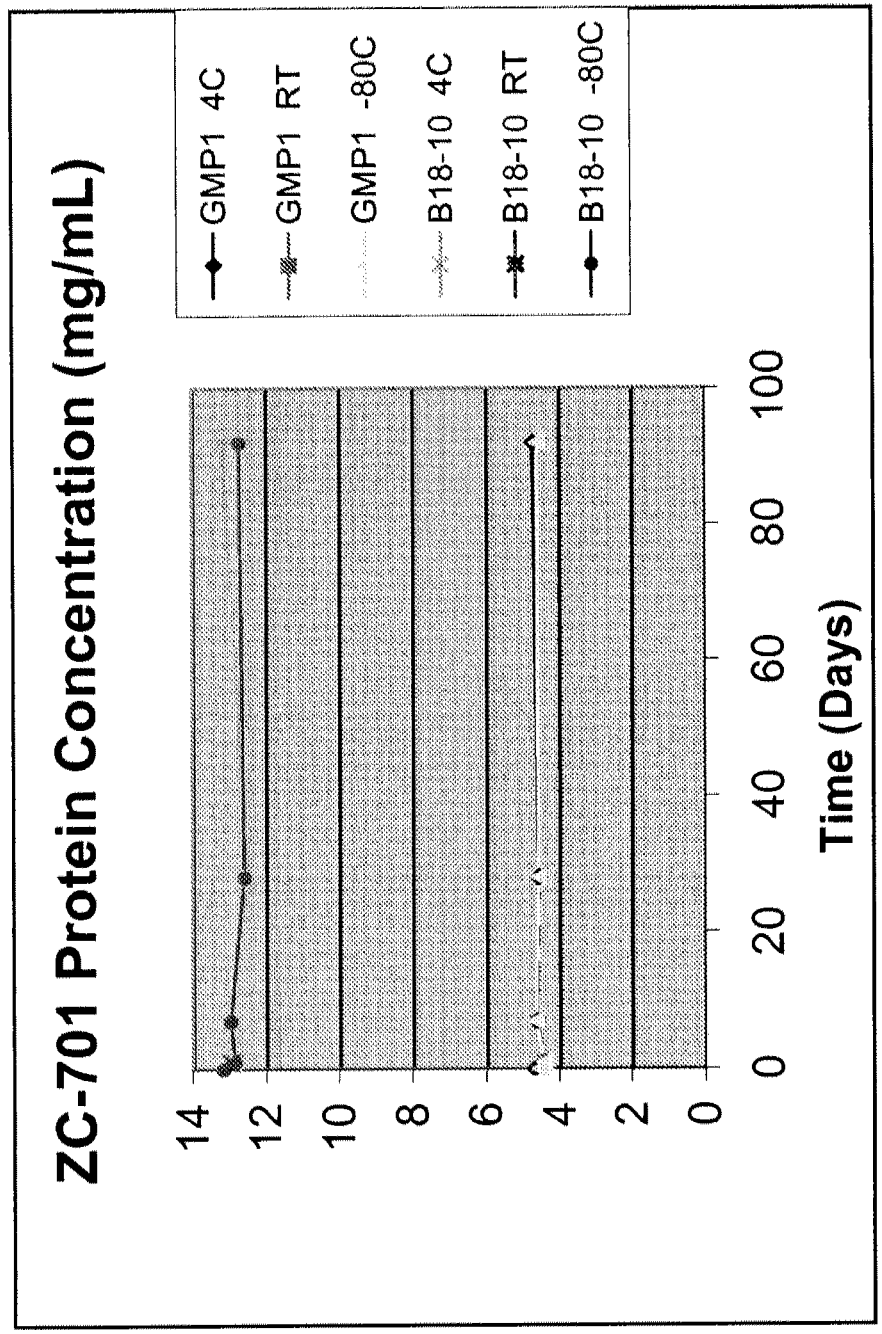
FIG. 11 illustrates exemplary measurement of sample protein concentration by $A_{280}$ spectrophotometry. The protein concentrations of tested samples were stable over the 92-day course of the study. Sample protein concentration was determined by $A_{280}$ measurement using an extinction coefficient of 1.59 $cm^{-1}$ $(mg/ml)^{-1}$.

As shown in FIG. 11 and Table 9, the protein concentrations of all samples were stable over the 92-day course of the study. Sample protein concentration was determined by $A_{280}$ measurement using an extinction coefficient of 1.59 $cm^{-1}$ $(mg/ml)^{-1}$.

TABLE 9

Exemplary Measurement of sample protein concentration by $A_{280}$ spectrophotometry
Concentration (mg/mL)

| Sample | Time (Days) | | | | |
|---|---|---|---|---|---|
| | 0 | 1 | 7 | 28 | 92 |
| GMP1 4 C. | 4.67 | 4.40 | 4.60 | 4.55 | 4.69 |
| GMP1 RT | | 4.41 | | | |
| GMP1 −80 C. | 4.53 | 4.40 | 4.63 | 4.56 | 4.59 |
| B18-10 4 C. | | 12.89 | 13.06 | 12.49 | 13.17 |
| B18-10 RT | | 12.96 | | | |
| B18-10 −80 C. | 13.17 | 12.86 | 12.97 | 12.59 | 12.73 |

GAA Enzymatic Activity

Figure 12:
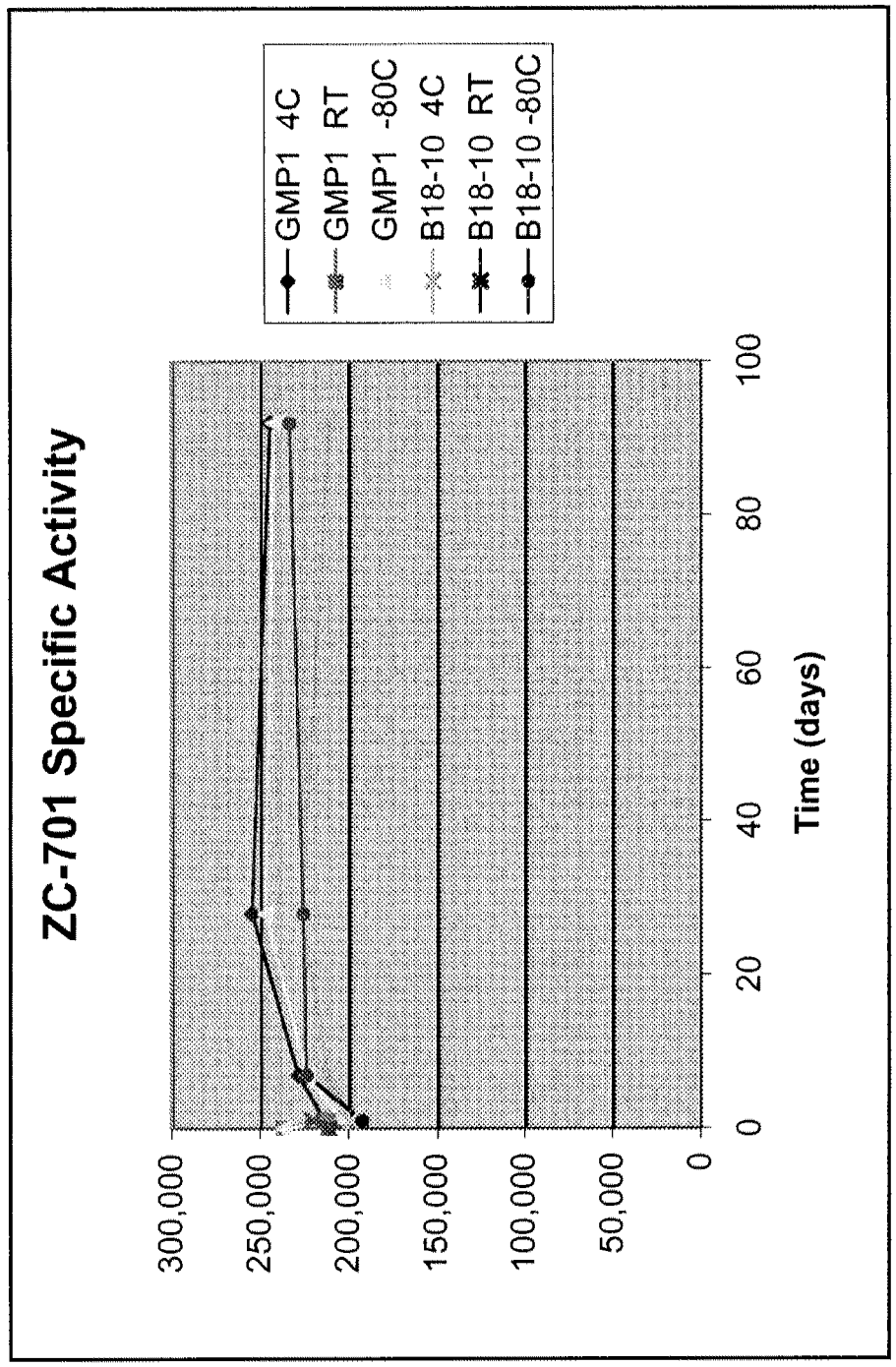
FIG. 12 illustrates exemplary measurement of GAA enzymatic activity by PNP assay. Unit definition: Enzyme required to hydrolyze 1 nmol of para-nitrophenol alpha-glucoside (Sigma#N1377) in one hour at 37° C. in a reaction containing 10 mM substrate and 100 mM sodium acetate pH 4.2. 50 µl reactions were stopped with 300 µl of 100 mM sodium carbonate. Hydrolyzed substrate was detected at 405 nm and compared to a standard curve of p-nitrophenol (Sigma #N7660).

As shown in FIG. 12 and Table 10, which show results from GAA PNP enzymatic activity analysis, samples were stable over the 92-day course of the study. Unit definition: Enzyme required to hydrolyze 1 nmol of para-nitrolphenol alpha-glucoside (Sigma#N1377) in one hour at 37° C. in a reaction containing 10 mM substrate and 100 mM sodium acetate pH 4.2. 50 μl reactions were stopped with 300 μl of 100 mM sodium carbonate. Hydrolyzed substrate was detected at 405 nm and compared to a standard curve of p-nitrophenol (Sigma #N7660). PNP Units are divided by the protein concentrations shown in Table 9 to yield the enzyme specific activity.

TABLE 10

Exemplary measurement of GAA enzymatic activity by PNP assay.
Specific Activity (PNP Units/mg)

| Sample | Time (Days) | | | | |
|---|---|---|---|---|---|
| | 0 * | 1 | 7 | 28 | 92 |
| GMP1 4 C. | 236,302 | 213,423 | 227,939 | 254,534 | 244,283 |
| GMP1 RT | 236,302 | 211,455 | | | |

TABLE 10-continued

Exemplary measurement of GAA enzymatic activity by PNP assay.
Specific Activity (PNP Units/mg)

| Sample | Time (Days) | | | | |
|---|---|---|---|---|---|
| | 0 * | 1 | 7 | 28 | 92 |
| GMP1 −80 C. | 236,302 | 203,854 | 223,022 | 246,870 | 242,376 |
| B18-10 4 C. | 210,944 | 198,675 | 211,125 | 225,980 | 210,565 |
| B18-10 RT | 210,944 | 220,106 | | | |
| B18-10 −80 C. | 210,944 | 192,210 | 223,491 | 225,452 | 232,963 |

Figure 13:
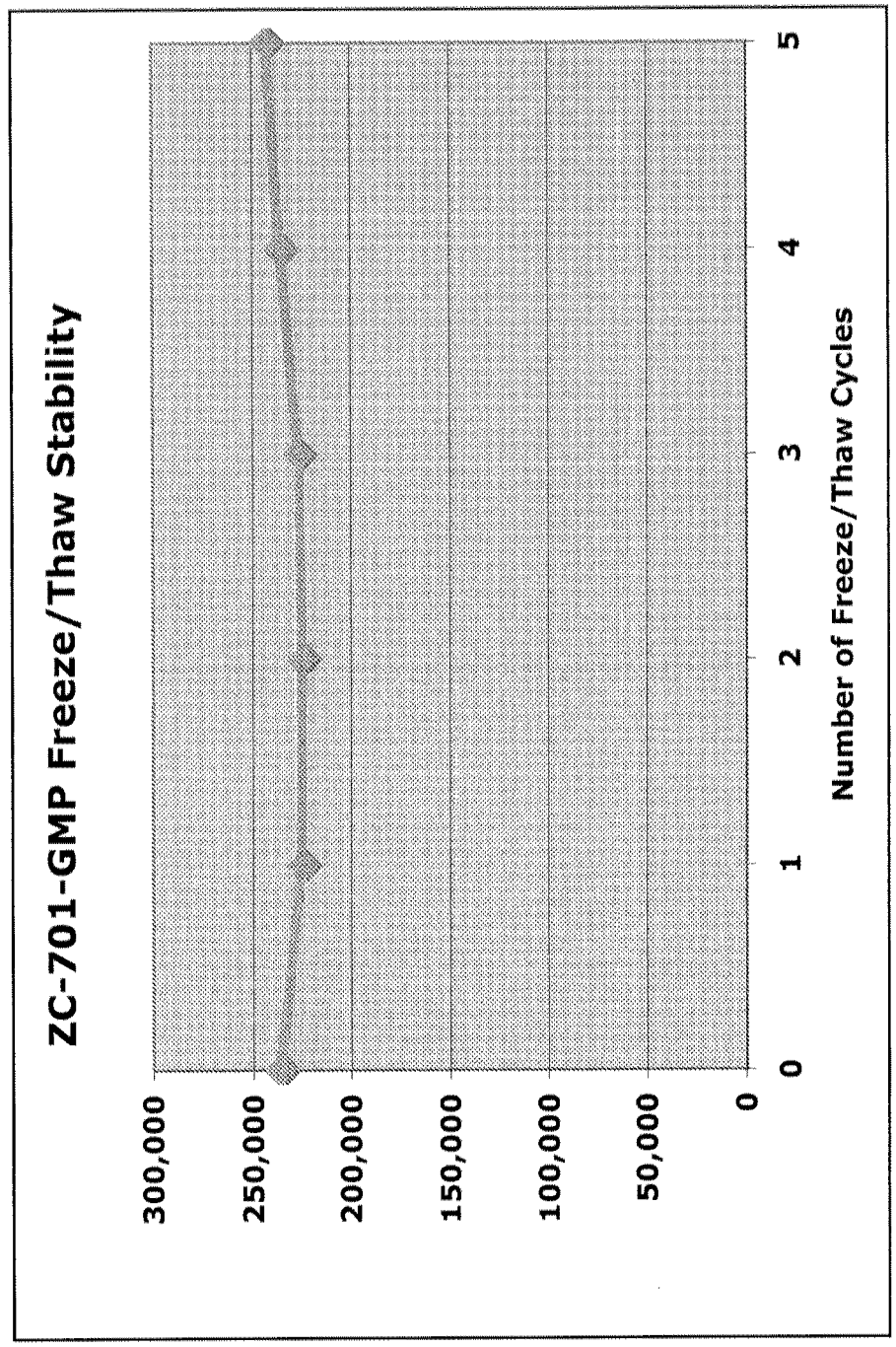
FIG. 13 illustrates exemplary measurement of ZC-701-GMP1 GAA activity by PNP assay in samples that underwent up to 5 cycles of snap-freezing in liquid nitrogen, followed by thawing in room-temperature water.

As described above, GAA enzyme activity was monitored in freeze/thaw samples. ZC-701 GMP1 GAA activity was measured by PNP assay in samples that underwent up to 5 cycles of snap-freezing in liquid nitrogen, followed by thawing in room temperature water. As shown in FIG. 13, the compound is resistant to 5 freeze/thaws.

SDS-PAGE Analysis

Figure 14:
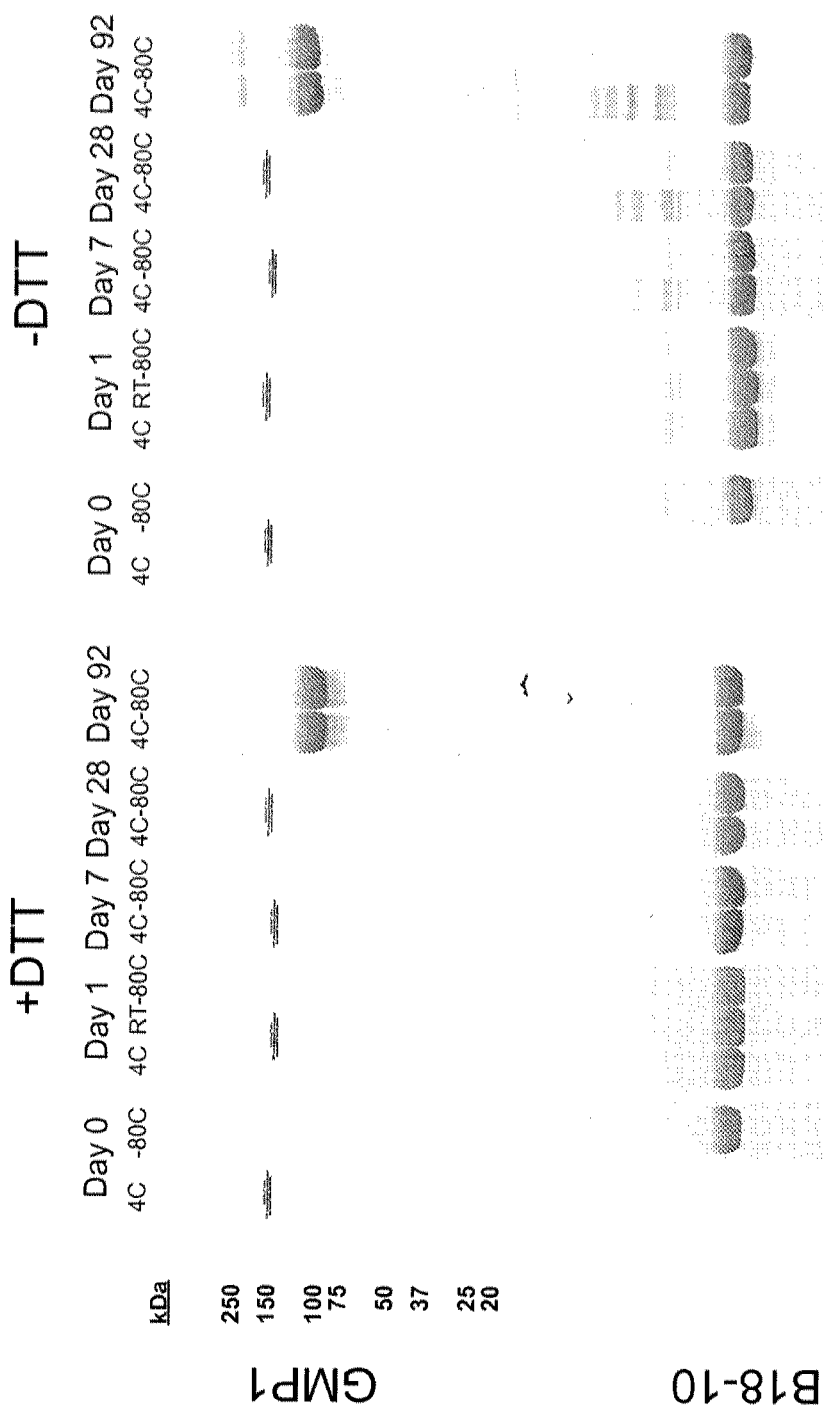
FIG. 14 illustrates exemplary reducing (+DTT) and non-reducing (−DTT) SDS-PAGE. Lanes containing 10 µg of ZC-701 sample were separated on XT Precast Gels 4-12% Bis-Tris (Bio Rad #345-0124) under reducing conditions (100 mM DTT) or non-reducing conditions (no DTT) as described by the manufacturer at 200 volts for 50 minutes. Gels were stained with Imperial Protein Stain (Pierce #24615).

As shown in FIG. 14, ZC-701-GMP1 samples stored at 4° C. and −80° C. were virtually indistinguishable by SDS-PAGE over the course of 92 days. ZC-701-B18-10 samples at −80° C. were also stable, however 4° C. samples displayed an increase in high molecular weight ZC-701 multimer over time.

Size Exclusion Chromatography Analysis

Figure 15:
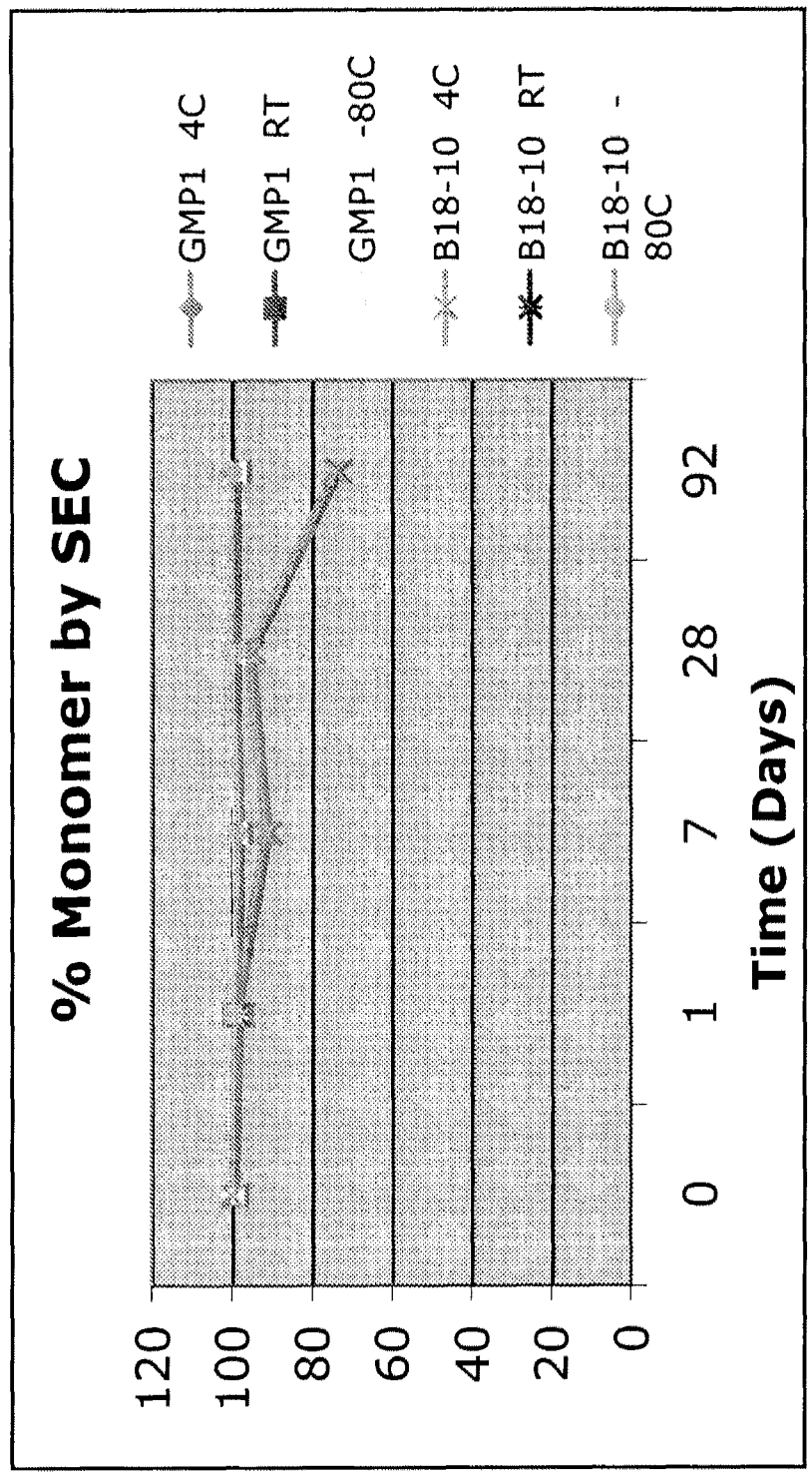
FIG. 15 illustrates exemplary stability analysis. Samples were separated by analytical size exclusion chromatography. The percent ZC-701 present as a monomeric form was determined by loading 33 µg of ZC-701 in phosphate buffered saline pH 6.2 at room temperature at 0.25 ml/min over a TSKgel G2000 $SW_{XL}$ 30 cm×7.8 mm column and a TSKgel G3000 $SW_{XL}$ 30 cm×7.8 mm column connected in series. Multimerization level was defined as the % fraction larger than ZC-701 monomer.

As shown in FIG. 15 and Table 11, SEC analysis showed that fraction of ZC-701 compound present as the monomer form was constant during the study with the exception of ZC-701-B18-10 incubated at 4° C. Over the course of three months, approximately 25% of this sample converted into the high molecular weight multimer form. The percent ZC-701 present as a monomeric form was determined by loading 33 µg of ZC-701 in phosphate buffered saline pH 6.2 at room temperature at 0.25 ml/min over a TSKgel G2000 $SW_{XL}$ 30 cm×7.8 mm column and a TSKgel G3000 $SW_{XL}$ 30 cm×7.8 mm column connected in series. Multimerization level is defined as the % fraction larger than ZC-701 monomer.

TABLE 11

Stability samples were separated by analytical
size exclusion chromatography
% Monomer by SEC

| Sample | Time (Days) | | | | |
|---|---|---|---|---|---|
| | 0 | 1 | 7 | 28 | 92 |
| GMP1 4 C. | >99 | >99 | >99 | >99 | >99 |
| GMP1 RT | | >99 | | | |
| GMP1 −80 C. | >99 | 99.0 | >99 | >99 | >99 |
| B18-10 4 C. | >99 | >99 | 91.7 | 96.0 | 74.3 |
| B18-10 RT | | 98.41 | | | |
| B18-10 −80 C. | | >99 | 98.7 | >99 | >99 |

PNGase F/SDS-PAGE Analysis

Typically, approximately 20-30% of ZC-701 molecules are cleaved by furin during tissue culture production. The furin enzyme cleaves the polypeptide backbone of the ZC-701 molecule, but the resulting two portions of the protein remain associated through disulfide linkages, maintaining protein functionality. PNase F/SDS-PAGE analysis methods can resolve and quantify the following three protein species: Intact: ZC-701 molecules that have not been cleaved by furin; Cleaved: ZC-701 molecules with a backbone cleaved by furin, but that retain both portions of the cleaved molecule through disulfide linkages, and also retain complete functionality; and Truncated: ZC-701 molecules that have been cleaved by furin and have lost the N-terminal protein of the molecule. Truncated protein is generally not functional.

For PNGase F treatment, 2 µg of sample protein was diluted into 1×PNGase buffer (50 mM sodium phosphate, pH 7.5, 0.1% SDS) and denatured at 95° C. for five minutes. Triton X-100 was added to 0.75% followed by 1 µl of PNGase F (New England Biolabs #P0704). Samples were incubated at 37° C. overnight. Samples were then separated by SDS-PAGE on 4-12% Bis-Tris gels (Bio-Rad) at 200 volts for 120 minutes in the presence or absence of 100 mM DTT. Gels were treated with Imperial Blue stain as described by the manufacturer (Pierce). The amount of each protein species was quantitated using UN-SCAN-IT software (Silk Scientific).

Figure 16:
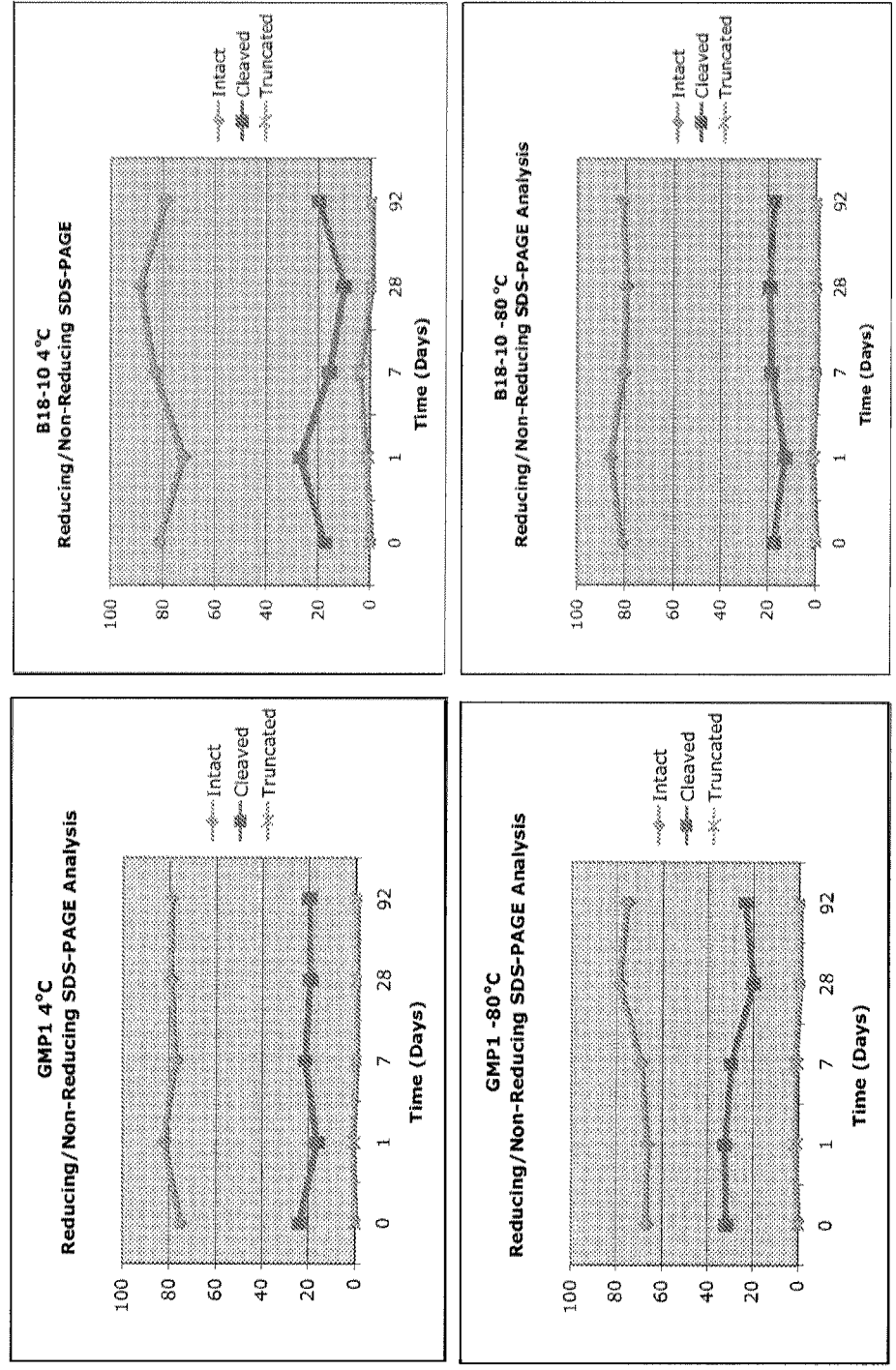
FIG. 16 illustrates exemplary quantitation of furin-cleaved protein species by PNGase F/SDS-PAGE analysis of various samples.

Results from PNGase F/SDS-PAGE analysis of the stability samples are shown in FIG. 16. The amounts of intact and cleaved protein species remain relatively constant for all of the samples. The amount of inactive, truncated ZC-701 is negligible over the three-month study.

IGF-II Receptor Competitive Binding Analysis

The affinity of ZC-701 samples for the IGF-II receptor (IGF-IIR) was examined in competitive binding experiments performed in a 96-well plate format. IGF-IIR was coated at room temperature overnight onto Reacti-bind white plates (Pierce, Cat#437111) in Coating Buffer (0.05M Carbonate buffer, pH 9.6) at a concentration of 0.5 µg/well. Plates were washed with wash buffer (Phosphate Buffered Saline plus 0.05% Tween-20), then blocked in Super Blocking Buffer (Pierce, Cat#37516) for 1 hour. After another plate washing, 8 nM biotinylated IGF-II ligand (Cell Sciences) was added to wells. Along with the biotinylated IGF-II ligand, wells also contained serial dilutions of the ZC-701 protein samples or non-biotinylated IGF-II ligand to act as binding inhibitors for the biotinylated IGF-II ligand. Following a two-hour rocking incubation, plates were washed and bound biotinylated IGF-II was detected with a streptavidin-HRP incubation (R&D, Cat#890803, 1:200 dilution in blocking buffer, 30 minutes), followed by a Super Elisa Pico Chemiluminescent Substrate incubation (Pierce, Cat#37070, 5 minutes). The chemiluminescent signal was measured at 425 nm, and $IC_{50}$ values were calculated for each sample.

Table 12 shows the $IC_{50}$ values for the stability samples in the IGF-II competitive binding assay. Day-to-day assay variations are evident from the non-biotinylated IGF-II control sample values. A general increase in $IC_{50}$ values for the samples was not observed, indicating that the samples retained IGF-II receptor binding activity.

TABLE 12

Determination of $IC_{50}$ values for stability samples
by an IGF-II receptor competitive binding assay
% Monomer by SEC

| Sample | Time (Days) | | | | |
|---|---|---|---|---|---|
| | 0 | 1 | 7 | 28 | 92 |
| GMP1 4 C. | >99 | >99 | >99 | >99 | >99 |
| GMP1 RT | | >99 | | | |
| GMP1 −80 C. | >99 | 99.0 | >99 | >99 | >99 |
| B18-10 4 C. | >99 | >99 | 91.7 | 96.0 | 74.3 |
| B18-10 RT | | 98.41 | | | |
| B18-10 −80 C. | | >99 | 98.7 | >99 | >99 |

Taken together, these data demonstrate that ZC-701-GMP1 reconstituted in formulation buffer at a concentration of 4.5 mg/ml is stable in solution at 4° C., and at −80° C. for at least 92 days. ZC-701-GMP1 is also stable for 24 hours at room temperature. ZC-701-B18-10 in PBS pH 6.2 was also stable except for an increase in compound multimerization that occurred at 4° C. The amount of ZC-701-B18-10 multimer increased from <1% to over 25% in three months at 4° C. In contrast, the amount of multimer ZC-701-GMP1 was maintained at <1% for the entire study. This demonstrates that the current formulation buffer provides improved compound stability compared to PBS pH 6.2.

Example 4

The stability of ZC-701 in Saline Solution

The stability of ZC-701 in saline solution was measured under conditions that mimicked preparation of the compound for patient infusion. 6.8 mL of water was added to a vial of lyophilized ZC-701-GMP1 (Vial 3, Lot#1-FIN-0692, formulated in 50 mM citrate, pH 6.0, 4% mannitol, 1% trehalose, and 0.1% pluronic F-68). The protein concentration of the reconstituted ZC-701 material was determined by $A_{280}$ measurement to be 4.7 mg/mL (extinction coefficient=1.59 cm$^{-1}$ (mg/ml)$^{-1}$). The material was diluted to either 2 mg/mL or 4 mg/mL in room-temperature 0.9% saline (9 g/L NaCl in water), then incubated at room temperature (~21° C.) for up to 24 hours. At the end of 0, 1, 2, 4, 8, 21 and 24 hour time points, aliquots were removed and stored on ice. Analysis included protein concentration determination by $A_{280}$ spectrophotometry, GAA PNP enzymatic assay, size exclusion chromatography (SEC) and SDS-PAGE.

Protein Concentration Determination

Figure 17:
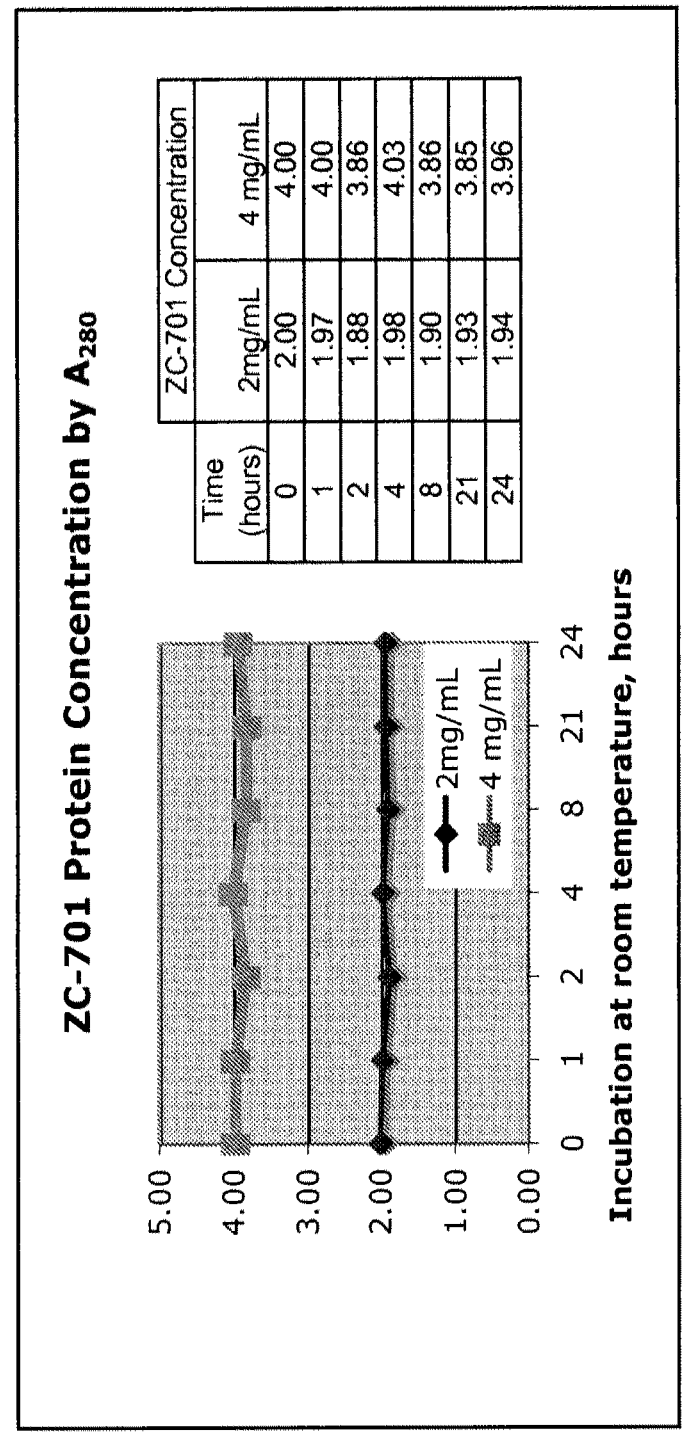
FIG. 17 illustrates exemplary results indicating protein concentration of ZC-701 from an exemplary stability analysis. Concentrations were determined by $A_{280}$ measurement using an extinction coefficient of 1.59 $cm^{-1}$ $(mg/ml)^{-1}$.

Aliquots from each time point were centrifuged at 4° C. at 15,000 g for one minute and visually examined for the presence of precipitate. No sample precipitation was observed at any time during the study. Sample protein concentration was determined by $A_{280}$ measurement using an extinction coefficient of 1.59 cm$^{-1}$ (mg/ml)$^{-1}$ (FIG. 17). The protein concentration was stable over the course of 24 hours.

GAA Enzymatic Activity

Figure 18:
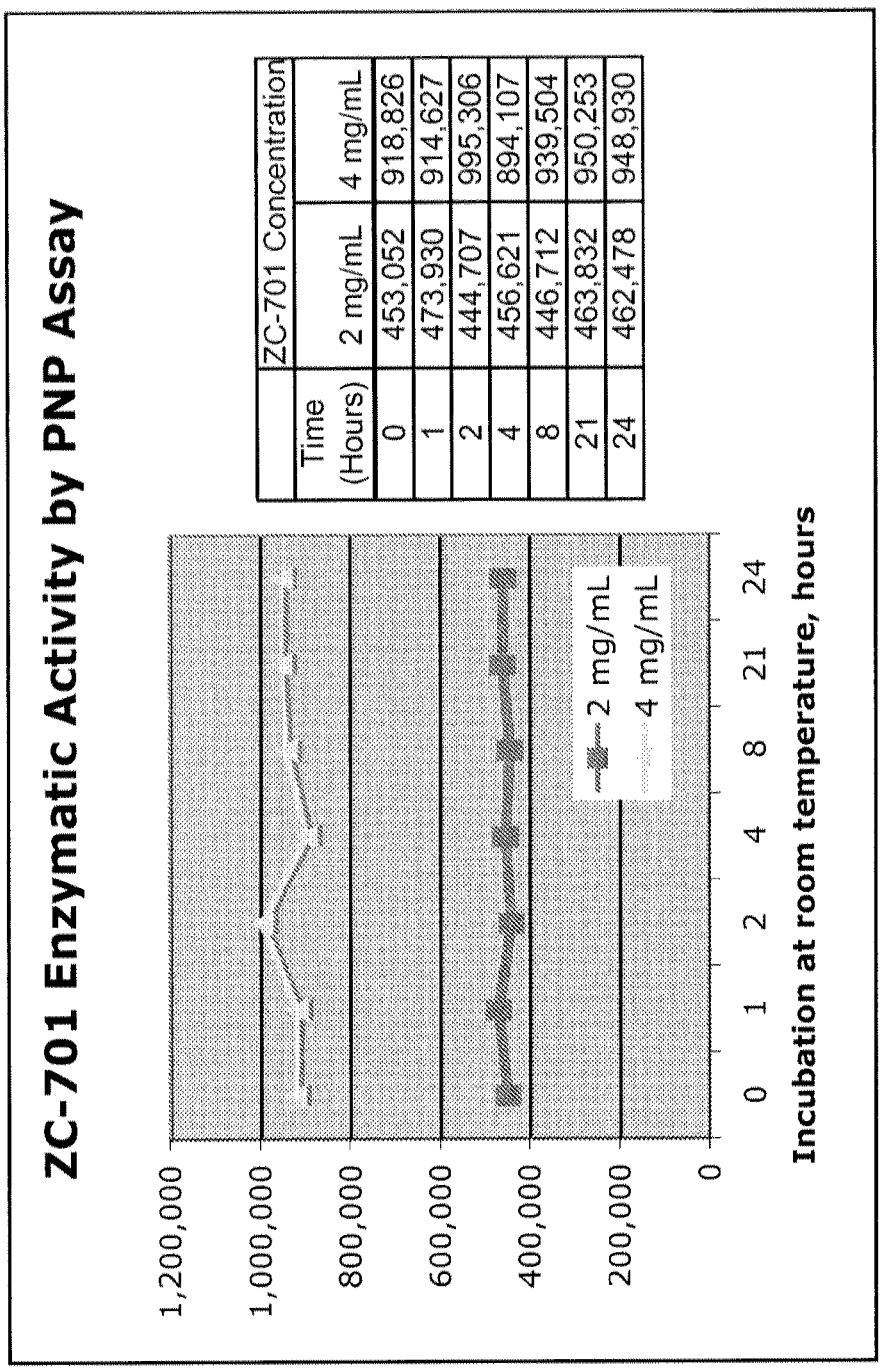
FIG. 18 illustrates exemplary results showing enzymatic activity of ZC-701 diluted in saline. Unit definition: Enzyme required to hydrolyze 1 nmol of para-nitrolphenol alpha-glucoside (Sigma#N1377) in one hour at 37° C. in a reaction containing 10 mM substrate and 100 mM sodium acetate pH 4.2. 50 µl reactions were stopped with 300 µl of 100 mM sodium carbonate. Hydrolyzed substrate was detected at 405 nm and compared to a standard curve of p-nitrophenol (Sigma #N7660).

The GAA PNP enzymatic assay was performed on all time point samples (FIG. 18). For the purposes of this assay, one (1) enzyme unit is defined as Enzyme required to hydrolyze 1 nmol of para-nitrolphenol alpha-glucoside (Sigma#N1377) in one hour at 37° C. in a reaction containing 10 mM substrate and 100 mM sodium acetate pH4.2. 50 µl reactions were stopped with 300 µl of 100 mM sodium carbonate. Hydrolyzed substrate was detected at 405 nm and compared to a standard curve of p-nitrophenol (Sigma #N7660). As shown in FIG. 18, the enzymatic activity of ZC-701 diluted in saline was stable over the course of 24 hours.

Size Exclusion Chromatography Analysis

Samples from 0, 2, 4 and 21 hour time points were also analyzed by size-exclusion chromatography (SEC) (Table 13). Briefly, the percent of ZC-701 present in a monomeric form was determined by loading 33 µg of ZC-701 in phosphate buffered saline pH 7.2 at room temperature at 0.2 ml/min over a TSKgel G2000 SW$_{XL}$ 30 cm×7.8 mm column and a TSKgel G3000 SW$_{XL}$ 30 cm×7.8 mm column connected in series. Multimerization level is defined as the % fraction larger than ZC-701 monomer. As shown in Table 11, the monomer levels of the samples were stable over the course of 21 hours.

TABLE 13

SEC analysis of ZC-701 diluted in saline

| | 2 mg/mL ZC-701 | | 4 mg/mL ZC-701 | |
|---|---|---|---|---|
| Time (Hours) | Multimer, % | Monomer, % | Multimer, % | Monomer, % |
| 0 | <1.0 | >99 | <1.0 | >99 |
| 2 | <1.0 | >99 | <1.0 | >99 |
| 4 | <1.0 | >99 | <1.0 | >99 |
| 21 | <1.0 | >99 | <1.0 | >99 |

SDS-PAGE Analysis

Figure 19:
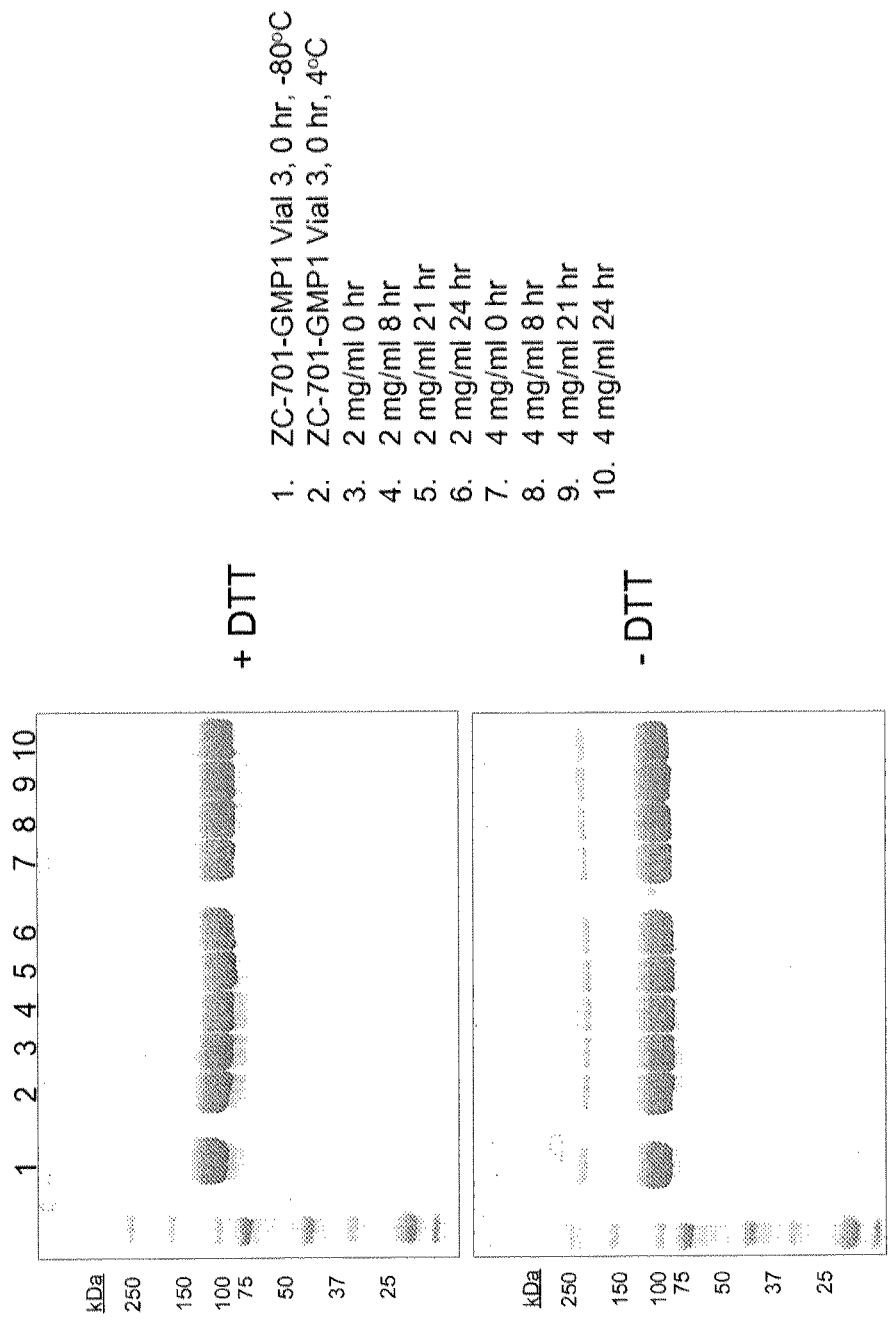
FIG. 19 illustrates exemplary SDS-PAGE analysis of ZC-701 diluted in saline. Lanes containing 10 µg of ZC-701 sample were separated on XT Precast Gels 4-12% Bis-Tris (Bio Rad #345-0124) under reducing conditions (100 mM DTT, top gel) or non-reducing conditions (no DTT, bottom gel) as described by the manufacturer at 200 volts for 50 minutes. Gels were stained with Imperial Protein Stain (Pierce #24615). Lanes 1 and 2, contained ZC-701 material that was not diluted into saline. Lane 1 material was stored at −80° C. and Lane 2 material was stored at 4° C.

Samples from 0, 8, 21 and 24 hour time points were analyzed by reducing and non-reducing SDS-PAGE (FIG. 19). Samples diluted in saline for up to 24 hours were indistinguishable from control samples.

The above experiments show that ZC-701 formulated at approximately 5 mg/mL in 50 mM citrate, pH 6.0, 4% mannitol, 1% trehalose, and 0.1% Pluronic® F-68 produces a compound that is stable for up to 24 hours when diluted into saline to concentrations of 2 mg/mL or 4 mg/mL. This dilution into saline mimics the conditions suitable for the preparation of ZC-701 for patient infusion.

Example 5

Analytical Data for ZC-701 Formulation

ZC-701 (Lot #1-FIN-0692) lyophilized from formulation buffer (50 mM Citrate, 4% Mannitol, 1% Trehalose and 0.1% Pluronic® F-68, pH 6.0) was analyzed after storage for 12 months at 2-8° C. As shown below in Table 14, products were analyzed based on their appearance, dissolution, pH, moisture content, purity, potency, and strength. Product attributes for storage at 2-8° C. fell into an acceptable range and were similar to the product attributes at release.

TABLE 14

Exemplary ZC-701 Analytical Data Summary

| Test | Acceptance Criteria | Time Zero; Release | 12 months; 2-8° C. |
|---|---|---|---|
| Appearance, Lyophilized | White to off-white powder | White powder | White powder |
| Appearance After Dissolution | Clear, colorless solution with no visible particles | Clear, colorless solution with no visible particles | Clear, colorless solution with no visible particles |
| Dissolution Time | Report time for cake to totally dissolve | 1 min; 32 sec | 2 min; 20 sec |
| pH | Report Result | 6.1 | 6.04 |
| Moisture (KF) | Report Result | 0.66% | 0.87% |
| Strength 280 nm | ±10% of target quantity | 33.4 mg/vial | 32.7 mg/vial |
| SDS-PAGE, Reduced | >95% pure | 100% | 96.7% |
| SDS-PAGE, Non-Reduced | Report Result | Intact: 95.8% | Intact: 96.4% |

TABLE 14-continued

Exemplary ZC-701 Analytical Data Summary

| Test | Acceptance Criteria | Time Zero; Release | 12 months; 2-8° C. |
|---|---|---|---|
| SEC-HPLC | >95% pure | 96.4% | 96.2% |
| GAA Activity | 150,000-300,000 nmole PNP/hr/mg | 217,631.55 nmole PNP/hr/mg | 243,947 nmole PNP/hr/mg |
| Receptor Binding Assay | <75 nM | $IC_{50}$ = 33.4 nM | $IC_{50}$ = 23.9 nM |

EQUIVALENTS

The foregoing has been a description of certain non-limiting embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

INCORPORATION BY REFERENCE

All publications and patent documents cited in this application are incorporated by reference in their entirety for all purposes to the same extent as if the contents of each individual publication or patent document were incorporated herein.

What is claimed is:

1. A pharmaceutical composition for treating Pompe disease comprising a recombinant human acid alpha-glucosidase (GAA) in a formulation comprising:
    a) a buffering agent selected from the group consisting of histidine, sodium acetate, citrate, phosphate, succinate, Tris and combinations thereof;
    b) a stabilizing agent selected from the group consisting of sucrose, arginine, sorbitol, mannitol, glycine, trehalose and combinations thereof;
    c) a tonicity modifier selected from the group consisting of glycine, sorbitol, sucrose, mannitol, sodium chloride, dextrose, arginine and combinations thereof;
    d) a bulking agent selected from the group consisting of sucrose, mannitol, glycine, sodium chloride, dextran, trehalose and combinations thereof; and
    e) a poloxamer, wherein the poloxamer is Pluronic® F-68 at a concentration ranging between 0.001% and 0.2%,
wherein the pH ranges from approximately 4.0 to 7.0.

2. The pharmaceutical composition of claim 1, wherein the pH is approximately 6.0.

3. The pharmaceutical composition of claim 1, wherein the pharmaceutical composition is in a form suitable for parenteral administration.

4. The pharmaceutical composition of claim 1, wherein the pharmaceutical composition is a lyophilized mixture.

5. The pharmaceutical composition of claim 1, wherein the recombinant human GAA is produced from CHO cells.

6. The pharmaceutical composition of claim 1, wherein the recombinant human GAA has modified glycosylation levels as compared to naturally-occurring human GAA.

7. The pharmaceutical composition of claim 6, wherein the recombinant human GAA contains increased mannose-6-phosphates as compared to naturally-occurring human GAA.

8. The pharmaceutical composition of claim 1, wherein the recombinant human GAA is a fusion protein comprising recombinant human GAA and a lysosomal targeting peptide having an amino acid sequence having at least 70% identity to the amino acid sequence of mature human IGF-II (SEQ ID NO:1), wherein the fusion protein comprises an amino acid sequence having at least 80% identity to the amino acid sequence set forth in SEQ ID NO: 2.

9. The pharmaceutical composition of claim 8, wherein the lysosomal targeting peptide is an IGF-II mutein and comprises a mutation within a region corresponding to amino acids 34-40 of SEQ ID NO:1 such that the mutation abolishes at least one furin protease cleavage site.

10. The pharmaceutical composition of claim 8, wherein the lysosomal targeting peptide is an IGF-II mutein that has diminished binding affinity for the IGF-I receptor relative to the affinity of naturally-occurring human IGF-II for the IGF-I receptor and/or has diminished binding affinity for the insulin receptor relative to the affinity of naturally-occurring human IGF-II for the insulin receptor.

11. The pharmaceutical composition of claim 8, wherein the fusion protein comprises the amino acid sequence set forth in SEQ ID NO:2.

12. The pharmaceutical composition of claim 1, wherein the recombinant human GAA is in a formulation containing approximately 50 mM citrate, 4% mannitol, 1% trehalose, and 0.1% Pluronic® F-68 at a pH of approximately 6.0.

13. A pharmaceutical composition comprising a lyophilized mixture of a recombinant human acid alpha-glucosidase (GAA), sodium citrate, mannitol, trehalose, and Pluronic® F-68.

14. The pharmaceutical composition of claim 13, wherein the recombinant human GAA is produced from CHO cells.

15. The pharmaceutical composition of claim 13, wherein the recombinant human GAA has modified glycosylation levels as compared to naturally-occurring human GAA.

16. The pharmaceutical composition of claim 13, wherein the recombinant human GAA contains increased mannose-6-phosphates as compared to naturally-occurring human GAA.

17. The pharmaceutical composition of claim 13, wherein the recombinant human GAA is a fusion protein comprising recombinant human GAA and a lysosomal targeting peptide having an amino acid sequence having at least 70% identity to the amino acid sequence of mature human IGF-II (SEQ ID NO:1), wherein the fusion protein comprises an amino acid sequence having at least 80% identity to the amino acid sequence set forth in SEQ ID NO: 2.

18. The pharmaceutical composition of claim 17, wherein the lysosomal targeting peptide is an IGF-II mutein and comprises a mutation within a region corresponding to amino acids 34-40 of SEQ ID NO:1 such that the mutation abolishes at least one furin protease cleavage site.

19. The pharmaceutical composition of claim 17, wherein the lysosomal targeting peptide is an IGF-II mutein that has diminished binding affinity for the IGF-I receptor relative to the affinity of naturally-occurring human IGF-II for the IGF-I receptor and/or has diminished binding affinity for the insulin receptor relative to the affinity of naturally-occurring human IGF-II for the insulin receptor.

20. The pharmaceutical composition of claim 17, wherein the fusion protein comprises the amino acid sequence set forth in SEQ ID NO:2.

21. A method of treating Pompe disease comprising administering to a subject in need of treatment the pharmaceutical composition of claim 12.

* * * * *